US011267861B2

(12) United States Patent
Zimmer et al.

(10) Patent No.: US 11,267,861 B2
(45) Date of Patent: Mar. 8, 2022

(54) PEPTIDE-OLIGOUREA FOLDAMER COMPOUNDS AND METHODS OF THEIR USE

(71) Applicant: UREKA SARL, Mulhouse (FR)

(72) Inventors: Robert H. Zimmer, Mulhouse (FR); Sebastien Goudreau, Bordeaux (FR); Gilles Guichard, Gradignan (FR); Juliette Fremaux, Pessac (FR); Claire Venin, Talence (FR); Laura Mauran, Talence (FR)

(73) Assignee: UREKA SARL, Mulhouse (FR)

( * ) Notice: Subject to any disclaimer, the term of this patent is extended or adjusted under 35 U.S.C. 154(b) by 490 days.

(21) Appl. No.: 15/491,929

(22) Filed: Apr. 19, 2017

(65) Prior Publication Data
US 2017/0298112 A1     Oct. 19, 2017

Related U.S. Application Data

(60) Provisional application No. 62/324,414, filed on Apr. 19, 2016.

(51) Int. Cl.
*C07K 14/605* (2006.01)
*C07K 7/08* (2006.01)
(Continued)

(52) U.S. Cl.
CPC .............. *C07K 14/605* (2013.01); *C07K 7/08* (2013.01); *C08L 75/02* (2013.01); *G01N 33/50* (2013.01); *G01N 33/74* (2013.01); *A61K 38/00* (2013.01)

(58) Field of Classification Search
CPC ........ A61K 38/00; C07K 14/605; C07K 7/08; C08L 75/02; G01N 33/50; G01N 33/74
See application file for complete search history.

(56) References Cited

U.S. PATENT DOCUMENTS

| 5,424,286 A | 6/1995 | Eng |
| 5,595,756 A | 1/1997 | Bally et al. |
| (Continued) | | |

FOREIGN PATENT DOCUMENTS

| EP | 1640361 | 3/2006 |
| JP | 2006-500906 A1 | 1/2006 |
| (Continued) | | |

OTHER PUBLICATIONS

Burgess et al., Solid Phase Syntheses of Oligoureas, J. Am. Chem. Soc., vol. 119:1556-1564 (1997) (Year: 1997).*
(Continued)

*Primary Examiner* — Randall L Beane
(74) *Attorney, Agent, or Firm* — Bryan D. Zerhusen; Nicholas R. Herrel; Cantor Colburn LLP

(57) ABSTRACT

The present description provides compositions and methods for producing therapeutic compounds. In another aspect the description provides methods for administering the oligomeric compounds for the treatment and prevention of disease in a mammal. In particular, the present disclosure relates to medicaments comprising various novel oligomeric compounds and pharmaceutically acceptable salts thereof. The compounds of the present disclosure may optionally be administered with at least one of a pharmaceutically acceptable excipient, additional pharmacologically active agent or a combination thereof.

10 Claims, 13 Drawing Sheets

Specification includes a Sequence Listing.

(51) Int. Cl.
    C08L 75/02    (2006.01)
    G01N 33/50    (2006.01)
    G01N 33/74    (2006.01)
    A61K 38/00    (2006.01)

(56) References Cited

U.S. PATENT DOCUMENTS

| | | | |
|---|---|---|---|
| 6,958,384 | B2 | 10/2005 | Gellman et al. |
| 7,060,845 | B2 | 6/2006 | Guichard |
| 7,186,828 | B2 | 3/2007 | Guichard |
| 7,691,807 | B2 | 4/2010 | Violette |
| 7,858,737 | B2 | 12/2010 | Gellman et al. |
| 8,138,145 | B2 | 3/2012 | Violette et al. |
| 9,243,040 | B2 | 1/2016 | Cheng |
| 10,398,750 | B2 * | 9/2019 | Zimmer ............... C08G 69/10 |
| 2002/0143191 | A1 * | 10/2002 | Guichard ............ C07C 275/14 |
| | | | 548/549 |
| 2005/0038105 | A1 | 2/2005 | Guichard |
| 2006/0211625 | A1 | 9/2006 | Violette |
| 2008/0214625 | A1 | 9/2008 | Kley |
| 2009/0312246 | A1 | 12/2009 | Baron |
| 2010/0099185 | A1 | 4/2010 | Horne |
| 2011/0009443 | A1 | 1/2011 | Freeman-Cook |
| 2011/0118440 | A1 | 5/2011 | Gellman et al. |
| 2011/0212138 | A1 | 9/2011 | Houchin |
| 2012/0115782 | A1 | 5/2012 | Mehal |
| 2012/0021530 | A1 | 6/2012 | Gellman et al. |
| 2013/0116179 | A1 | 5/2013 | Hess |
| 2015/0141323 | A1 * | 5/2015 | Guichard ............... A61K 38/07 |
| | | | 514/2.3 |

FOREIGN PATENT DOCUMENTS

| | | | |
|---|---|---|---|
| JP | 2009-525744 A1 | 7/2009 | |
| JP | 2014-132021 A1 | 7/2014 | |
| WO | WO 2003/029198 | 4/2003 | |
| WO | WO 2012/085479 | 6/2012 | |
| WO | WO 2013/102209 | 7/2013 | |
| WO | WO 2015/024955 | 2/2015 | |
| WO | WO-2015024955 A1 * | 2/2015 | ............ A61K 47/59 |
| WO | WO 2016/164413 A1 | 10/2016 | |
| WO | WO 2017/037142 | 3/2017 | |
| WO | WO 2017/037150 | 3/2017 | |

OTHER PUBLICATIONS

Miller et al., The class B G-protein-coupled GLP-1 receptor: an important target for the treatment of type-2 diabetes mellitus, International Journal of Obesity Supplements, vol. 4:S9-S13 (2014) (Year: 2014).*

Johnson et al., A Potent α/β-Peptide Analogue of GLP-1 with Prolonged Action in Vivo, J. Am. Chem. Soc., vol. 136:12848-12851 (Sep. 5, 2014) (Year: 2014).*

Claudon et al., Consequences of Isostructural Main-Chain Modifications for the Design of Antimicrobial Foldamers: Helical Mimics of Host-Defense Peptides Based on a Heterogeneous Amide/Urea Backbone, Angew. Chem. Int. Ed., vol. 49:333-336 (2010) (Year: 2010).*

Boeijen et al., Solid-Phase Synthesis of Oligourea Peptidomimetics Employing the Fmoc Protection Strategy, J. Org. Chem., vol. 66:8454-8462 (2001) (Year: 2001).*

Douat-Casassus et al., Microwave-Enhanced Solid-Phase Synthesis of N,N'-Linked Aliphatic Oligoureas and Related Hybrids, Org. Lett., vol. 14(12):3130-3133 (published online May 30, 2012) (Year: 2012).*

Amy Luo, scribbr.com, "Colons (:)", attached as pdf, 7 pages (May 30, 2019), also available at https://www.scribbr.com/language-rules/colons/ (lasted visited Jan. 21, 2021) (Year: 2019).* grammarly.com, "Colons", 4 pages, (online Apr. 5, 2017), available at https://www.grammarly.com/blog/colon-2/ (last visited Jan. 21, 2021) (Year: 2017).*

Runge, S., Wulff, B.S., Madsen, K., Brauner-Osborne, H. and Knudsen, L.B. (2003), Different domains of the glucagon and glucagon-like peptide-1 receptors provide the critical determinants of ligand selectivity, Brit. J. Pharmacol., 138: pp. 787-794.

Chicchi, G.G., Graziano, M.P., Koch, G., Hey, P. Sullivan, K., Vicario, P.P. and Casieri, M.A. (1997), Alterations in receptor activation and divalent cation activation of agonist binding by deletion of intracellular domains of the glucagon receptor, J. Biol. Chem., 272: pp. 7765.

Remington's Pharmaceutical Sciences, 1980, vol. 16, Mack Publishing Company, Easton, Pa., pp. 61 and 424.

Adams, P. D et al. "PHENIX: a comprehensive Python-based system for macromolecular structure solution", Acta Crystallogr. D Biol. Crystallogr. 66, 213-221 (2010).

Aisenbrey, C., et al., "Solid state NMR studies of oligourea foldamers: interaction of 15N-labelled amphiphilic helices with oriented lipid membanes", Org. Biomol. Chem., 10, 1440-1447 (2012).

Arvidsson, et al., On the Antimicrobial and Hemolytic Activities of Amphiphilic Beta-peptides. ChemBioChem, 2001, 10771-10773.

Ballaster, P., "Anion binding in covalent and self-assembled molecular capsule", Chem. Soc. Rev. 2010, 39 (10), 3810-3830.

Bathany, K., et al., "Sequencing of oligourea foldamers by tandem mass spectrometry", Journal of the American Society for Mass Spectrometry, Feb. 12, 2013, 24(3):458-462.

Berkessel, A.; Roland, K.; Neudorfl, J. M. "Asymmetric Morita-Baylis-Hillman Reaction Catalyzed by Isophoronediamine-Derived Bis(thio)urea Organocatalysts", Org. Lett. 2006, 8, 4195-4198.

Biros, S. M., et al. "Structure and binding properties of water-soluble cavitands and capsules", Chem. Soc. Rev. 2007, 36 (1), 93-104.

Boeijen, A., et a., "Solid-Phase Synthesis of oligourea peptidomimetics employing the Fmoc protection strategy", J. Org. Chem, 2001, 66, 8454-8462.

Boeijen, et al., "Solid-Phase Synthesis of Oligourea Peptidomimetics", Eur. J. Org. Chem., 1999, 2127-2135.

Bouillere, F., et al., "Foldamers containing c-amino acid residues or their analogues: structural features and applications", Amino Acids, 41, 687-707 (2011).

Bromley, et al., "Peptide and protein building blocks for synthetic biology: from programming biomolecules to self-organized biomolecular systems", ACS Chem. Biol. 3, 38-50 (2008).

Brown, R.A., et al., "Induction of unexpected left-handed helicity by an N-Terninal L-Amino acid in an otherwise aciral peptide chain", Angew Chem Int Ed. 2012, 51, 1395-1399.

Burgess, et al., "Solid Phase Synthesis of Oligoureas", J. of American Chem. Soc. v119(7): 1556-1564(1997).

Burgess, et al., "Solid-phase syntheses of unnatural biopolymers containing repeating urea units", Agnew. Chem. Int. Ed. Engl. 34, 907-909 (1995).

Castelletto, et al., Amyloid peptides incorporating a core sequence from the amyloid beta peptide and gamma amino acids: relating bioactivity to self-assembly, Chem. Commun., 2011, 47, 12470-12472.

Chen, et al., "Determination of the Secondary Structures of Proteins by Circular Dichroism and Optical Rotatory Dispersion", Biochem. vol. 11, No. 22, 1972, pp. 4120-4131.

Chicchi, et al., "Alterations in receptor activation and divalent cation activation of agonist binding by deletion of intracellular domains of the glucagon receptor", J. Biol. Chem., 272: pp. 7765 (1997).

Cho, C., et al., "An unnatural Biopolymer", Science 1993, 261, 1303-1305.

Cho., C., et al., Synthesis and screening of linear and cyclic oligocarbamate libraries. Discovery of high affinity ligands for CPIIb/IIIa, J. Am. Chem. Soc. 1998, 120(31), 7706-7718.

Choi, Soo Hyuk, "Helical structures of unnatural peptides for biological applications", Biomedical Engineering Letters, vol. 3., No. 4, pp. 226-231, Dec. 1, 2013.

Claudon, P., et al., "Consequences of Isostructural Main-Chain modifications for the design of antimicrobial foldamers: Helical memics of host-defense peptides based on a heterogeneous amide/urea backbone", Angew. Chem. Int. Ed. Engl. 49, 333-336 (2010).

(56) References Cited

OTHER PUBLICATIONS

Collie, Gavin W., et al., "Shaping quaternary assemblies of water-soluable non-peptide helical goldamers by sequence manipulation", Nature Chemistry, vol. 7, No. 11, Sep. 28, 2015, pp. 871-878.

Conn, M. M., et al., Self-assembling capsules, Chem. Rev. 1997, 97 (5), 1647-1668.

Connon, S. J. "Organocatalysis mediated by (thio)urea derivatives", Chem. Eur. J. 2006, 12, 5418-5427.

Coward, "N—Me-pAB-Glu-gamma-Glu-gamma-Tyr(3-NO2): An Internally Quenched Fluorogenic Gamma-glutamyl Hudrolase Substrate", Bioorganic & Medicinal Chemistry Letters, Oxford GB, v11(12): 1561-1564 (2001).

Craig, et al., "Enhancing β3-peptide bundle stability by design", ChemBioChem 2011, 12 (7), 1035-1038.

Curran, D. P.; Kuo, L. H. "Altering the Stereochemistry of Allylation Reactions of Cyclic .alpha.-Sulfinyl Radicals with Diarylureas", J. Org. Chem. 1994, 59, 3259-3261.

Daniels, D. S., "High-resolution structure of a beta-peptide bundle", J. Am. Chem. Soc. 129, 1532-1533 (2007).

Delano, W.L., "The PyMOL molecular graphic system", DeLano Scientific, San Carols, CA (2002).

Der, et al., "The use of coiled coils could facilitate the modular, predictable design of protein nanocages", Nat. Biotechnol, 31 (9) 809-810 (2013).

Douat-Casassus, et al., "Microwave-enhanced solid-phase synthesis of N,N'-linked aliphatic oligoureas and related hybrids", Org. Lett. 14,3130-3133 (2012).

Doyle, A. G.; Jacobsen, E. N. "Small-molecule H-bond donors in asymmetric catalysis", Chem. Rev. 2007, 107, 5713-43.

Ebalunode, et al., "Structure-based shape pharmacophore modeling for the discovery of novel anesthetic compounds", Bioorg. Med. Chem. 2009, 17 (14) 5133-5138.

Emsley, et al., "Features and development of Coot", Acta Crystallogr. D Biol. Crystallogr. 66, 486-501 (2010).

Evans, P. "Scaling and assessment of data quality", Acta Crystallogr. D Biol. Crystallogr.,D 62 (Pt 1) 72-82 (2006).

Faiella, M. et al. "An artificial di-iron oxo-protein with phenol oxidase activity", Nat. Chem. Biol. 5(12), 882-884 (2009) (Published in final form as Nat Chem Biol . Dec. 2009 ; 5(12): doi:10.1038/nchembio.257.pp. 1 -7).

Ferrand, Y., et al. "Diastereoselective Encapsulation of Tartaric Acid by a Helical Aromatic Oligoamide", J. Am. Chem. Soc., 132 (23), 7858-7859 (2010).

Fischer Lucile, "Succinimidyl carbamate derivatives from N-protected alpha-amino acids and dipeptides- Synthesis of Ureidopeptides and Oligourea/Peptide Hybrids", European Journal of Organic Chemistry, No. 15:2511-2525, May 1, 2007.

Fischer Lucile, et al., "Folding and self-assembly of aromatic and aliphatic urea oligomers: Towards connecting structure and function", Organic & Biomolecular Chemistry, 8(14):3101-3117, Jan. 1, 2010.

Fischer, L., "The Canonical Helix of Urea Oligomers at Atomic Resolution: Insights Into Folding-Induced Axial Organization", Angew. Chem. Int. Ed. Engl. 2010, 49, 1067-1070.

Fischer, L., et al., "The canonical helix of urea oligomers at atomic resolution: insights into folding-induced axial organization", Angew. Chem. Int. Ed. Engl. 2010, 122, 1085-1088.

Fletcher, et al., "Self-assembling cages from coiled-coil peptide modules", Science 340,595-599 (2013)—ScienceExpress http://www.sciencemag.org/content/early/recent/ Apr. 11, 2013 / p. 1 / 10.1126/science. 1233936.

Frackenpohl, et al., "The outstanding biological stability of beta- and gama-peptides toward proteylytic enzymes: an in vitro investigation with fifteen peptidases", Chembiochem 2, 445-455 (2001).

Fremaux, J. et al. "α-Peptide/Oligourea Chimeras: Stabilization of Short α-helices by Non Peptide Helical Foldamers", Angew. Chem. Int. Ed. Engl. , vol. 54, 2015, pp. 9816-9820 DOI: 10.1002/anie. 201500901R201500901.

Fremaux, J., et al., "Influence of archiral unites with gem-dimethy substituents on the helical charater of aliphatic oligourea foldamers", Chem Comm (Camb). Aug. 28, 2013, 49(67); 7415-7. Doi:10.1039/c3cc40961a.

Fremaux, J., et al., G. "Condensation approach to aliphatic oligourea foldamers: helices with N-(pyrrolidin-2-ylmethyl)ureido junctions", Angew. Chem. Int. Ed Engl. 50, 11382-11385 (2011).

Gao, Yi et al., "Theoretical Study of the Secondary Structures of Unionized Poly(y-D-glutamic acid)", Molecular Physics (2004), 102(23-24), pp. 2491-2498.

Garric, J., et al. "Encapsulation of Small Polar Guests in Molecular Apple Peels", Chemical Eng. Journal, 13 (30), 8454-8462 (2007).

Garric, J., et al. "Molecular Apple Peels", Angew. Chem. Int. Ed. Engl., 44 (13), 1954-1958 (2005).

Gellman, et al., "Foldamers: A Manifesto", Acc. Chem. Res. 31, 173-180 (1998).

Gennari, C., et al., "Synthesis of sulfonamide-pseudopeptides: new chiral unnatural oligomers", Angew. Chem. Int. Ed. 1994, 33, 2067-2069.

Ghirlanda, G. et al. "Volatile anesthetic modulation of oligomerization equilibria in a hexameric model peptide", FEBS Lett. 578, 140-144 (2004).

Giuliano, M. W., et al. "An alpha/beta-peptide helix bundle with a pure beta3-amino acid core and a distinctive quaternary structure", J. Am. Chem. Soc. 131, 9860-9861 (2009).

Goodman, et al., "Biophysical and structural characterization of a robust octameric β-peptide bundle", J. Am. Chem. Soc. 2007, 129 (47), 14746-14751.

Goodman, et al., "Foldamers as versatile frameworks for the design and evolution of function", Nat. Chem Biol. 3, 252-262 (2007).

Gradišar, et al., "Design of a single-chain polypeptide tetrahedron assembled from coiled-coil segments", Nat. Chem. Biol. 9, 362-366 (2013).

Gradišar, et al., "Self-assembled bionanostructures: proteins following the lead of DNA nanostructures", J. Nanobiotechnology 12, 4, 1-9, (2014).

Guichard, et al., "Synthetic foldamers", Chem. Commun. 47, 5933-5941 (2011).

Guichard, G., et al., "Effective Preparation of O-succinimidyl-2(tert-butoxycarbonylamino) ethylcarbamate derivatives from B-amino Acids. Application to the synthesis of urea-containing pseudopeptides and oligoureas", J. Org. Chem. 1999, 64, 8702-8705.

Guichard, G., et al., "Solution structure determination of oligoureas using methylene spin state selective NMR at $^{13}$C natural abundance", Magn. Reson. Chem., 2008, 46, 918-924.

Gura, "Cancer Models: Systems for Identifying New Drugs are Often Faulty", Science vol. 278 (1997), 1041-1042.

Hamuro et al., "De Novo Design of Antibacterial B-Peptides", J. Am. Chem. Soc., 1999, 121, 12200-12201.

Harbury, P. B., et al., "High-resolution protein design with backbone freedom", Science 282, 1462-1467(1998).

Hemmerlin C et al.: "Helix-forming oligoureas: Temperature-dependent NMR, structure determination, and circular dichroism of a nonamer with functionalized side chains", Helvetica Chimica Acta, Verlag Helvetica Chimica Acta, CH, vol. 85, No. 11, Jan. 1, 2002 (Jan. 1, 2002), pp. 3692-3711, XP002417783, ISSN: 0018-019X, DOI: 10.1002/1522-2675(200211)85:11<3692::AID-HLCA3692>3.0.00;2-W oligoureas 1 and 2.

Hernandez, H., et al., "Determining the stoichiometry and interactions of macromolecular assemblies from mass spectrometry", Nat. Protoc. 2, 715-726 (2007).

Hill, R. et al., "De novo design of helical bundles as models for understanding protein folding and function", Acc. Chem. Res. 33, 745-754 (2000).

Hintermann, et al., "Gamma-Peptides Forming More Stable Secondary Structures Than Alpha-Peptides: Synthesis and Helical NMR-Solution Structure of The Hexapeptide Analong of H-(Val-Ala-Leu)2-0H", Helvetica Chimica Acta, v81: 983-1002 (1998).

Horne, et al. "Interplay among side chain sequence, backbone composition, and residue rigidification in polypeptide folding and assembly", Proc. Natl. Acad. Sci. U.S., 105 (27) 9151-9156 (2008).

Horne, et al., "Helix bundle quaternary structure from alpha/beta-peptide foldamers", J. Am. Chem. Soc. 129, 4178-4180 (2007).

(56) References Cited

OTHER PUBLICATIONS

Horne, W.S., et al., "Foldamers with Heterogeneous Backbones", Acc. Chem. Res., 41, 1399-1408 (2008).
Hua, Y., et al. "Hydrophobic Collapse of Foldamer Capsules Drives Picomolar-Level Chloride Binding in Aqueous Acetonitrile Solutions", J. Am. Chem. Soc., 135 (38), 14401-14412 (2013).
Inouye, M., et al. "Saccharide-Dependent Induction of Chiral Helicity in Achiral Synthetic Hydrogen-Bonding Oligomers", J. Am. Chem. Soc., 126 (7), 2022-2027 (2004).
Jakab, G.; Tancon, C.; Zhang, Z.; Lippert, K. M.; Schreiner, P. R. "(Thio)urea Organocatalyst Equilibrium Acidities in DMSO", Org. Lett., 14, 1724-1727 (2012).
Joh, N. H. et al., "De novo design of a transmembrane $Zn^{2+}$-transporting four-helix bundle", Science 346, 1520-1524 (2014).
Johansson, et al., "A Designed Cavity in the Hydrophobic Core of a Four-α-Helix Bundle Improves Volatile Anesthetic Binding Affinity", Biochemistry 1998, 37 (5) 1421-1429.
Johnson, et al., "α-Helix mimicry with α/β-peptides", Methods Enzymol 523, 407-429 (2013).
Jones, C. R.; Pantos, G. D.; Morrison, A. J.; Smith, M. D. "Plagiarizing proteins: enhancing efficiency in asymmetric hydrogen-bonding catalysis through positive cooperativity", Angew. Chem. Int. Ed. Engl. 2009, 48, 7391-4.
Juwarker, H., et al., "Foldamers with helical cavities for binding complementary guests", Chem. Soc. Rev. 2009, 38 (12), 3316-3325.
Kabsch, W. "XDS", *Acta Crystallogr. D Biol. Crystallogr.* 66, 125-132 (2010)) and CCP4 (Winn, M. D. et al. Overview of the CCP4 suite and current developments. *Acta Crystallogr. D Biol. Crystallogr.* 67, 235-242 (2011).
Kichler, A., et al., "Histidine-rich amphipathic peptide antibiotics promote efficient delivery of DNA into mammalian cells", Proc. Natl. Acad. Sci. USA,100, 1564-1568 (2003).
Kim, J., et al., "The solid phase synthesis of oligoureas", Tetrahedron Letter., 1996, 37, 5305-5308.
King et al., "Computational design of self-assembling protein nanomaterials with atomic level accuracy", Science 336, 1171-1174 (2012).
King, et al., "Accurate design of co-assembling multi-component protein nanomaterials", Nature 510, 103-108 (2012).
Kodakek.T., et al., "The Rise, Fall and Reinvention of Combinatorial Chemistry", Chem. Commun., 47, 9757-9763 (2011).
Kofoed, J., et al., "A General Method for Designing Combinatorial Peptide Libraries Decodable by Amino Acid Analysis", J. Comb. Chem., 9, 1046-1052 (2007).
Koziara, K. B., et al., "Testing and validation of the automated topology builder (ATB) version 2.0: prediction of hydration free enthalpies", J. Comput. Aided Mol. Des. 2014, 28 (3), 221-223.
Lai, et al., "Principles for designing ordered protein assemblies"., Tends Cell Biol. 22, 653-661 (2012).
Lai, et al., "Structure of a 16-nm cage designed by using protein oligomers", Science 336, 1129 (2012).
Lai, et al., "Structure of a designed protein cage that self-assembles into a highly porous cube", Nat. Chem 6, 1065-1071 (2014).
Laskowski, R.A. "SURFNET: a program for visualizing molecular surfaces, cavities and intermolecular interactions", J. Mol. Graph. 13, 323-330 (1995).
Lear, J. D., et al., "Synthetic amphiphilic peptide models for protein ion channels", Science 240, 1177-1181 (1988).
Legrand, B., et al., "Robust helix formation in a new family of oligoureas based on a constrained bicyclic building block", Angew. Chem. Int. Ed., 2012, 51, 11267-11270.
Leplae et al. "Tolerance of Acyclic Residues in the Beta-Peptide 12-Helix: Access to Diverse Side-Chain Arrays for Biological Applications". J. Am. Chem. Soc., 2002, 124, 6820-1.
Li, X., et al., "Peptides of aminoxy acids as foldamers", Chem. Commun. 2006, 3367-3379.
Liu et al., "De Novo Design, Synthesis, and Characterization of Antimicrobial B-Peptides", J. Am Chem. Soc., 123, 7553-7559 (2001).
Liu, et al., "Atomic structure of a tryptophan-zipper pentamer", Proc. Natl. Sci. U.S.A. 2004, 101 (46) 16156-16161 (2004).
Liu, R., Loll, P. J. & Eckenhoff, R. G. "Structural basis for high-affinity volatile anesthetic binding in a natural 4-helix bundle protein", FASEB J. 19, 567-576 (2005).
Lombardo, C.M., et al., "Anatomy of an oligourea six-helix bundle", Journal of the American Chemical Society, Aug. 24, 2016, vol. 138, No. 33, pp. 10522-10530.
McCoy, A. J. et al. "Phaser crystallographic software", J. Appl. Crystallogr. 40, 658-674 (2007).
Mecozzi, S., et al., "The 55% solution: a formula for molecular recognition in the Liquid State", Chem. Eur. J. 1998, 4 (6), 1016-1022.
Murshudov, G. N. et al., "REFMAC5 for the refinement of macromolecular crystal structures", Acta Crystallogr. D Biol. Crystallogr. 67, 355-367 (2011).
Nelli, et al., "Structural characterization of short hybrid urea/carbamate (U/C) foldamers: a case of partial helix unwinding", Biopolymers 100, 687-697 (2013).
Nelli, Y.R., et al., "An activated building block for the introduction of the histidine side chain in aliphatic oligourea foldamers", Tetrahedron, 2012, 68, 4492-4500.
O'Shea, E.K., et al., "X-ray structure of the GCN4 leucine zipper, a two-stranded, parallel coiled coil", Science 254, 539-544 (1991).
Oh, et al., "Design, synthesis and characterization of antimicrobial pseudopeptides corresponding to membrane-active peptide", J. Peptide Res., 1999, 54, 129-136.
Okino, T.; Hoashi, Y.; Takemoto, Y. "Enantioselective Michael Reaction of Malonates to Nitroolefins Catalyzed by Bifunctional Organocatalysts", J. Am. Chem. Soc. 2003, 125, 12672-12673.
Oostenbrink, C., et al., "A biomolecular force field based on the free enthalpy of hydration and solvation: the GROMOS force-field parameter sets 53A5 and 53A6", J. Comput. Chem. 2004, 25 (13), 1656-1676.
Patch, et al., "Mimicry of bioactive peptides via non-natural, sequence-specific peptidomimetic oligomers", Curr. Op. Chem. Bio., 2002, 6, 872-877.
Pendem, N. et al., "Controlling Helix Formation in the γ-Peptide Superfamily: Heterogeneous Foldamers with Urea/Amide and Urea/Carbamate Backbones", Angew. Chem. Int. Ed. 2013, 52, 4147-4151.
Pendem, N.; et al., "Helix-Forming Propensity of Aliphatic Urea Oligomers Incorporating Noncanonical Residue Substitution Patterns", J. Am. Chem. Soc. 2013, 135, 4884-4892.
Pizzey, et al., "Characterization of nanofibers formed by self-assembly of beta-peptide oligomers using small angle x-ray scattering", J. Chem. Phys. 129, 095103 (2008).
Pomerantz, W. C. et al., "Nanofibers and lyotropic liquid crystals from a class of self-assembling beta-peptides", Angew. Chem. Int. Ed Engl. 47, 1241-1244 (2008).
Porter et al., "Mimicry of Host-Defense Peptides by Unnatural Oligomers: Antimicrobial Beta-Peptides", J. Am. Chem. Soc., 2002, 124, 7324-7330.
Porter et al., "Non-Haemolytic Beta-Amino-Acid Oligomers", Nature, 2000, 404, 565.
Pronk, S., et al., "Gromacs 4.5: a high-throughput and highly parallel open source molecular simulation toolkit", Bioinformatics, 29 (7), 845-854 (2013).
Reig, et al., "Altering the $O_2$-Dependent Reactivity of de novo due ferri proteins", Nat. Chem., 4 (11), 900-906 (2012).
Remington: The Science and Practice of Pharmacy, 20th Edition, A. R. Gennaro, Ed., Lippincott Williams & Wilkins, (2000), pp. 721-727.
Roy, Arup, et al., "Diversifying the structural architecture of synthetic oligomers: the hetero foldamer approach", Chemical Communications, 47(42):11593-11611, Jan. 1, 2011.
Rufo, et al., "Short peptides self-assemble to produce catalytic amyloids", Nat. Chem. 6 (4), 303-309 (2014).
Runge, et al., "Different domains of the glucagon and glucagon-like peptide-1 receptors provide the critical determinants of ligand selectivity", Brit. J. Pharmacol., 138: pp. 787-794 (2003).

(56) References Cited

OTHER PUBLICATIONS

Schuttelkopf, et al., "PRODRG: a tool for high-throughput crystallography of protein-ligand complexes", Acta Crystallogr. D Biol. Crystallogr. 60, 1355-1363 (2004).
Seebach, D., et al., "The World of b- and g-Peptides Comprised of Homologated Proteinogenic Amino Acids and Other Components", Chem. Biodivers. 2004, 1, 1111-1239.
Semetey, V., et al., "Stable helical secondary structure in short-chain N,N-Linked oligoureas bearing proteininogenic side chains", Angew. Chem. Int. Ed., 41, 1893-1895 (2002).
Singleton, M. L., et al., "Increasing the size of an aromatic helical foldamer cavity by strand intercalation", Angew. Chem. Int. Ed. Engl. 2014, 53 (48), 13140-13144.
Smith, L.J., et al., "Analysis of main chain torsion angles in proteins: prediction of NMR coupling constants for native and random coil conformations", J. Mol. Biol., 255, 494-506 (1996).
Smrcina, et al., "Facile stereoselective synthesis of y-substituted y-amino acids from corresponding a-amino acids", Tetrahedron, 1997, 53, 12867-12874.
Sola, J., et al., "Nanometer-range communication of stereochemical information by reversible switching of molecular helicity", Angew. Chem. Int. Ed. 2010, 49, 6836-6839.
Soth and Nowick, "A peptide/Oligourea/Azapeptide Hybrid That Adopts a Hairpin Turn", J. Org. Chem. 1999, 64, 276-281.
Sporn et al., "Chemoprevention of Cancer," Carcinogenesis, vol. 21 (2000), 525-530.
Suk, J.-M., et al., "Indolocarbazole-Based Foldamers Capable of Binding Halides in Water", J. Am. Chem. Soc. 2008, 130 (36), 11868-11869.
Takemoto, Y. "Recognition and activation by ureas and thioureas: stereoselective reactions using ureas and thioureas as hydrogen-bonding donors", Org. Biomol. Chem. 2005, 3, 4299-306.
Tamilarasu, et al., "Targeting RNA with peptidomimetic oligomers in human cells", Biorg. Med. Chem. Let., 2001, 11, 505-7.
Tamilarasu, "High Affinity and Specific Binding of HIV-1 TAR RNA by a Tat-Derived Oligourea", Journal of the American Chemical Society (1999), 121 (7), 1597-1598.
Tamilarasu, "Supporting Information—High Affinity and Specific Binding of HIV-1 TAR RNA by a Tat-Derived Oligourea", Journal of the American Chemical Society (1999), 121(7), pp. S1-S12.
Tanatani, A., et al. "Foldamers as dynamic receptors: probing the mechanism of molecular association between helical oligomers and rodlike ligands", Angew. Chem. Int. Ed. Engl. 2002, 41 (2), 325.
Tegoni, M., et al., "Designing a functional type 2 copper center that has nitrite reductase activity within α-helical coiled coils", Proc. Natl. Acad. Sci. U. S. A. 109, 21234-21239 (2012).
Toniolo, C., et al., "The polypeptide 310-helix", Trends Biochem Sci. 1991, 16, 350-353.
Vallavoju, N., et al., "Supramolecular photocatalysis: combining confinement and non-covalent interactions to control light initiated reactions", J. Chem. Soc. Rev. 2014, 43 (12), 4084-4101.
Violette, A., et al., "Exploring helical folding of oligoureas during chain elongation by high-resolution magic-angle-spinning (HRMAS) NMR spectroscopy", Chem. Eur. J. 2008, 14, 3874-3882.
Violette, et al., "Mimicking Helical Antibacterial Peptides with Nonpeptidic Folding Oligomers", Chemistry and Biology., vol. 13, No. 5, pp. 531-538, XP055307145, GB ISSN: 1074-5521, DOI: 10.1016/j.chembiol.2006.03.009 (2006).
Violette, et al., "N,N'-Linked Oligoureas as Foldamers: Chain Length Requirements for Helix Formation in Protic Solvent Investigated by Circular Dichroism, NMR Spectroscopy, and Molecular Dynamics", Journal of the American Chemical Society, vol. 127, No. 7, pp. 2156-2164, XP055152097, ISSN: 0002-7863, DOI: 10.1021/ja044392b (2005).
Wang, P. S. P., et al., "Design and high-resolution structure of a β3-peptide bundle catalyst", J. Am. Chem. Soc. 136, 6810-6813 (2014).
Wechsel, Romina, et al., "Inducing archiral aliphatic oligoureas to fold into helical conformations", Chemical Communications, vol. 50, No. 95, Jan. 1, 2014, pp. 15006-15009.

Winn, M. D. et al., "Overview of the CCP4 suite and current developments", Acta Crystallogr. D Biol. Crystallogr. 67, 235-242 (2011).
Wiszniewska, Anna et al: "Synthesis of peptidomimetics: An evaluation of p-nitrophenyl carbamate of ethylenediamine", Letters in Peptide Science, Jan. 1, 2003 (Jan. 1, 2003), pp. 33-39, XP055307149, Dordrecht DOI: 10.1007/13F02443640 Retrieved from the Internet: URL:http://rd.springer.com/content/pdf/10.1023/B:LIPS.0000014027.84594.e6.pdf.
Wiszniewska, et al., "p-Nitrophenoxycarbonyl derivatives of Boc-protected diaminoalkanes in the synthesis of encephalin peptidomimetics", J. Peptide Sci. 11:579-583 (2005).
Woolfson, D. N. "The design of coiled-coil structures and assemblies", Adv. Protein Chem. 70, 79-112 (2005).
Wu, et al., "Chloride Coordination by Oligoureas: From Mononuclear Crescents to Dinuclear Foldamers", Org. Lett. 2012, 14 (3), 684-687.
Xu, Y.-X., et al. "Folding of Aromatic Amide-Based Oligomers Induced by Benzene-1,3,5-tricarboxylate Anion in DMSO", J. Org. Chem. 2009, 74 (19), 7267-7273.
Yadav, et al. "Structure-based engineering of internal cavities in coiled-coil peptides", Biochemistry 44, 9723-9732 (2005).
Zaccai, et al., "A de novo peptide hexamer with a mutable channel", Nat. Chem. Biol. 7, 935-941 (2011).
Zhang, et al., "Structural DNA nanotechnology: state of the art and future perspective", J. Am. Chem. Soc. 136, 11198-11211 (2014).
Zhang, Z. & Fan, E. "Solid-phase and solution-phase syntheses of oligomeric guanidines bearing peptide side chains", J. Org. Chem. 80, 8801-8810 (2005).
International Search Report and Written Opinion for PCT/IB2017/000528, dated Jan. 9, 2018.
Japanese Office Action dated Dec. 10, 2019, for Application No. JP 2018-555643.
Drucker, DJ., et al., Glucagon-like peptide I stimulates insulin gene expression and increases cyclic AMP levels in a rat islet cell line, Proc. Natl. Acad. Sci. USA, vol. 84, pp. 3434-3438, May 1987.
Tamaki, C., et al., Pharmacological profile and clinical trial results of a long-acting, once weekly human GLP-1 receptor agonist Dulaglutide (Genetical Recombination), Folia Pharmacologica Japonica, 2015, vol. 146, pp. 215-224 (English title).
U.S. Appl. No. 16/206,433, filed Nov. 30, 2018, US 2019-0142905 A1.
Beck, et al., "Construction of matryoshka-type structures from supercharged protein nanocages", Angew. Chem. Int. Engl. 2015, 54 (3), 937-940 (Nov. 13, 2014).
Chandramouli, N., et al., Iterative design of a helically folded aromatic oligoamide sequence for the selective encapsulation of fructose, Nat. Chem. 2015, 7 (4), 334-341 (Mar. 16, 2015).
Douat, Celine, et al., "A Cell-penetrating foldamer with a bioreducible linkage for intracellular delivery of DNA," Agnew Chem Int Ed, 2015, 55, 11133-11137 (Aug. 5, 2015).
Maity, B., et al. "Use of the confined spaces of apo-ferritin and virus capsids as nanoreactors for catalytic reactions", Curr. Opin. Chem. Biol. 2015, 25, 88-97 (Jan. 8, 2015).
Nelli, Y. R.; "Isosteric Substitutions of Urea to Thiourea and Selenourea in Aliphatic Oligourea Foldamers: Site-Specific Perturbation of the Helix Geometry", Chem. Eur. J. 2015, 21, 2870-2880. (Dec. 21, 2014).
Rebilly, J.-N., et al., "Biomimetic cavity-based metal complexes", Chem. Soc. Rev., 44 (2), 467-489 (2015) (Oct. 16, 2014).
Tebo, et al., "Artificial metalloenzymes derived from three-helix bundles", Curr. Opin. Chem. Biol. 25, 65-70 (2015) (Apr. 2015).
Zarra, et al., "Molecular containers in complex chemical systems", Chem. Soc. Rev. 2015, 44 (2), 419-432 (Jan. 21, 2015).
Armstrong, M. J. et al. Liraglutide safety and efficacy in patients with non-alcoholic steatohepatitis (LEAN): a multicentre, double-blind, randomised, placebo-controlled phase 2 study. Lancet 387, 679-690, doi:10.1016/S0140-6736(15)00803-X (2016) (Nov. 19, 2015).
Drucker, D. The Cardiovascular Biology of Glucagon-like Peptide-1. Cell Metab. 24, 15-30 (2016) (Jul. 12, 2016).

(56) References Cited

OTHER PUBLICATIONS

Fagone, P. et al. Emerging therapeutic targets for the treatment of hepatic fibrosis. Drug Discov Today 21, 369-375, doi:10.1016/j.drudis.2015.10.015 (2016) (Feb. 2016).

Fosgerau, K. & Hoffmann, T. Peptide therapeutics: current status and future directions. Drug Discov. Today 20, 122-128 (2015) (Jan. 2015).

Gao, H. et al. The Glucagon-Like Peptide-1 Analogue Liraglutide Inhibits Oxidative Stress and Inflammatory Response in the Liver of Rats with Diet-Induced Non-alcoholic Fatty Liver Disease. Biol Pharm Bull 38, 694-702, doi:10.1248/bpb.b14-00505 (2015) (Feb. 16, 2015).

Gopalakrishnan, R., Frolov, A. I., Knerr, L., Drury, W. J. & Valeur, E. Therapeutic Potential of Foldamers: From Chemical Biology Tools to Drug Candidates? J. Med. Chem. 59, 9599-9621 (2016) (Jun. 30, 2016).

Hager, M. V., Johnson, L. M., Wootten, D., Sexton, P. M. & Gellman, S. H. β-Arrestin-Biased Agonists of the GLP-1 Receptor from β-Amino Acid Residue Incorporation into GLP-1 Analogues. J. Am. Chem. Soc. 138, 14970-14979 (2016) (Nov. 16, 2016).

Hanna, A., Connelly, K. A., Josse, R. G. & McIntyre, R. S. The non-glycemic effects of incretin therapies on cardiovascular outcomes, cognitive function and bone health. Expert Rev. Endocrinol. Metab. 10, 101-114 (2015) (Oct. 21, 2014).

Jazayeri, A. et al. Crystal structure of the GLP-1 receptor bound to a peptide agonist. Nature 546, 254-258(2017) (Jun. 8, 2017).

Jouihan, H. et al. Superior reductions in hepatic steatosis and fibrosis with co-administration of a glucagon-like peptide-1 receptor agonist and obeticholic acid in mice. Mol Metab 6, 1360-1370, doi:10.1016/j.molmet.2017.09.001 (2017) (Sep. 14, 2017).

Lau, J. et al. Discovery of the Once-Weekly Glucagon-Like Peptide-1 (GLP-1) Analogue Semaglutide. J. Med. Chem. 58, 7370-7380 (2015) (Aug. 26, 2015).

Madsbad, S. Review of head-to-head comparisons of glucagon-like peptide-1 receptor agonists. Diabetes Obes. Metab. 18, 317-332 (2016) (Apr. 2016).

Mauran, L., Kauffmann, B., Odaert, B. & Guichard, G. Stabilization of an α-helix by short adjacent accessory foldamers. Comptes Rendus Chim. 19, 123-131 (2016) (Jan. 14, 2016).

Maury, J., Le Bailly, B. A. F., Raftery, J. & Clayden, J. Conformational cooperativity between helical domains of differing geometry in oligoamide-oligourea foldamer chimeras. Chem Commun 51, 11802-11805 (2015) (Jun. 5, 2015).

McBrayer, D. N. & Tai-Gan, Y. Recent Advances in GLP-1 Receptor Agonists for Use in Diabetes Mellitus. Drug Dev Res 78, 292-299, doi:10.1002/ddr.21404 (2017) (Sep. 2017).

Pasco, M., Dolain, C. & Guichard, G. Foldamers in Medicinal Chemistry. in Comprehensive Supramolecular Chemistry II 89-125 (Elsevier, 2017) (Jun. 30, 2017) doi:10.1016/B978-0-12-409547-2.12565-X.

Potts, J. E. et al. The Effect of Glucagon-Like Peptide 1 Receptor Agonists on Weight Loss in Type 2 Diabetes: A Systematic Review and Mixed Treatment Comparison Meta-Analysis. PLOS ONE 10, e0126769 (2015) (Jun. 29, 2015).

Teyssières, E. et al. Proteolytically Stable Foldamer Mimics of Host-Defense Peptides with Protective Activities in a Murine Model of Bacterial Infection. J. Med. Chem. 59, 8221-8232 (2016) (Aug. 16, 2016).

Townsend, S. A. & Newsome, P. N. Review article: new treatments in non-alcoholic fatty liver disease. Aliment Pharmacol Ther 46, 494-507, doi:10.1111/apt.14210 (2017) (Jun. 8, 2017).

Valeur, E. et al. New Modalities for Challenging Targets in Drug Discovery. Angew. Chem. Int. Ed. 56, 10294-10323 (2017) (Aug. 21, 2017).

Wang, J., Yadav, V., Smart, A. L., Tajiri, S. & Basit, A. W. Toward Oral Delivery of Biopharmaceuticals: An Assessment of the Gastrointestinal Stability of 17 Peptide Drugs. Mol. Pharm. 12, 966-973 (2015) (Jan. 22, 2015).

Zhang, Y. et al. Cryo-EM structure of the activated GLP-1 receptor in complex with a G protein. Nature 546, 248-253 (2017) (Jun. 8, 2017).

International Search Report and Written Opinion for PCT/EP2019/076789, dated Feb. 4, 2020.

Fremaux, Juliette, et al., Peptide-oligourea hybrids analogue of GLP-1 with improved action in vivo, Nature Communications, vol. 10, No. 1, p. 924, Feb. 25, 2019 XP002796842, ISSN: 2041-1723.

Neff, L., et al., Emerging role of GLP-I receptor agonists in the treatment of obesity, Diabetes, Metabolic Syndrome and Obesity : Targets and Therapy, Jul. 20, 2010, 3:263-273; DOI: 10.2147/dmsott.s6816 PMID: 21437094 PMCID: PMC3047971.

Diao, L., et al., Pharmacokinetics and Pharmacokinetic—Pharmacodynamic Correlations of Therapeutic Peptides, Clin Pharmacokinet, 52:855-868; May 30, 2012.

* cited by examiner

IPGTT after 6h
1 ug/mouse (0.05 mg/kg)

IPGTT after 9h
1 ug/mouse (0.05 mg/kg)

FIG. 7

| | | | BW% | BG(AUC) (0-60 min) | BG(AUC) (0-120 min) | MI (pg/mL·min) |
|---|---|---|---|---|---|---|
| Ex-4* | | 0.10 | 129 | 136 | 129 | 20675 |
| | | 0.06 | 88 | 90 | | |
| URK-468 | | | 98 | 101 | 127 | 18270 |
| | | | 74 | 86 | 85 | 9355 |
| URK-434 | | 0.34 | 79 | 90 | | 14000 |
| | | 0.13 | 92 | 72 | 77 | 8793 |
| | | 0.13 | 98 | 55 | | 10000 |
| | | 1.00 | 79 | 80 | 103 | 14398 |
| URK-527 | | 0.21 | 105 | 98 | 103 | 14473 |
| | | 0.34 | 80 | 120 | 121 | 19830 | dosing: 1 ug / mouse i.v., IPGTT after 9 h of the dosing, healthy mice (C57Bl/6J)
mouse : 20 - 25 g, 0.04 -0.05 mg/kg, 10 -12 nmol/kg
* IPGTT after 6 h Compound 77

Compound 78

Compound 79

Compound 80

Compound 81

Compound 82

Compound 83

Compound 83 continued below $A^u$

γA $A^c$

PEPTIDE-OLIGOUREA FOLDAMER COMPOUNDS AND METHODS OF THEIR USE

CROSS-REFERENCE TO RELATED APPLICATION

This application claims the benefit of U.S. Provisional Application No. 62/324,414, filed 19 Apr. 2016, entitled: PEPTIDE-OLIGOUREA FOLDAMER COMPOUNDS AND METHODS OF THEIR USE, which is incorporated herein by reference in its entirety for all purposes.

INCORPORATION BY REFERENCE

In compliance with 37 C.F.R. § 1.52(e)(5), the sequence information contained in electronic file name: 1513195_130WO2_Sequence_Listing_ST25.txt; size 40.1 KB; created on: 21 Apr. 2017; using Patent-In 3.5, and Checker 4.4.0 is hereby incorporated herein by reference in its entirety.

FIELD OF THE INVENTION

The present description relates to peptide-based compounds, their synthesis, and use for treating diseases or disorders. In particular, the description provides compounds comprising a polypeptide portion, e.g., α-amino acid polypeptide, including or linked to a urea residue or multiple non-consecutive urea residues (e.g., amino acids having an N, N'-linked urea bridging unit).

BACKGROUND

Interactions between proteins and/or their substrates or ligands are critical for normal cell function, physiologic signal transduction, as well as for therapeutic intervention in many pathophysiologic or disease-related processes. Proteins and peptides are capable of adopting compact, well-ordered conformations, and performing complex chemical operations, e.g., catalysis, highly selective recognition, etc. The three dimensional structure is the principal determinant that governs specificity in protein-protein and/or protein-substrate interactions. Thus, the conformation of peptides and proteins is central for their biological function, pharmaceutical efficacy, and their therapeutic preparation.

Protein folding is inextricably linked to function in both proteins and peptides because the creation of an "active site" requires proper positioning of reactive groups. Consequently, there has been a long-felt need to identify synthetic polymer or oligomers, which display discrete and predictable (i.e., stable) folding and oligomerizing propensities (hereinafter referred to as "foldamers") to mimic natural biological systems. Insofar as these unnatural backbones are resistant to the action of proteases and peptidases, they are useful as probes having constrained conformational flexibility or as therapeutics with improved pharmacological properties, e.g., pharmacokinetic (PK) and/or pharmacodynamics (PD) features, such as potency and/or half-life. Whereas a naturally occurring polypeptide comprised entirely of α-amino acid residues will be readily degraded by any number of proteases and peptidases, foldamers, including chimeras of natural peptides and synthetic amino acid derivatives, mimetics or pseudopeptides, are not.

As noted above, the interest in foldamers stems in part from their resistance to enzymatic degradation. They are also interesting molecules because of their conformational behavior. The elucidation of foldamers having discrete conformational propensities akin to those of natural proteins has led to explorations of peptides constructed from β-, γ-, or δ-amino acids. γ-Peptides containing residues bearing γ-substitution or α, γ-disubstitution or α, β, γ-trisubstitution have been shown to adopt a helical conformation defined by a 14-member turn that is stabilized by $C=O_{(i)} \rightarrow NH_{(i+3)}$ hydrogen bonds (see FIGS. 1A and 1B). Both the $3_{14}$ and $2.5_{12}$ helical backbones have been found suitable for the design of stabilized helical peptides useful for therapeutic purposes. For example, in order to cluster polar residues on one face of the helix, amphiphilic $3_{14}$-helical β-peptides have been constructed from hydrophobic-cationic-hydrophobic- or hydrophobic-hydrophobic-cationic residue triads.

Despite many structure-activity studies, lead optimization remains challenging because sequence modifications of α-peptides generally affect several parameters at the same time. Accordingly, a need persists in the art for therapeutic peptides with improved properties.

SUMMARY

The present description relates to the surprising and unexpected discovery that α-peptide/modified or peptidomimetic compounds, i.e., compounds having a natural or alpha amino acid (poly)peptide having at least one urea amino acid substitution has enhanced or improved properties relative to the parental or cognate "natural" peptide. In particular, the description provides peptide compounds or foldamers comprising a portion or sequence of alpha amino acids (i.e., an "α-peptide") including a urea amino acid residue, e.g., a 1,2-ethylene diamine residue having an N, N'-linked urea bridging unit, and including compounds or foldamers having a plurality of non-consecutive urea amino acid residue substitutions, e.g., a 1,2-ethylene diamine residue having an N, N'-linked urea bridging unit. As such, the present description provides α-peptide/oligourea compounds, methods of making, and using the same.

Amino acid ureas represent interesting classes of peptidomimetic foldamers that have previously received little attention. The compounds as described herein improve at least one pharmacokinetic (PK) and/or pharmacodynamics (PD) characteristics of the natural peptide. Because the compounds as described herein can adopt desired secondary structures similar to native peptides, including, e.g., linear, cyclic or helicoidal structures, they can serve as, for example, receptor ligands, effector molecules, agonists, antagonists, modulators of protein-protein interactions, organocatalysts or enzymes.

In one aspect, the description provides peptide-oligourea compounds that comprise at least one substitution of an α-amino acid of the parent peptide sequence with an urea amino acid residue. In certain embodiments, the compound comprises a plurality of substitutions. In other embodiments, the plurality of substitutions includes at least one on-consecutive, monosubstitution.

In any aspect or embodiment described herein, the oligourea residue is substituted with an identical or homologous (i.e., conservative change) proteinogenic amino acid side chain.

In additional aspects, the description provides peptide-oligourea compounds in which a plurality of non-consecutive α-amino acids of the parent peptide sequence are substituted with a urea amino acid residue.

In a further aspect, the description provides peptide-oligourea compound (e.g. a foldamer) comprising a plurality of amino acids substitution with a residue selected from an urea (e.g., substituted or unsubstituted N-2-aminoethylcarbamoyl residue), a thiourea (e.g., substitute or unsubstituted N-(2-aminoethyl)carbamothioyl), and a guanidine (e.g., substitute or unsubstituted N-(2-aminoethyl)formamidinyl), wherein at least one non-consecutive amino acid has been monosubstituted by an aminourea, a thiourea, or a guanidine.

In any aspect or embodiment described herein, the substitution or substitutes can be located anywhere within the parental polypeptide or peptidomimetic chain. Thus, the urea amino acid residue or residues are coupled, joined to or contiguous with the α-peptide amino acid backbone. In certain embodiments, the urea amino acid residues are "fused" to a terminus, e.g., amino terminus, carboxy terminus or both, of the peptide (e.g., an α-amino acid peptide) or peptidomimetic. In certain embodiments, the urea amino acid residues are substituted with an identical or homologous (i.e., conservative change) proteinogenic amino acid side chain.

In any aspect or embodiment described herein, the substituted residue (e.g., the monosubstituted amino acid) is located in the first 4 amino acids (N-terminal) of the peptide or peptidomimetic.

In any aspect or embodiment described herein, the substituted residue (e.g., the monosubstituted amino acid) is located in the last 4 amino acids (C-terminal) of the peptide or peptidomimetic.

In any aspect or embodiment described herein, the substituted residue (e.g., the monosubstituted amino acid) is located at or within 3 amino acids of a peptidase degradation site of the peptide or peptidomimetic.

In any aspect or embodiment described herein, the substituted residue (e.g., the monosubstituted amino acid) is located at or within 3 amino acids of an amino acid that is key for the interaction between the protein and a receptor or protein that interacts with the natural/parent/native/unmodified protein.

In any aspect or embodiment described herein, the substituted residue (e.g., the monosubstituted amino acid) is located at or within 3 amino acids of an amino acid that is key for at least one pharmacokinetic property of the protein.

In any aspect or embodiment described herein, the substituted residue (e.g., the monosubstituted amino acid) is located at or within 3 amino acids of an amino acid that is key for at least one physical or biological property of the protein.

In any aspect or embodiment described herein, the substituted residue (e.g., the monosubstituted amino acid) wherein 3 or more amino acids have been substituted with a residue.

In any aspect or embodiment described herein, the peptide or peptidomimetic is 4 or more (e.g., 5, 6, 7, 8, 9, 10, or more) amino acids.

In any aspect or embodiment described herein, the peptide or peptidomimetic is a class B GPCR ligand or derivative thereof, such as lixisenatide, exenatide, liraglutide, albiglutide, dulaglutide, derivatives thereof, or combinations thereof.

In any aspect or embodiment described herein, the substation residue of the compound comprises a peptidomimetic urea residue, for example, a 1,2-ethylene diamine residue having an N, N'-linked urea bridging unit. In any aspect or embodiment described herein, the compound comprises at least one other modified or peptidomimetic amino acid residue, such as, an amino acid analog, e.g., one or more γ-amino acid residue, as well as other members of the γ-peptide superfamily including γ-peptides and oligocarbamates or a combination thereof. In certain embodiments, the at least one other modified or peptidomimetic amino acid residue is a N-(2-aminoethyl)carbamoyl residue, a substituted or unsubstituted N-(2-aminoethyl)carbamothioyl residue, a substituted or unsubstituted N-(2-aminoethyl)formamidinyl residue, a substituted or unsubstituted 2-aminoethanoxycarbonyl residue or a combination or oligomer thereof.

In any aspect or embodiment described herein, the peptide-oligourea comprises at least two non-consecutive modified or peptidomimetic amino acid residues having an N, N'-linked urea bridging unit. In any aspect or embodiment described herein, at least one of the modified or pseudoamino acid residues is a N-(2-aminoethyl)carbamoyl residue, a substituted or unsubstituted N-(2-aminoethyl)carbamothioyl residues, a substituted or unsubstituted N-(2-aminoethyl)formamidinyl residues, a substituted or unsubstituted 2-aminoethanoxycarbonyl residue or a combination thereof.

In certain aspects, the description provides urea amino acid-containing peptides that adopt stable secondary structures, including, e.g., linear, cyclic, or helicoidal, tertiary structure, and/or quaternary structures. In certain embodiments, the urea amino acid (i.e., peptidomimetic residue) includes a substituted or unsubstituted N-2-aminoethylcarbamoyl residue a γ-amino acid residue, a substituted and unsubstituted N-(2-aminoethyl)carbamothioyl residues, a substituted and unsubstituted N-(2-aminoethyl)formamidinyl residues, and a substituted and unsubstituted 2-aminoethanoxycarbonyl residues. In certain embodiments the peptide comprises two or more non-consecutive peptidomimetic residues. In additional embodiments, the urea amino acid is substituted with a proteinogenic amino acid side chain.

In certain aspects, the description provides compounds, as described herein, that are capable of binding specifically to a target, e.g., a protein such as a receptor, ligand or other polypeptide or peptide, or small molecule, similar to the native/natural/parent/unmodified peptide. In certain embodiments, the peptide-oligourea ligand compound comprises a peptide that includes a plurality of N, N'-linked urea N-2-aminoethyl residues as γ-amino acid residue analogues, wherein at least one of the residues is a non-consecutive, monosubstitution. In certain embodiments, the peptide comprises α-amino acids.

In any aspect or embodiment described herein, the peptide-oligourea ligand compound comprises an amino acid sequence contiguous with or coupled to one or more oligourea peptidomimetic residues, wherein the peptidomimetic residue is selected from the group consisting of substituted and unsubstituted N-2-aminoethylcarbamoyl residue, as well as isosteric residus, such as γ-amino acid residues, substituted and unsubstituted N-(2-aminoethyl) carbamothioyl residues, substituted and unsubstituted N-(2-aminoethyl)formamidinyl residues, and substituted and unsubstituted 2-aminoethanoxycarbonyl residues, and a combination thereof. In certain embodiments, the peptide-oligourea ligand compound comprises two or more urea peptidomimetic residues, wherein at least one urea peptidomimetic residue is not adjacent to another urea peptidomimetic residue (i.e., at least one peptidomimetic residue is non-consecutive with another peptidomimetic residue).

In additional embodiments, the urea amino acid or urea peptidomimetic residue comprises an acyclic γ-amino acid residue. In additional embodiments, the urea amino acid or urea peptidomimetic residue comprises an N-(2-aminoethyl) carbamoyl residue, acyclic γ-amino acid residue or a combination thereof. In any of the aspects or embodiments described herein, the urea amino acid or urea peptidomimetic residue comprises an isosteric residue such as γ-amino acid residue, substituted or unsubstituted N-(2-aminoethyl) carbamothioyl residue, substituted or unsubstituted N-(2-aminoethyl)formamidinyl residue, substituted or unsubstituted 2-aminoethanoxycarbonyl residue or a combination thereof.

In certain aspects, the description provides compounds comprising a peptide comprising at least one (e.g., at least 2, 3, or 4) non-consecutive urea amino acid or urea peptidomimetic residue comprising a N, N'-linked urea 1,2-ethylene diamine residue.

Surprisingly and unexpectedly, compounds as described herein comprising at least one urea or urea/γ-peptide or urea/oligocarbamate amino acid residues adopt well-defined helical secondary structures akin to that of α-polypeptides, and demonstrated enhanced or improved beneficial properties of the cognate or parental "natural" (i.e., native, unmodified, or parent) peptide.

In any of the embodiments described herein, the urea amino acid includes a peptidomimetic 1,2-ethylene diamine residue with N, N'-linked urea bridging unit. In a preferred embodiment, the peptidomimetic residue is a substituted or unsubstituted N-2-aminoethylcarbamoyl residue.

In any of the embodiments described herein, the compounds polypeptide includes at least one α-, γ-, δ-amino acid, derivative or combination thereof, which is contiguous with or coupled to one or multiple (e.g., at least 1, 2, 3, 4, 5, or 6) non-consecutive peptidomimetic 1,2-ethylene diamine residues having an N, N'-linked urea bridging unit. In a preferred embodiment, the peptide compound comprises a substituted or unsubstituted N-(2-aminoethyl)carbamoyl residue.

In any of the embodiments described herein, the compound comprises at least one non-consecutive urea amino acid or peptidomimetic residue (e.g., a monosubstituted urea amino acid or peptidomimetic residue) contiguous with or covalently linked or joined to at least one of the amino terminus (N'), the carboxyl terminus (C'), within the peptide sequence or a combination thereof. In certain embodiments, the compound comprises a plurality of urea amino acids or peptidomimetic residues.

In any aspect or embodiment described herein, the compound comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more carbamoyl or urea-substituted amino residues (e.g., amino acid derivatives with N, N'-linked urea bridging unit). In any aspect or embodiment described herein, the residue is at least one of a γ-amino acid residue, substituted or unsubstituted N-(2-aminoethyl)carbamothioyl residue, substituted or unsubstituted N-(2-aminoethyl)formamidinyl residue, substituted or unsubstituted 2-aminoethanoxycarbonyl residue or combination thereof. In a preferred embodiment, the urea amino acid is an substituted or unsubstituted N-(2-aminoethyl)carbamoyl residue. In certain embodiments, the aminoethylcarbamoyl residue is substituted with a proteinogenic amino acid side chain.

In any aspect or embodiment described herein, the compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In any aspect or embodiments described herein, the description provides pharmaceutically acceptable acid and base salt forms of the peptide-oligourea compounds described herein.

The foldamers as described herein including pharmaceutically acceptable salts thereof are useful for the preparation of a medicament and/or the treatment of disease in a subject. The compounds of the present disclosure may optionally be administered with at least one of a pharmaceutically acceptable excipient or carrier, pharmacologically active agent or a combination thereof. As such, in an additional aspect the present disclosure provides compositions comprising an effective amount of a compound as described herein, and a pharmaceutically acceptable carrier or excipient.

The description also provides methods of treating a disease or disorder or ameliorating the effects of the same comprising the steps of administering to an individual in need thereof, a composition comprising an effective amount of a compound or salt form thereof as described herein, and a pharmaceutically acceptable carrier or excipient, wherein the composition is effective for treating, preventing or ameliorating the effects of the disease or disorder.

In certain embodiments, the disease or disorder is selected from the group consisting of diabetes (such as diabetes mellitus type 1 or diabetes mellitus type 2), a neurodegenerative disease or disorder (such as peripheral neuropathy, Alzheimer's disease, Parkinson's disease, Huntington's disease, amyotrophic sclerosis, multiple sclerosis, traumatic brain injury, or spinal cord injury), or a combination thereof.

In another aspect, the present description provides methods of making and using the compounds as described herein. For example, the compounds as described herein can be used as a diagnostic agent or a therapeutic agent for the treatment of a disease or condition.

In an additional aspect, the present description provides methods of making compounds as described herein. Thus, in one aspect, the present description provides for the synthesis of non-natural amino acids substituted by a wide range of functional R groups including proteinogenic side chains. In another aspect, the description provides compounds, which comprise non-natural oligourea amino acids (i.e., an amino acid having an N, N'-linked urea bridging unit) and/or peptoid versions of the same together with natural amino acids, wherein the modified peptides or foldamers form functional biopolymers.

In a further aspect, the present description provides a method of improving at least one biological property, such as therapeutic effect, of a peptide or a peptidomimetic, the method comprising: substituting a plurality of amino acids of the peptide or peptidomimetic with a residue selected from an aminourea, a thiourea, and a guanidine, wherein at least one non-consecutive amino acid has been monosubstituted by an aminourea, a thiourea, or a guanidine.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the present disclosure may be utilized in numerous combinations, all of which are expressly contemplated by the present description. These additional advantages objects and embodiments are expressly included within the scope of the present invention.

The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating some embodiments of the present disclosure and are not to be construed as limiting the invention. Further objects, features and advantages of the invention will become apparent from the following detailed description taken in conjunction with the accompanying figures showing illustrative embodiments of the invention, in which:

FIG. 3A shows the effect on blood glucose before and after IV treatment. FIG. 3B shows the effect on blood glucose before and after glucose load. FIG. 3C shows the area under the curve (AUC) for the same.

FIG. 4A shows the effect on blood glucose before and after IV treatment. FIG. 4B shows the effect on blood glucose before and after glucose load. FIG. 4C shows the area under the curve (AUC) for the same.

FIG. 5) and compound 66 (FIG. 6).

FIG. 7. Comparison of exemplary foldamers as described herein with exenatide. Several of the exemplary peptide foldamers as described herein demonstrate superior ability to reduce glucose.

FIG. 8A illustrates compound 77, FIG. 8B illustrates compound 78, FIG. 8C illustrates compound 79, FIG. 8D illustrates compound 80, FIG. 8E illustrates compound 81, FIG. 8F illustrates compound 82, and FIG. 8G illustrates compound 83.

DETAILED DESCRIPTION

Figure 1A:
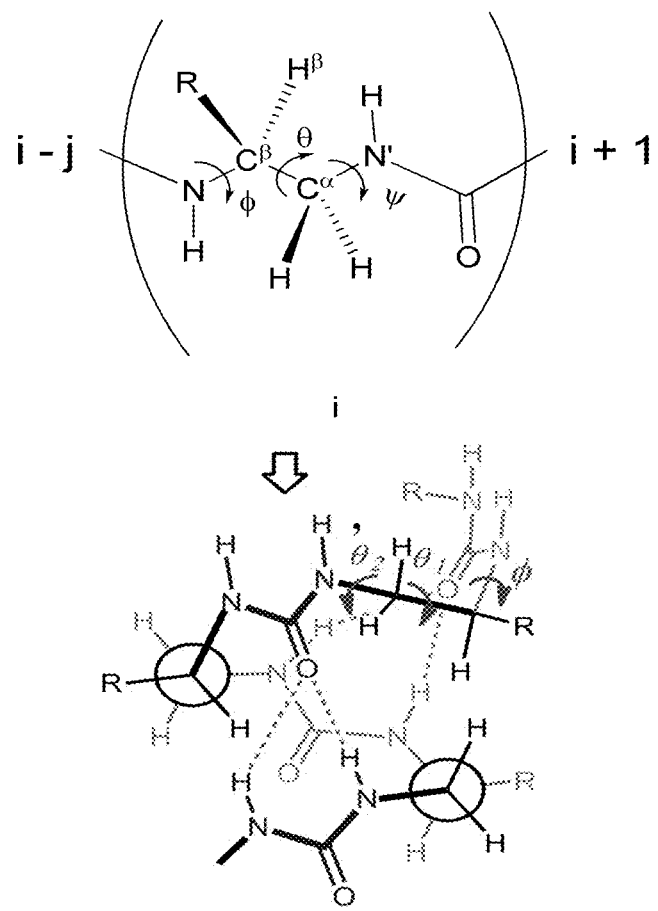
FIGS. 1A and 1B. (A) Covalent structure of an exemplary oligourea monomer (top) within a N,N'-linked oligourea (bottom). Backbone dihedral angles are marked by curved arrows. R denotes any proteinogenic amino acid side chain. (B) Formula and X-ray structure (right) of oligourea hexamer 1 and antibacterial oligourea octamer 1A.

The following is a detailed description of the present invention provided to aid those skilled in the art in practicing the present disclosure. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention of the present disclosure herein is for describing particular embodiments only and is not intended to be limiting of the invention. All publications, patent applications, patents, figures and other references mentioned herein are expressly incorporated by reference in their entirety. For example, U.S. patent application Ser. No. 14/465,680 filed: Aug. 21, 2014, titled: Peptide-Oligourea Chimeric Compounds and Methods of Their Use is hereby incorporated by reference in its entirety for all purposes.

In one aspect, the description provides peptide-oligourea compounds that comprise at least one substitution (e.g., at least 2, 3, 4, 5, 6, 7, 8, 9, 10, 11, 12, 113, 14, 15, 16, 17, 18, 19, or 20 substitutions) of an amino acid (e.g., an α-amino acid) of the parent peptide sequence with an oligourea residue (e.g., urea, thiourea, or guanidine). In any embodiment herein, at least one of the substitutions is a non-consecutive, monosubstitution. In certain embodiments, the oligourea residue is substituted with an identical or homologous (i.e., conservative change) proteinogenic amino acid side chain.

In additional aspects, the description provides peptide-oligourea compounds in which oligourea residues replace at least one amino acid in the carboxy terminus, amino terminus, in between the termini, or a combination thereof. Thus, the oligourea residues are coupled, joined to or contiguous with the α-peptide amino acid backbone with at least one of the substitutions being a non-consecutive, monosubstitution. In certain embodiments, the oligourea residues are "fused" to a terminus, e.g., amino terminus, carboxy terminus or both, of an α-amino acid peptide. In any aspect or embodiment described herein, the oligourea residues are substituted with an identical or homologous (i.e., conservative change) proteinogenic amino acid side chain. In any aspect or embodiment described herein, the substitution of an amino acid (e.g., an α-amino acid) of the parent peptide sequence includes at least one monosubstitution of non-consecutive amino acids with an urea residue as described herein (e.g., urea, thiourea, or guanidine)

In a further aspect, the description provides a peptide-oligourea compound (e.g. a foldamer) comprising a plurality of amino acids substitution with a residue selected from an urea (e.g., substituted or unsubstituted N-2-aminoethylcarbamoyl residue), a thiourea (e.g., substitute or unsubstituted N-(2-aminoethyl)carbamothioyl), and a guanidine (e.g., substitute or unsubstituted N-(2-aminoethyl)formamidinyl), wherein at least one non-consecutive amino acid has been monosubstituted by an aminourea, a thiourea, or a guanidine.

Aliphatic γ-peptides, i.e. oligoamides comprising some or all of γ-amino acid residues, represent an interesting class of peptidomimetic residues that have received little attention previously. Compared to α-amino acids, γ-amino acids are characterized by a greater chemical diversity (seven substitution positions versus three for α-amino acids) and conformational versatility. The γ-peptide backbone can be seen as the prototypic member of a larger family (i.e. γ-peptide superfamily or lineage) of peptidomimetic backbones and combinations thereof, all sharing an isosteric relationship (e.g. oligocarbamates, N,N'-linked oligo(thio)ureas, oligoguanidines, oligomers of β-aminoxy acids, sulfonamidopeptides). Although the constituent units in these backbones are endowed with different properties, their combination may represent an opportunity to generate new heterogeneous backbone oligomers with defined secondary structures, thus further expanding the chemical space of foldamers in the γ-peptide superfamily.

Within the γ-peptide superfamily, the constituent units of different backbones (i.e. amide (for γ-peptide), carbamate (for oligocarbamates) and urea (for oligourea) units) can be combined in various ways to generate new heterogeneous oligomers with well-defined helical secondary structures. For example, oligomers consisting of urea and carbamate or urea and amide linkages arranged in a 1:1 pattern adopt a helical conformation akin to that of urea homoligomers and γ-peptide foldamers. In this case, helix formation is mainly driven by the presence of the urea units whose propensity for folding surpasses that of amide and carbamate units.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects of the present disclosure, one or more of the present compounds described herein, are co-administered in combination with at least one additional bioactive agent. In particularly preferred aspects of the present disclosure, the co-administration of compounds results in synergistic activity and/or therapy.

"Peptides" are typically short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A polypeptide is a long, continuous, and unbranched peptide chain.

The term "amino" or "amine" as used herein refers to —NH2 and substituted derivatives thereof wherein one or both of the hydrogens are independently replaced with 20 substituents selected from the group consisting of alkyl, haloalkyl, fluoro alkyl, alkenyl, alkynyl, carbocyclyl, heterocyclyl, aryl, aralkyl, hetero aryl, hetero aralkyl, alkylcarbonyl, haloalkylcarbonyl, carbocyclylcarbonyl, fluoroalkylcarbonyl, alkenylcarbonyl, heterocyclylcarbonyl, arylcarbonyl, alkynylcarbonyl, aralkylcarbonyl, heteroarylcarbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

"Amino acid" refers to any molecule that contains both amino and carboxylic acid functional groups, and includes any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). The term is inclusive of various types of amino acids including α-, β-, γ-, or δ-amino acids, analogs and derivatives of the same, unless the context clearly indicates otherwise.

The term "amino acid sidechain" or "amino acid residue" shall mean, within context, a radical of a D- or L-amino acid sidechain (derived from an amino acid) which functions as a substituent on another group, often an alkylene (usually a methylene) group on R2' or R3' as otherwise described herein. Preferred amino acid sidechains for use in the present disclosure are derived from the sidechains of both natural and unnatural amino acids, preferably including, for example, alanine, β-alanine, arginine, asparagine, aspartic acid, cyclohexylalanine, cysteine, cystine, glutamic acid, glutamine, glycine, phenylalanine, histidine, isoleucine, lysine, leucine, methionine, naphthylalanine, norleucine, norvaline, proline, serine, threonine, valine, tryptophan or tyrosine, among others.

Unless the context clearly indicates otherwise, the term "any amino acid" can mean any natural or synthetic amino acid, including α-, β-, γ-, or δ-amino acids, possibly modified by the presence of one or more substituents, or combinations thereof, including analogs, derivatives, mimetics, and peptoid versions of the same. More precisely the term α-amino acid means an alpha aminated amino acid with the following general structure:

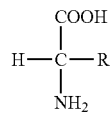

where R represents the side chain of the amino acid. In the context of the present disclosure, R therefore represents the side chain of a side or non-side amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the present disclosure, the amino acids used can therefore be natural or not. Namely, natural amino acids generally have the L configuration but also, an amino acid can have the L or D configuration. Moreover, R is of course not limited to the side chains of natural amino acid, but can be freely chosen.

As used herein, "urea" or carbamide is an organic compound with the chemical formula $CO(NH_2)_2$. The molecule has two —$NH_2$ groups joined by a carbonyl (C=O) functional group.

Unless indicated otherwise, the term "peptide precursor" or "parental peptide" refers, but is in no way limited to, a parental α-peptide sequence that is coupled with oligourea pseudopeptide or peptidomimetic subunits or substituting oligourea pseudopeptide subunits (i.e., exchanging one or more α-amino acids for one or more oligourea pseudopeptide subunits).

Unless indicated otherwise, the term "urea amino acid" or "urea peptidomimetic" refers, but is in no way limited to, a residue containing N, N'-linked urea residues including oligomers of substituted or unsubstituted N-2-ethylaminocarbamoyl or 1,2-ethylene diamine residues.

The term "compound" or "foldamer", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "amido" as used herein means an ammo group, as defined herein, appended to the parent molecular moiety through a carbonyl.

The term "cyano" as used herein means a —C≡N group.
The term "nitro" as used herein means a —N02 group.
The term "azido" as used herein means a —N3 group.

The abbreviations Me, Et, Ph, Tf, Nf, Ts, Ms, Cbz, and Boc represent methyl, ethyl, phenyl, trifluoromethanesulfonyl, nonafluorobutanesulfonyl, p-toluenesulfonyl, methanesulfonyl, carbobenzyloxy, and tert-butyloxycarbonyl, respectively.

A more comprehensive list of the abbreviations utilized by organic chemists of ordinary skill in the art appears in the first issue of each volume of the *Journal of Organic Chem-*

*istry*; this list is typically presented in a table entitled Standard List of Abbreviations, and is incorporated herein by reference.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms. The term "alkyl" shall mean within its context a linear, branch-chained or cyclic fully saturated hydrocarbon radical or alkyl group, preferably a C1-C10, more preferably a C1-C6, alternatively a C1-C3 alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present disclosure may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "Alkenyl" refers to linear, branch-chained or cyclic C2-C10 (preferably C2-C6) hydrocarbon radicals containing at least one C═C bond. The term "Alkynyl" refers to linear, branchchained or cyclic C2-C10 (preferably C2-C6) hydrocarbon radicals containing at least one C≡C bond.

The term "alkylene" when used, refers to a —(CH2)n-group (n is an integer generally from 0-6), which may be optionally substituted. When substituted, the alkylene group preferably is substituted on one or more of the methylene groups with a C1-C6 alkyl group (including a cyclopropyl group or a t-butyl group), more preferably a methyl group, but may also be substituted with one or more halo groups, preferably from 1 to 3 halo groups or one or two hydroxyl groups or O—(C1-C6 alkyl) groups. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene group may be substituted with an amino acid side chain such as group obtained from an amino acid (a natural or unnatural amino acid) such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes C0 means that carbon is absent and is replaced with H. Thus, a range of carbon atoms which is C0-C6 includes carbons atoms of 1, 2, 3, 4, 5 and 6 and for C0, H stands in place of carbon. The term "substituted" or "optionally substituted" shall mean independently (i.e., where more than substituent occurs, each substituent is independent of another substituent), one or more substituents (independently, up to five substituents, preferably up to three substituents, often 1 or 2 substituents on a moiety in a compound according to the present disclosure and may include substituents, which themselves may be further substituted) at a carbon (or nitrogen) position anywhere on a molecule within context, and independently includes as substituents hydroxyl, thiol, carboxyl, cyano (C≡N), nitro (NO2), halogen (preferably, 1, 2 or 3 halogens, especially on an alkyl, especially a methyl group such as a trifluoromethyl), an alkyl group (preferably, C1-C10, more preferably, C1-C6), aryl (especially phenyl and substituted phenyl for example benzyl or benzoyl), alkoxy group (preferably, C1-C6 alkyl or aryl, including phenyl and substituted phenyl), thioether (C1-C6 alkyl or aryl), acyl (preferably, C1-C6 acyl), ester or thioester (preferably, C1-C6 alkyl or aryl) including alkylene ester (such that attachment is on the alkylene group, rather than at the ester function which is preferably substituted with a C1-C6 alkyl or aryl group), preferably, C1-C6 alkyl or aryl, halogen (preferably, F or Cl), amine (including a five- or six-membered cyclic alkylene amine, further including a C1-C6 alkyl amine or a C1-C6 dialkyl amine which alkyl groups may be substituted with one or two hydroxyl groups) or an optionally substituted —N(C0-C6 alkyl)C(O)(O—C1-C6 alkyl) group (which may be optionally substituted with a polyethylene glycol chain to which is further bound an alkyl group containing a single halogen, preferably chlorine substituent), hydrazine, amido, which is preferably substituted with one or two C1-C6 alkyl groups (including a carboxamide which is optionally substituted with one or two C1-C6 alkyl groups), alkanol (preferably, C1-C6 alkyl or aryl), or alkanoic acid (preferably, C1-C6 alkyl or aryl).

The term "substituted" (each substituent being independent of another substituent) shall also mean within its context of use C1-C6 alkyl, C1-C6 alkoxy, halogen, amido, carboxamido, sulfone, including sulfonamide, keto, carboxy, C1-C6 ester (oxyester or carbonylester), C1-C6 keto, urethane —O—C(O)—NR1R2 or —N(R1)—C(O)—O—R1, nitro, cyano and amine (especially including a C1-C6 alkylene-NR1R2, a mono- or di-C1-C6 alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, ═O, —(CH2)m— (here, m and n are in context, 1, 2, 3, 4, 5 or 6), —S—, —S(O)—, SO2— or —NH—C(O)—NH—, —(CH2)nOH, —(CH2)nSH, —(CH2)nCOOH, C1-C6 alkyl, —(CH2)nO—(C1-C6 alkyl), —(CH2)nC(O)—(C1-C6 alkyl), —(CH2)nOC(O)—(C1-C6 alkyl), —(CH2)nC(O)O—(C1-C6 alkyl), —(CH2)nNHC(O)—R1, —(CH2)nC(O)—NR1R2, —(OCH2)nOH, —(CH2O)nCOOH, C1-C6 alkyl, —(OCH2)nO—(C1-C6 alkyl), —(CH2O)nC(O)—(C1-C6 alkyl), —(OCH2)nNHC(O)—R1, —(CH2O)nC(O)—NR1R2, —S(O)2—RS, —S(O)—RS (RS is C1-C6 alkyl or a —(CH2)m—NR1R2 group), NO2, CN or halogen (F, Cl, Br, I, preferably F or Cl), depending on the context of the use of the substituent. R1 and R2 are each, within context, H or a C1-C6 alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted C1-C6 alkyl groups (methyl, ethyl or hydroxymethyl or hydroxyethyl is preferred, thus providing a chiral center), an amido group as described hereinabove, or a urethane group O—C(O)—NR1R2 group where R1 and R2 are as otherwise described herein, although numerous other groups may also be used as substituents. Various optionally substituted moieties may be substituted independently with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

"Hydroxyl" refers the functional group —OH when it is a substituent in an organic compound.

"Heterocycle" refers to a heterocyclic group having from 4 to 9 carbon atoms and at least one heteroatom selected from the group consisting of N, O or S, and may be aromatic (heteroaryl) or non-aromatic. Thus, the heteroaryl moieties are subsumed under the definition of heterocycle, depending on the context of its use. Exemplary heteroaryl groups are described hereinabove. Exemplary nonaromatic heterocyclic groups for use in the present disclosure include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others.

Heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

"Heteroaryl" refers to a heterocyclic group having from 4 to 9 carbon atoms and at least one heteroatom selected from the group consisting of N, O or S with at least one ring of this group being aromatic. Heteroaryl groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

The term "thiol" refers to the group —SH.

The term "thioalkoxy" refers to the group —S-alkyl.

"Amidine" refers to a functional group that has two amine groups attached to the same carbon atom with one carbon-nitrogen double bond: HN=CR'—NH"2.

"Alkoxyl" refers to an alkyl group linked to oxygen thus: R—O—, where R is an alkyl.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Halogen" refers to fluorine, bromine, chlorine, and iodine atoms.

"Acyl" denotes the group —C(O)$R_e$, where $R_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend.

"Acyloxy" denotes the group —OAc, where Ac is an acyl, substituted acyl, heteroacyl or substituted heteroacyl whereas these generic groups have meanings which are identical with definitions of the corresponding groups as defined in this legend.

"Alkylamino" denotes the group —$NR_fR_g$, where $R_f$ and $R_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being a substituted (as otherwise described herein) or unsubstituted monovalent aromatic radical having a single ring (e.g., benzene, phenyl, benzyl) or condensed (fused) rings, wherein at least one ring is aromatic (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

"Cycloalkyl" refers to a monocyclic or polycyclic alkyl group containing 3 to 15 carbon atoms.

"Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P.

"Substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH═CH2), n-propenyl (—CH2CH═CH2), iso-propenyl (—C(CH3)═CH2), and the like.

"Imidazole" refers to a heterocyclic base of the general formula: $C_3H_4N_2$.

"Aralkyl group" refers to, for example, a C1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: $C(NH_2)_3$.

The term "receptor" is not limiting and includes any protein that interacts with the peptide (e.g., the natural or unmodified peptide), including receptors, ligands, etc.

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The present description describes the surprising and unexpected discovery that foldamers comprising peptide-oligourea compound (e.g., compounds having a polypeptide portion contiguous with or covalently coupled (i.e., "coupled") to oligomers of amino acid analogs having an N, N'-linked urea bridging unit; i.e., N-2-aminoethylcarbamoyl residues) demonstrate enhanced or improved properties (e.g., biological properties) relative to the parental or cognate "natural" peptide. The oligourea portion can also contain various combinations of isosteric residues such as γ-amino acid residues, substituted and unsubstituted N-(2-aminoethyl)carbamothioyl residues, substituted and unsubstituted N-(2-aminoethyl)formamidinyl residues, and substituted and unsubstituted 2-aminoethanoxycarbonyl residues. The foldamers or peptide-oligourea compounds as described herein improve at least one biological property, such as a PK and/or PD characteristic, of the natural peptide. Because the compounds of the present disclosure can adopt desired secondary structures similar to native peptides, including, e.g., linear, cyclic or helicoidal structures, they can serve as, for example, receptor ligands, effector molecules, agonists, antagonists, modulators of protein-protein interactions, organocatalysts or enzymes. Therefore, in certain aspects, the present description provides peptide-oligourea compounds, methods of making, and using the same.

Peptide-Oligourea Compounds

The present description relates to the surprising and unexpected discovery that α-peptide/modified or peptidomimetic compounds, i.e., compounds having a natural or alpha amino acid (poly)peptide portion including at least one (e.g., at least 2, 3, 4, 5, 6, 7, 8, 9, or 10) urea amino acid substitution demonstrates enhanced or improved properties relative to the parental or cognate "natural" peptide. In particular, the description provides peptide compounds or foldamers comprising a portion or sequence of alpha amino acids (i.e., an "α-peptide") that includes at least one (e.g., at least 2, 3, 4, 5, 6, 7, 8, 9, or 10) urea amino acid residue, e.g., a 1,2-ethylene diamine residue having an N, N'-linked urea bridging unit. The description also provides for a compound having a plurality (e.g., at least 2, 3, 4, 5, 6, 7, 8, 9, or 10) non-consecutive urea amino acid residues, e.g., a 1, 2-ethylene diamine residue having an N, N'-linked urea bridging unit. As such, the present description provides α-peptide/oligourea compounds, methods of making, and using the same.

Amino acid ureas represent interesting classes of peptidomimetic foldamers that have previously received little attention. The compounds as described herein improve at least one PK and/or PD characteristic of the natural peptide. Because the compounds as described herein can adopt desired secondary structures similar to native peptides, including, e.g., linear, cyclic or helicoidal structures, they can serve as, for example, receptor ligands, effector molecules, agonists, antagonists, modulators of protein-protein interactions, organocatalysts or enzymes.

In one aspect, the description provides peptide-oligourea compounds that comprise at least one substitution of an α-amino acid of the parent peptide sequence with a urea amino acid residue. In certain embodiments, the oligourea residue is substituted with an identical or homologous (i.e., conservative change) proteinogenic amino acid side chain.

In additional aspects, the description provides peptide-oligourea compounds in which a plurality of non-consecutive α-amino acids of the parent peptide sequence are substituted with a urea amino acid residue, a thiourea amino acid residue, or a guanidine amino acid residue. The substitutions can be located anywhere within the parental polypeptide chain. Thus, the urea amino acid residues are coupled, joined to or contiguous with the α-peptide amino acid backbone. In certain embodiments, the urea amino acid residue or residues are "fused" to a terminus, e.g., amino terminus, carboxy terminus or both, of an α-amino acid peptide. In certain embodiments, the urea amino acid residue or residues are substituted with an identical or homologous (i.e., conservative change) proteinogenic amino acid side chain.

In a further aspect, the description provides a peptide-oligourea compound or foldamer comprising a plurality of amino acids substitution to the parent peptide with a residue selected from a urea (e.g., substituted or unsubstituted N-2-aminoethylcarbamoyl residue), a thiourea (e.g., substitute or unsubstituted N-(2-aminoethyl)carbamothioyl), and a guanidine (e.g., substitute or unsubstituted N-(2-aminoethyl)formamidinyl), wherein at least one non-consecutive amino acid has been monosubstituted by an aminourea, a thiourea, or a guanidine.

In any aspect or embodiment described herein, the substituted residue (e.g., the monosubstituted amino acid) is located in the first 4 amino acids (N-terminal) of the peptide (e.g., the first amino acid (N-terminal), second amino acid, third amino acid, or fourth amino acid of the peptide).

In any aspect or embodiment described herein, the substituted residue (e.g., the monosubstituted amino acid) is located in the last 4 amino acids (C-terminal) of the peptide (e.g., the last amino acid (C-terminal), the second to last amino acid, the third to last amino acid, or fourth to last amino acid of the peptide).

In any aspect or embodiment described herein, the substituted residue (e.g., the monosubstituted amino acid) is located at or within 3 amino acids of a peptidase degradation site of the peptide (e.g., within 2 amino acids or within 1 amino acid of a peptidase degradation site of the peptide).

In any aspect or embodiment described herein, the substituted residue (e.g., the monosubstituted amino acid) is located at or within 3 amino acids of an amino acid that is key for the interaction between the protein and a receptor, ligand or other polypeptide or peptide that interacts with the natural/native peptide (e.g., within 2 amino acids or within 1 amino acid of an amino acid that is key for the interaction between the protein and a receptor, ligand or other polypeptide or peptide that interacts with the peptide).

In any aspect or embodiment described herein, the substituted residue (e.g., the monosubstituted amino acid) is located at or within 3 amino acids of an amino acid that is key for at least one pharmacokinetic property of the peptide (e.g., within 2 amino acids or within 1 amino acid of an amino acid that is key for at least one pharmacokinetic property of the peptide).

In any aspect or embodiment described herein, the substituted residue (e.g., the monosubstituted amino acid) is located at or within 3 amino acids of an amino acid that is key for at least one physical property of the peptide (e.g., within 2 amino acids or within 1 amino acid of an amino acid that is key for at least one physical property of the peptide).

In any aspect or embodiment described herein, the substituted residue (e.g., the monosubstituted amino acid) wherein 3 or more amino acids have been substituted with a residue. In any aspect or embodiment described herein, the peptide is 4 or more amino acids (e.g., at least 4, 5, 6, 7, 8, 9, 10, 11, 12, 13, 14, 15, 16, 17, 18, 19, or 20 amino acids). In any aspect or embodiment described herein, the number of amino acids of the parent peptide is equal to or less than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 125, 150, 175, 200, 250, 300, 350, 400, 450, 500 amino acids.

In any aspect or embodiment described herein, the urea portion of the compound comprises at least one (e.g., at least 2, 3, 4, 5, 6, 7, 8, 9, 10, 11, 12, 13, 14, or 15) peptidomimetic urea residue as described herein, for example, a 1,2-ethylene diamine residue having an N, N'-linked urea bridging unit. In certain embodiments, the peptidomimetic oligourea portion further comprises at least one other modified or peptidomimetic amino acid residue, such as, an amino acid analog, e.g., one or more γ-amino acid residue, as well as other members of the γ-peptide superfamily including γ-peptides and oligocarbamates or a combination thereof. In certain embodiments, the at least one other modified or peptidomimetic amino acid residue is a N-(2-aminoethyl) carbamoyl residue, a substituted or unsubstituted N-(2-aminoethyl)carbamothioyl residue, a substituted or unsubstituted N-(2-aminoethyl)formamidinyl residue, a substituted or unsubstituted 2-aminoethanoxycarbonyl residue or a combination or oligomer thereof.

In certain embodiments, the peptide-oligourea, foldamer, or compound of the present disclosure is capable of binding specifically to a target, e.g., a protein such as a receptor or other polypeptide or peptide, or small molecule, similar to the natural peptide.

In any aspect or embodiments described herein, the peptide comprises at least two (e.g., at least 3, 4, 5, 6, 7, 8, 9, or 10) non-consecutive urea amino acids or urea peptidomimetic amino acid residues, or modified versions thereof, having an N, N'-linked urea bridging unit. In certain embodiments, at least one of the modified or pseudoamino acid residues is a N-(2-aminoethyl)carbamoyl residue, a substituted or unsubstituted N-(2-aminoethyl)carbamothioyl residues, a substituted or unsubstituted N-(2-aminoethyl)formamidinyl residues, a substituted or unsubstituted 2-aminoethanoxycarbonyl residue or a combination thereof.

In certain aspects, the description provides urea amino acid-containing peptides that adopt stable secondary structures, including, e.g., linear, cyclic, or helicoidal, tertiary structure, and/or quaternary structures. In certain embodiments, the urea amino acid (i.e., peptidomimetic residue) includes a substituted or unsubstituted N-2-aminoethylcarbamoyl residue a γ-amino acid residue, a substituted and unsubstituted N-(2-aminoethyl)carbamothioyl residues, a substituted and unsubstituted N-(2-aminoethyl)formamidinyl residues, and a substituted and unsubstituted 2-aminoethanoxycarbonyl residues. In certain embodiments the peptide comprises two or more non-consecutive peptidomimetic residues. In any aspect or embodiment described herein, the urea amino acid is substituted with a proteinogenic amino acid side chain.

In certain aspects, compounds according to the present disclosure are capable of binding specifically to a target, e.g., a protein such as a receptor, ligand or other polypeptide or peptide, or small molecule, similar to the native or natural peptide. In certain embodiments, the peptide-oligourea ligand compound comprises a peptide comprising a plurality of N, N'-linked urea N-2-aminoethyl residues as γ-amino acid residue analogues. In certain embodiments, the peptide portion comprises α-amino acids. In an additional embodiments, the peptide-oligourea ligand compound comprises an amino acid sequence contiguous with or coupled to an oligourea portion including one or more oligourea peptidomimetic residues, wherein the peptidomimetic residue is selected from the group consisting of substituted and unsubstituted N-2-aminoethylcarbamoyl residue as well as isosteric residus such as γ-amino acid residues, substituted and unsubstituted N-(2-aminoethyl)carbamothioyl residues, substituted and unsubstituted N-(2-aminoethyl)formamidinyl residues, and substituted and unsubstituted 2-aminoethanoxycarbonyl residues, and a combination thereof. In certain embodiments, the peptide-oligourea ligand compound comprises two or more (e.g., at least 2, 3, 4, 5, 6, 7, 8, 9, or 10) urea peptidomimetic residues, wherein at least one (e.g., at least 1, 2, 3, 4, 5, 6, 7, 8, 9, or 10) urea peptidomimetic residue is a non-consecutive substitution.

In any aspect or embodiment described herein, the urea amino acid or urea peptidomimetic residue comprises an acyclic γ-amino acid residue. In any aspect or embodiment described herein, the urea amino acid or urea peptidomimetic residue comprises an N-(2-aminoethyl)carbamoyl residue, acyclic γ-amino acid residue or a combination thereof. In any of the embodiments described herein, the urea amino acid or urea peptidomimetic residue comprises an isosteric residue such as γ-amino acid residue, substituted or unsubstituted N-(2-aminoethyl)carbamothioyl residue, substituted or unsubstituted N-(2-aminoethyl)formamidinyl residue, substituted or unsubstituted 2-aminoethanoxycarbonyl residue or a combination thereof.

In certain aspects, the description provides compounds comprising a peptide comprises one non-consecutive urea amino acid or urea peptidomimetic residue as described herein, e.g. a N, N'-linked urea 1,2-ethylene diamine residue.

It was surprising and unexpected that the compounds of the present disclosure that comprise ureas or urea/γ-peptide or urea/oligocarbamate amino acid residues adopt well-defined secondary structures akin to that of α-polypeptides, and has enhanced or improved beneficial properties relative to the cognate or parental "natural" peptide, e.g. resistance to peptidases and/or proteases, conformationally restrained, etc.

In any of the aspects or embodiments described herein, the urea amino acid includes a peptidomimetic 1,2-ethylene diamine residue with N, N'-linked urea bridging unit. In any of the embodiments described herein, the peptidomimetic is residue a substitute or unsubstituted N-2-aminoethylcarbamoyl residue.

In any of the embodiments described herein, the compounds comprise a polypeptide portion including at least one α-, γ-, δ-amino acid, derivative or combination thereof, which is contiguous with or coupled to a plurality of peptidomimetic 1,2-ethylene diamine residues having an N, N'-linked urea bridging unit, wherein at least one residue is non-consecutive with other peptidomimetic residues. In a preferred embodiment, the peptide compound comprises a substituted or unsubstituted N-(2-aminoethyl)carbamoyl residue.

In any of the embodiments described herein, the compound comprises an urea amino acid or peptidomimetic residue contiguous with or covalently linked or joined to at least one of the amino terminus (N'), the carboxyl terminus (C'), within the peptide sequence or a combination thereof.

In any of the embodiments described herein, the compound comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more carbamoyl or urea-substituted amino residues (e.g., amino acid derivatives with N, N'-linked urea bridging unit) with at least one non-consecutive carbamoyl or urea-substituted amino residue. In certain embodiments, the residue is at least one of or a plurality of a γ-amino acid residue, substituted or unsubstituted N-(2-aminoethyl)carbamothioyl residue, substituted or unsubstituted N-(2-aminoethyl)formamidinyl residue, substituted or unsubstituted 2-aminoethanoxycarbonyl residue or combination thereof. In a preferred embodiment, the urea amino acid is an substituted or unsubstituted N-(2-aminoethyl) carbamoyl residue. In certain embodiments, the aminoethylcarbamoyl residue is substituted with a proteinogenic amino acid side chain.

In any aspect or embodiment described herein, the compounds can further comprise at least one additional chemical modification. In certain embodiments, the chemical modification includes at least one of, for example, acetylation, phosphorylation, methylation, glycosylation, prenylation, isoprenylation, farnesylation, geranylation, pegylation, a disulfide bond, or combination thereof.

In an additional aspect, the description provides pharmaceutically acceptable acid and base salt forms of the peptide-oligourea compounds (i.e., the peptide-oligourea compounds or foldamers) described herein.

The foldamers as described herein including pharmaceutically acceptable salts thereof are useful for the preparation of a medicament and/or the treatment, prevention or amelioration of at least one symptom of a disease or disorder in a subject. The compounds of the present disclosure may optionally be administered with at least one of a pharmaceutically acceptable excipient, pharmacologically active agent or a combination thereof. As such, in an additional aspect the description provides compositions comprising an effective amount of a compound as described herein, and a pharmaceutically acceptable carrier or excipient.

In further embodiments, the compounds comprising at least one N, N'-linked urea residue (e.g., N-2-aminoethylcarbamoyl) of formula II:

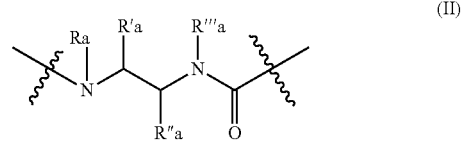

(II)

wherein Ra, R'a, R''a and R'''a are independently selected from the group consisting of a hydrogen atom, an amino acid side chain, a (C1-C10) alkyl, (C1-C10) alkenyl, (C1-C10) alkynyl, (C5-C12) monocyclic or bicyclic aryl, (C5-C14) monocyclic or bicyclic aralkyl, (C5-C14) monocyclic or bicyclic heteroalkyl and (C1-C10) monocyclic or bicyclic heteroaryl group comprising up to 5 heteroatoms selected from N, O, and S, said groups being able to be non-substituted or substituted by 1 to 6 substituents further selected from the group consisting of: a halogen atom, an $NO_2$, OH, amidine, benzamidine, imidazole, alkoxy, (C1-C4) alkyl, NH2, CN, trihalomethyl, (C1-C4) acyloxy, (C1-C4) monoalkylamino, (C1-C4) dialkylamino, guanidino group, bis alkylated and bis acylated guanido group.

In certain embodiments, $R_a$, $R'_a$, $R''_a$ and $R'''_a$ are independently selected from a chemical moiety described herein.

In certain embodiments, the N-2-aminoethylcarbamoyl residue is independently selected from the group consisting of:

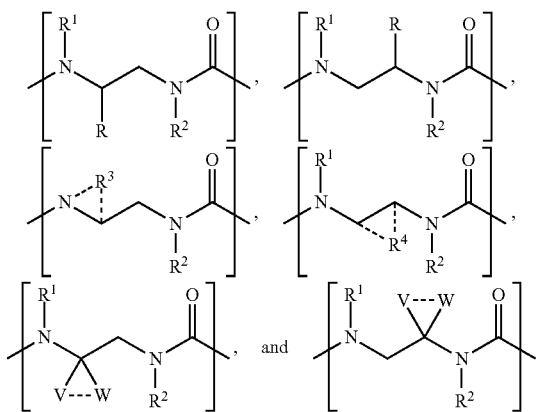

wherein R is independently selected from the group consisting of hydrogen, any side chain of a natural amino acid, linear, branched or cyclic C1-C6-alkyl, alkenyl or alkynyl; mono- or -bicyclic aryl, mono or bicyclic heteroaryl having up to five heteroatoms selected from N, O and S; mono or bicyclic aryl-C1-C6-alkyl, alkenyl or alkynyl; C1-C6-alkyloxy, aryloxy, heteroaryloxy, thio, C1-C6-alkylthio, amino, mono ordi-C1-C6-alkylamino, carboxylic acid, carboxamide mono- or di-C1-C6-alkylcarboxamine, sulfonamide, urea, mono-di or tri-substituted urea, thiourea, guanidine.

wherein $R^1$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S wherein $R^2$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S wherein $R^3$ together with the carbon and nitrogen atoms to which it is attached independently defines a substituted or unsubstituted, monocyclic or bicyclic C3-C10 heterocyclic ring having one or more N, O, or S atom(s) as the heteroatom(s); and substitutents on the heterocycle moiety are independently selected from the group consisting of linear, branched or cyclic C1-C6 alkyl, aralkyl, —O—C(O)—$NR^1R^2$ or —$N(R^1)$—C(O)—O—$R^1$, C1-C6 alkylene-$NR^1R^2$, —$(CH_2)_n$—NH—C(=$NR^1$)$NHR^2$, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, —$(CH_2)_n$O—(C1-C6 alkyl), —$(CH_2)_n$C(O)—(C1-C6 alkyl), —$(CH_2)_n$OC(O)—(C1-C6 alkyl), —$(CH_2)_n$C(O)O—(C1-C6 alkyl), —$(CH_2)_n$NHC(O)—$R^1$, —$(CH_2)_n$C(O)—$NR^1R^2$, —$(OCH_2)_n$OH, —$(OCH_2)_n$O—(C1-C6 alkyl), —$(CH_2O)_n$C(O)—(C1-C6 alkyl), —$(OCH_2)_n$NHC(O)—$R^1$, —$(CH_2O)_n$C(O)—$NR^1R^2$, —NO2, —CN, or -halogen.R1 and R2 are each, within context, H or a C1-C6 alkyl group.

wherein $R^4$ together with the carbon atoms to which it is attached independently defines a substituted or unsubstituted, monocyclic or bicyclic C3-C10 cycloalkyl, cycloalkenyl or heterocyclic ring having one or more N, O, or S atom(s) as the heteroatom(s); and substitutents on the cycloalkyl, cycloalkenyl or heterocycle moieties are independently selected from the group consisting of linear, branched or cyclic C1-C6 alkyl, aralkyl, —O—C(O)—$NR^1R^2$ or —$N(R^1)$—C(O)—O—$R^1$, C1-C6 alkylene-$NR^1R^2$, —$(CH_2)_n$—NH—C(=$NR^1$)$NHR^2$, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, —$(CH_2)_n$O—(C1-C6 alkyl), —$(CH_2)_n$C(O)—(C1-C6 alkyl), —$(CH_2)_n$OC(O)—(C1-C6 alkyl), —$(CH_2)_n$C(O)O—(C1-C6 alkyl), —$(CH_2)_n$NHC(O)—$R^1$, —$(CH_2)_n$C(O)—$NR^1R^2$, —$(OCH_2)_n$OH, —$(OCH_2)_n$O—(C1-C6 alkyl), —$(CH_2O)_n$C(O)—(C1-C6 alkyl), —$(OCH_2)_n$NHC(O)—$R^1$, —$(CH_2O)_n$C(O)—$NR^1R^2$, —NO2, —CN, or -halogen.R1 and R2 are each, within context, H or a C1-C6 alkyl group wherein V and W are combined, together with the carbon atoms to which they are bonded, and independently define a substituted or unsubstituted, monocyclic or bicyclic C3-C10 cycloalkyl, cycloalkenyl or heterocyclic ring having one or more N, O, or S atom(s) as the heteroatom(s).

In any of the compound embodiments described herein, the peptide portion may comprise an α-amino acid sequence corresponding to a biologically active peptide or a fragment thereof.

In still additional embodiments, the compound as described herein is biologically active, for example the compound has the same, similar, or better biological activity as the natural/parent peptide. For example, in certain embodiments, the compounds as described herein are enzymatically active. In still additional embodiments, the compounds as described herein are configured to bind target proteins. In certain embodiments the target protein is a cytosolic protein. In certain embodiments, the target protein is a membrane protein. In certain embodiments, the membrane protein is a receptor. In still additional embodiments, the receptor is a growth factor receptor or a G-Protein Coupled Receptor (GPCR) or a fragment thereof.

In certain aspects, the description provides compounds comprising a peptide sequence with a plurality of coupled urea amino acids comprising a N, N'-linked urea residues, wherein at least one of the urea amino acids is non-consecutive with other urea amino acids. Surprisingly and unexpectedly compounds as described herein adopt well-defined helical secondary structures akin to that of α-polypeptides, and can enhance or improve the beneficial properties of the cognate or parental "natural" peptide.

Compared to α-amino acids, γ-amino acids are characterized by a greater chemical diversity (seven substitution positions versus three for α-amino acids) and conformational versatility. The γ-peptide backbone can be seen as the prototypic member of a larger family (i.e. γ-peptide superfamily or lineage) of peptidomimetic backbones and combinations thereof, all sharing an isosteric relationship (e.g. oligocarbamates, N,N'-linked oligo(thio)ureas, oligoguanidines, oligomers of β-aminoxy acids, sulfonamidopeptides). Although the constituent units in these backbones are endowed with different properties, their combination represent an opportunity to generate new heterogeneous backbone oligomers with defined secondary structures, thus further expanding the chemical space of foldamers in the γ-peptide superfamily.

Pharmaceutical Forms

The compounds as described herein including pharmaceutically acceptable salts thereof are useful for the preparation of a medicament and/or the treatment of disease in a subject. In the case where a salt of a compound is desired and the compound is produced in the form of the desired salt, it can be subjected to purification as such. In the case where a compound is produced in the free state and its salt is desired, the compound is dissolved or suspended in a suitable organic solvent, followed by addition of an acid or a base to form a salt. As such, in an addition aspect the description provides compositions comprising an effective amount of a peptide-oligourea compounds as described herein, and a pharmaceutically acceptable carrier or excipient.

The compounds of the present disclosure may optionally be administered with at least one of a pharmaceutically acceptable excipient, pharmacologically active agent or a combination thereof. These novel, unnatural peptidomimetics are resistant or wholly immune to peptidase and protease degradation and are conformationally restrained. Thus, they are useful as tools to model peptide and protein conformations in aqueous solutions. The compounds are also useful as non-enzymatically degradable probes to mimic protein behavior in solution. As such, the description further provides the compositions comprising an effective amount of a peptide-oligourea compound as described herein, and a pharmaceutically acceptable carrier or excipient.

Certain compounds of the present disclosure and their salts may exist in more than one crystal form and the invention of the present disclosure includes each crystal form and mixtures thereof. Certain compounds of the present disclosure and their salts may also exist in the form of solvates, for example hydrates, and the invention of the present disclosure includes each solvate and mixtures thereof.

Certain compounds of the present disclosure may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present disclosure contains more than one chiral center, it may exist in diastereoisomeric forms. The diastereoisomeric compounds may be separated by methods known to those skilled in the art, for example chromatography or crystallization and the individual enantiomers may be separated as described above. The invention of the present disclosure includes each diastereoisomer of compounds of the present disclosure and mixtures thereof.

Certain compounds of the present disclosure may exist in different tautomeric forms or as different geometric isomers, and the invention of the present disclosure includes each tautomer and/or geometric isomer of compounds of the present disclosure and mixtures thereof.

Certain compounds of the present disclosure may exist in different stable conformational forms which may be separable. Torsional asymmetry due to restricted rotation about an asymmetric single bond, for example because of steric hindrance or ring strain, may permit separation of different conformers. The invention of the present disclosure includes each conformational isomer of compounds of the present disclosure and mixtures thereof.

Certain compounds of the present disclosure may exist in zwitterionic form and the invention of the present disclosure includes each zwitterionic form of compounds of the present disclosure and mixtures thereof.

The present disclosure encompasses all possible isomers including tautomers and mixtures thereof. Where chiral carbons lend themselves to two different enantiomers, both enantiomers are contemplated as well as procedures for separating the two enantiomers.

The present disclosure also relates to pharmaceutically acceptable salts, racemates, and optical isomers thereof. The compounds of the present disclosure typically contain one or more chiral centers. Accordingly, the present disclosure is intended to include racemic mixtures, diastereomers, enantiomers and mixture enriched in one or more stereoisomer. The scope of the invention of the present disclosure as described and claimed encompasses the racemic forms of the compounds as well as the individual enantiomers and non-racemic mixtures thereof.

Many of the compounds of the present disclosure may be provided as salts with pharmaceutically compatible counterions (i.e., pharmaceutically acceptable salts).

The term "pharmaceutically acceptable salt" is used throughout the specification to describe, where applicable, a salt form of one or more of the compounds or prodrugs described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure. In a preferred embodiment, the description provides pharmaceutically acceptable salts of the modified peptides as described herein, which retain the biological effectiveness and properties of the parent compounds and which are not biologically or otherwise harmful as the dosage administered. The compounds of present disclosure are capable of forming both acid and base salts by virtue of the presence of amino and carboxy groups respectively.

A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, parabromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, sub erate, sebacate, fumarate, maleate, butyne-I,4-dioate, hexyne-I,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, ~-hydroxybutyrate, glycolate, maleate, tartrate, methanesulfonate, propanesulfonate, naphthalene-I-sulfonate, naphthalene-2-sulfonate, mandelate and the like salts.

Preferred pharmaceutically acceptable acid addition salts include those formed with mineral acids such as hydrochloric acid and hydrobromic acid, and especially those formed with organic acids such as maleic acid. Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N (hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Prodrugs

The description also provides prodrug forms of the above described compounds, wherein the prodrug is metabolized in vivo to produce an analog or derivative as set forth above. Indeed, some of the described compounds may be a prodrug for another analog or derivative. The term "prodrug" is well understood in the art and refers to an agent which is converted into the parent drug in vivo by some physiological chemical process (e.g., a prodrug on being brought to the physiological pH is converted to the desired drug form). For example, see *Remington's Pharmaceutical Sciences,* 1980, vol. 16, Mack Publishing Company, Easton, Pa., 61 and 424.

Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present disclosure wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of the present disclosure include but are not limited to carboxylic acid substituents (e.g., —C(O)2H or a moiety that contains a carboxylic acid) wherein the free hydrogen is replaced by (C1-C4)alkyl, (Cz-C12)alkanoyloxymethyl, (C4-C9)1-(alkanoyloxy)ethyl, I-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, I-methyl-1-10 (alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-(C1-C2)alkylamino(C2-C3)alkyl (such as ~-dimethylaminoethyl), carbamoyl-(C1-C2)alkyl, N,N -die C1-C2)-alkylcarbamoyl-(C1-15 C2)alkyl and piperidino-, pyrrolidino- or morpholino(C2-C3)alkyl.

Other exemplary pro-drugs release an alcohol or amine of a compound of the present disclosure wherein the free hydrogen of a hydroxyl or amine substituent is replaced by (C1-C6)alkanoyloxymethyl, 1-((C1-C6)alkanoyloxy)ethyl, I-methyl-1-((C1-C6)alkanoyloxy)ethyl, (C1-C6)alkoxycarbonyl-oxymethyl, N-(C1-C6)alkoxycarbonylamino-20 methyl, succinoyl, (C1-C6)alkanoyl, a-amino(C1-C4)alkanoyl, arylactyl and a-aminoacyl, or a-aminoacyl-a-aminoacyl wherein said a-aminoacyl moieties are independently any of the naturally occurring L-amino acids found in proteins, —P(O)(OH)2'—P(O)(O(C1-C6)alkyl)2 or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective 30 Groups in Organic Synthesis, 2nd ed.; Wiley: New York, 1991). Protected forms of the inventive compounds are included within the scope of the present disclosure.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH3, —OAc). For example, an aldehyde or ketone group may be protected as an acetal or ketal, respectively, in which the carbonyl group (C(=O)) is converted to a diether (C(OR)2), by reaction with, for example, a primary alcohol. The aldehyde or ketone group is readily regenerated by hydrolysis using a large excess of water in the presence of acid. For example, an amine group may be protected, for example, as an amide (NRC(=O)R) or a urethane (—NRC(=O)OR), for example, as: a methyl amide (—NHC(=O)CH3); a benzyloxy amide (—NHC(=O)OCH2C6HsNHCbz); as a t-butoxy amide (NHC=(=O)OC(CH3)3, —NHBoc); a 2-biphenyl-2-propoxy amide (NHC(=O)OC(CH3) 2C6H4C6HsNHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide. For example, a thiol group may be protected as a thioether (—SR), for example, as: a benzyl thioether; or an acetamidomethyl ether (—SCH2NHC(=O)CH3). In at least certain examples, the compounds disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes, nematodes, and the like.

The term "pharmaceutically acceptable derivative" is used throughout the specification to describe any pharmaceutically acceptable prodrug form (such as an ester, amide other prodrug group) which, upon administration to a patient, provides directly or indirectly the present compound or an active metabolite of the present compound. The term "independently" is used herein to indicate that the variable, which is independently applied, varies independently from application to application.

The term "treatment" as used herein includes any treatment of a condition or disease in an animal, particularly a mammal, more particularly a human, and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or (iii) ameliorating or relieving the conditions caused by the disease, i.e. symptoms of the disease.

The term "effective" is used to describe an amount of a compound, composition or component which, when used within the context of its intended use, effects an intended result.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

Suitable routes for administration include oral, peroral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutic composition of the present disclosure comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present disclosure are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of convential dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, .beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length C8 to C12 from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinyl-pyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present disclosure that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this invention include hydroxyalkylcellulose, such as hydroxypropylcellulose and hydroxypropylmethyl-cellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of the present disclosure contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the present disclosure can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the present disclosure preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the present disclosure can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of the present disclosure can be coated with a controlled release polymer layer so as to provide additional controlled release properties. Suitable polymers that can be used to form this controlled release layer include the rate controlling polymers listed above.

As desired, the tablets, pellets or mini-tablets according to the present disclosure can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of the present disclosure may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethyl-cellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, N.sub.2 O, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

Methods of Treatment

The present disclosure also relates to a process or method for treatment of the disease states. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present disclosure is administered here for a body weight of about 70 kg.

Thus, in an aspect, the present disclosure provides a method of treating, preventing, or ameliorating at least one symptom of, a disease or disorder in a subject. The method comprising administering an effective amount of the peptide-oligourea compound or foldamer of the present disclosure or the pharmaceutical composition of the present disclosure to a subject in need thereof, wherein the peptide or pharmaceutical composition is effective for treating, preventing, or ameliorating at least one symptom of the disease or disorder.

The description provides methods of treating a disease or disorder or ameliorating the effects of the same comprising the steps of administering to an individual in need thereof, a composition comprising an effective amount of a compound as described herein, and a pharmaceutically acceptable carrier or excipient, wherein the composition is effective for treating, preventing or ameliorating the effects of the disease or disorder.

In any aspect or embodiment described herein, the parent (i.e., that "natural") peptide is a class B GPCR ligand or derivative thereof (e.g., lixisenatide, exenatide, liraglutide, albiglutide, dulaglutide, derivatives thereof, and combinations thereof).

In any aspect or embodiment described herein, the disease or disorder is selected from the group consisting of diabetes (such as diabetes mellitus type 1 or diabetes mellitus type 2), a neurodegenerative disease or disorder (such as peripheral neuropathy, Alzheimer's disease, Parkinson's disease, Huntington's disease, amyotrophic sclerosis, multiple sclerosis, traumatic brain injury, or spinal cord injury), or a combination thereof.

The compounds described above are used for the manufacture of a medication for use in the treatment of a disease, disorder or condition. The term "disease, disorder or condition" means, in the context of the present disclosure, any human or animal disease affecting one or more organs. Exemplary diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The peptide-oligourea compound can be used to treat autoimmune diseases, in particular those associated with inflammation, including, rheumatoid spondylitis, allergy, autoimmune diabetes, autoimmune uveitis.

The methods herein include administering to the subject (including a subject identified as in need of such treatment) an effective amount of a compound described herein, or a composition described herein to produce a desired effect. Identifying a subject in need of such treatment can be in the judgment of the subject or a health care professional and can be subjective (e.g., opinion) or objective (e.g., measurable by a test or diagnostic method). The therapeutic methods of the present disclosure, which include prophylactic treatment, in general comprise administration of a therapeutically effective amount of at least one of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In another aspect, the present description provides methods of making and using the compounds as described herein. For example, the compounds as described herein can be used as a diagnostic agent or a therapeutic agent for the treatment of a disease or condition.

In one embodiment, the present disclosure provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with protein-expression related disease (including misfolding), in which the subject has been administered a therapeutic amount of a compound herein sufficient to treat the disease, disorder, condition, or symptoms thereof. The level of Marker determined in the method can be compared to known levels of Marker in either healthy normal controls or in other afflicted patients to establish the subject's disease status. In certain embodiments, a second level of Marker in the subject is determined at a time point later than the determination of the first level, and the two levels are compared to monitor the course of disease or the efficacy of the therapy. In certain embodiments, a pre-treatment level of Marker in the subject is determined prior to beginning treatment according to the present disclosure; this pre-treatment level of Marker can then be compared to the level of Marker in the subject after the treatment commences, to determine the efficacy of the treatment.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound may be conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient. The active ingredient is preferably administered to achieve peak plasma concentrations of the active compound of about 0.00001-30 mM, preferably about 0.1-30 µM.

This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent. The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Methods of Preparation

In another aspect, the present description provides methods of making and using the compounds of the present disclosure. For example, in one embodiment, the description provides a method of making a compound of the present disclosure comprising synthesizing an oligomer of residues comprising at least one or a plurality of N, N'-linked urea bridging unit, wherein the oligomer is coupled to at least one amino acid of a peptide backbone, wherein the peptide-oligourea compound has at least one non-consecutive urea amino acid in the backbone. For example, in an embodiment, the peptide does not have more than one consecutive urea amino acid in the backbone. In certain embodiments, the urea amino acid is an N-2-ethylaminocarbamoyl residue.

In certain embodiments, the description provides a method of synthesizing a compound comprising the steps of:
(a) selecting a biologically active polypeptide or biologically active fragment thereof having an amino acid sequence comprising at least two α-amino acid residues; and
(b) fabricating a synthetic oligomer wherein:
  (i) at least one (e.g., a plurality) of α-amino acid residues in the biologically active polypeptide or fragment of step (a) are replaced by m urea amino acid residues selected from the group consisting of N-2-aminoethylcarbamoyl residues and acyclic γ-amino acid residues, and m is 1 or more, wherein at least one urea amino acid cannot be bound to another urea amino acid;

(ii) wherein 1 or more of the α-amino acid residues found in the conformation in the biologically active polypeptide or fragment of step (a) are replaced with residues selected from the group consisting of N-2-aminoethylcarbamoyl residues and acyclic γ-amino acid residues; and (iii) the synthetic polypeptide has a length of from about 5 or 6 residues to about 10, 20, 30, 40, 50, 60, 70, 80, 90, 100 or more residues (including intermediate values) and comprises at least 1 residue selected from the group consisting of N-2-aminoethylcarbamoyl residues and acyclic γ-amino acid residues.

In an additional aspect, the description provides methods of improving the pharmacologic effect of a peptide or peptidomimetic comprising, e.g., substituting one or more non-consecutive amino acids of the peptide or peptidomimetic with at least one residue selected from the group consisting of substituted or unsubstituted N-2-aminoethylcarbamoyl residue, γ-amino acid residue, substituted or unsubstituted N-(2-aminoethyl)carbamothioyl residues, substituted or unsubstituted N-(2-aminoethyl)formamidinyl residues, substituted or unsubstituted 2-aminoethanoxycarbonyl, and a combination thereof. In additional embodiments, the compound is a peptide or peptide derivative, analog or mimetic. In certain additional embodiments, the compound is an incretin or derivative thereof. In an embodiment, the incretin is selected from the group consisting of lixisenatide, exenatide, liraglutide, albiglutide, dulaglutide, and combinations thereof.

In a further aspect, the present disclosure provides a method of improving the pharmacologic effect of a peptide or a peptidomimetic. The method comprises: substituting a plurality of amino acids of the peptide or peptidomimetic with a residue selected from an aminourea, a thiourea, and a guanidine, wherein at least one non-consecutive amino acid has been monosubstituted by an aminourea, a thiourea, or a guanidine.

In any aspect or embodiment described herein, the peptide is at least one member selected from the group consisting of compound 2-13, 15, 17, 18, 20-65, 67-70, 72-81, and combinations thereof.

In certain embodiments, the peptide is a class B GPCR ligand or derivative thereof. For example, the class B GPCR ligand or derivative thereof may be selected from the group consisting of lixisenatide, lixisenatixe, exenatide, liraglutide, albiglutide, dulaglutide, derivatives thereof, and combinations thereof.

In certain embodiments, the peptide is a incretin or a derivative thereof. For example, the incretin or derivative thereof. For example the incretin or derivative thereof may be selected from the group consisting of lixisenatide, exenatide, liraglutide, albiglutide, dulaglutide, derivatives thereof, and combinations thereof.

Incretins are a group of metabolic hormones that stimulate a decrease in blood glucose levels. Incretins do so by causing an increase in the amount of insulin released from pancreatic beta cells of the islets of Langerhans after eating, before blood glucose levels become elevated. They also slow the rate of absorption of nutrients into the blood stream by reducing gastric emptying and may directly reduce food intake. They also inhibit glucagon release from the alpha cells of the islets of Langerhans.

The two main candidate molecules that fulfill criteria for an incretin are the intestinal peptides glucagon-like peptide-1 (GLP-1) and gastric inhibitory peptide (also known as glucose-dependent insulinotropic polypeptide or GIP). Both GLP-1 and GIP are rapidly inactivated by the enzyme dipeptidyl peptidase-4 (DPP-4); both GLP-1 and GIP are members of the glucagon peptide superfamily.

GLP-1 (7-36) amide is not very useful for treatment of type 2 diabetes mellitus, since it must be administered by continuous subcutaneous infusion. Several long-lasting analogs having insulinotropic activity have been developed, and three, exenatide (Byetta) and liraglutide (Victoza), plus exenatide extended-release (Bydureon), have been approved for use in the U.S. The main disadvantage of these GLP-1 analogs is they must be administered by subcutaneous injection. Exemplary GLP-1 analogs (Glucagon-like peptide-1 analogs ("incretin mimetics")) include lixisenatide (Lyxumia by Sanofi), exenatide (Byetta, Bydureon), liraglutide (Victoza), albiglutide (Tanzeum), and dulaglutide (by Lili).

Lixisenatide (trade name Lyxumia) is a once-daily injectable GLP-1 receptor agonist for the treatment of diabetes, discovered by Zealand Pharma A/S of Denmark and licensed and developed by Sanofi. Lixisenatide was accepted for review by the US FDA on Feb. 19, 2013, and approved by the European Commission on Feb. 1, 2013. On Sep. 12, 2013, Sanofi delayed the approval process in the US, citing internal data from a cardiovascular risk study. The drug will likely be resubmitted for approval in 2015.

Lixisenatide has been described as "des-38-proline-exendin-4 (Heloderma suspectum)-(1-39)-peptidylpenta-L-lysyl-L-lysinamide", meaning it is derived from the first 39 amino acids in the sequence of the peptide exendin-4, found in the Gila monster (*Heloderma suspectum*), omitting proline at position 38 and adding six lysine residues. Its complete sequence is: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2 (SEQ ID NO: 75).

Exenatide (marketed as Byetta, Bydureon) is a glucagon-like peptide-1 agonist (GLP-1 agonist) medication, belonging to the group of incretin mimetics, approved in April 2005 for the treatment of diabetes mellitus type 2. Exenatide in its Byetta form is administered as a subcutaneous injection (under the skin) of the abdomen, thigh, or arm, any time within the 60 minutes before the first and last meal of the day. A once-weekly injection has been approved as of Jan. 27, 2012 under the trademark Bydureon. It is manufactured by Amylin Pharmaceuticals and commercialized by Astra7eneca. Its sequence is: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-NH2 (SEQ ID NO: 76).

Exenatide is a synthetic version of exendin-4, a hormone found in the saliva of the Gila monster. It displays biological properties similar to human glucagon-like peptide-1 (GLP-1), a regulator of glucose metabolism and insulin secretion. According to the package insert, exenatide enhances glucose-dependent insulin secretion by the pancreatic beta-cell, suppresses inappropriately elevated glucagon secretion, and slows gastric emptying, although the mechanism of action is still under study.

Exenatide is a 39-amino-acid peptide, an insulin secretagogue, with glucoregulatory effects. Exenatide was approved by the FDA on Apr. 28, 2005 for patients whose diabetes was not well-controlled on other oral medication. The medication is injected subcutaneously twice per day using a filled pen-like device (Byetta), or on a weekly basis with either a pen-like device or conventional syringe (Bydureon).

The incretin hormones GLP-1 and glucose-dependent insulinotropic peptide (GIP) are produced by the L and K endocrine cells of the intestine following ingestion of food. GLP-1 and GIP stimulate insulin secretion from the beta cells of the islets of Langerhans in the pancreas. Only GLP-1 causes insulin secretion in the diabetic state; however, GLP-1 itself is ineffective as a clinical treatment for diabetes as it has a very short half-life in vivo. Exenatide bears a 50% amino acid homology to GLP-1 and it has a longer half-life in vivo. Thus, it was tested for its ability to stimulate insulin secretion and lower blood glucose in mammals, and was found to be effective in the diabetic state. In studies on rodents, it has also been shown to increase the number of beta cells in the pancreas.

Commercially, exenatide is produced by direct chemical synthesis. Historically, exenatide was discovered as Exendin-4, a protein naturally secreted in the saliva and concentrated in the tail of the Gila monster. Exendin-4 shares extensive homology and function with mammalian GLP-1, but has a therapeutic advantage in its resistance to degradation by DPP-IV (which breaks down GLP-1 in mammals) therefore allowing for a longer pharmacological half-life. The biochemical characteristics of Exendin-4 enabled consideration and development of exenatide as a diabetes mellitus treatment strategy. Given this history, exenatide is sometimes referred to as "lizard spit". Subsequent clinical testing led to the discovery of the also desirable glucagon and appetite-suppressant effects.

In its twice daily Byetta form, exenatide raises insulin levels quickly (within about ten minutes of administration) with the insulin levels subsiding substantially over the next hour or two. A dose taken after meals has a much smaller effect on blood sugar than one taken beforehand. The effects on blood sugar diminish after six to eight hours. In its Byetta form, the medicine is available in two doses: 5 mcg. and 10 mcg. Treatment often begins with the 5 mcg. dosage, which is increased if adverse effects are not significant. Its once weekly Bydureon form is unaffected by the time between the injection and when meals are taken. Bydureon has the advantage of providing 24-hour coverage for blood sugar lowering, while Byetta has the advantage of providing better control of the blood sugar spike that occurs right after eating. Per the FDA label for Bydureon, Bydureon lowers HbA1c blood sugar by an average of 1.6%, while Byetta lowers it by an average of 0.9%. Both Byetta and Bydureon have similar weight loss benefits. Per the FDA approved Bydureon label, the levels of nausea are lower for Bydureon patients than for Byetta patients.

According to the manufacturer, the autoinjector must be stored in a refrigerator between 2° C. (36° F.) and 8° C. (46° F.) before first use, and then at a temperature between 2° C. (36° F.) and 25° C. (77° F.). In hot weather, therefore, they should be refrigerated. Pens contain sixty doses designed to be used twice a day for 30 days. Exenatide received U.S. Pat. No. 5,424,286 which was filed May 24, 1993.

Exenatide is believed to facilitate glucose control in at least five ways: 1. Exenatide augments pancreas response (i.e. increases insulin secretion) in response to eating meals; the result is the release of a higher, more appropriate amount of insulin that helps lower the rise in blood sugar from eating. Once blood sugar levels decrease closer to normal values, the pancreas response to produce insulin is reduced; other drugs (like injectable insulin) are effective at lowering blood sugar, but can "overshoot" their target and cause blood sugar to become too low, resulting in the dangerous condition of hypoglycemia.

2. Exenatide also suppresses pancreatic release of glucagon in response to eating, which helps stop the liver from overproducing sugar when it is unneeded, which prevents hyperglycemia (high blood sugar levels).

3. Exenatide helps slow down gastric emptying and thus decreases the rate at which meal-derived glucose appears in the bloodstream.

4. Exenatide has a subtle yet prolonged effect to reduce appetite, promote satiety via hypothalamic receptors (different receptors than for amylin). Most people using exenatide slowly lose weight, and generally the greatest weight loss is achieved by people who are the most overweight at the beginning of exenatide therapy. Clinical trials have demonstrated the weight reducing effect continues at the same rate through 2.25 years of continued use. When separated into weight loss quartiles, the highest 25% experience substantial weight loss, and the lowest 25% experience no loss or small weight gain.

5. Exenatide reduces liver fat content. Fat accumulation in the liver or nonalcoholic fatty liver disease (NAFLD) is strongly related with several metabolic disorders, in particular low HDL cholesterol and high triglycerides, present in patients with type 2 diabetes. It became apparent that exenatide reduced liver fat in mice and more recently in man.

In an open-label, randomized, controlled trial of 551 patients, exenatide treatment for 26 weeks was associated with 2.3 kg weight loss; however, gastrointestinal symptoms were more common in the exenatide group, including nausea (57.1%), vomiting (17.4%) and diarrhea (8.5%).

Exenatide is approved "as adjunctive therapy to improve glycemic control in patients with type 2 diabetes mellitus who are taking metformin, a biguanide, or a combination of metformin and a sulfonylurea, but have not achieved adequate glycemic control." It has now been approved for use with thiazolidinediones such as pioglitazone. In 2011, Byetta was approved by the FDA for use as a substitute for mealtime insulin.

As an adjunctive therapy, exenatide is indicated to improve glycemic control in patients with type 2 diabetes who are taking metformin, a sulfonylurea, thiazolidinediones, or a combination of metformin and sulfonylurea or thiazolidinediones, but who have not been able to achieve adequate control of blood glucose.

Its use with insulin, meglitinides, and alpha-glucosidase inhibitors has not been studied. Some physicians are using exenatide as primary monotherapy, an indication approved by the FDA Oct. 30, 2009.

Liraglutide (NN2211) is a long-acting glucagon-like peptide-1 receptor agonist, binding to the same receptors as does the endogenous metabolic hormone GLP-1 that stimulates insulin secretion. Marketed under the brand name Victoza, it is an injectable drug developed by Novo Nordisk for the treatment of type 2 diabetes. In 2015, Novo Nordisk began marketing it in the U.S. under the brand name Saxenda as a treatment for obesity in adults with at least one weight-related comorbid condition.

The product was approved for treatment of type 2 diabetes by the European Medicines Agency (EMA) on Jul. 3, 2009, and by the U.S. Food and Drug Administration (FDA) on Jan. 25, 2010. More recently, Liraglutide was approved by the FDA on Dec. 23, 2014 for treatment for obesity in adults with some related comorbidity.

Liraglutide improves control of blood glucose. It reduces meal-related hyperglycemia (for 24 hours after administration) by increasing insulin secretion (only) when required by increasing glucose levels, delaying gastric emptying, and suppressing prandial glucagon secretion. In common to various degrees with other GLP-1 receptor agonists, liraglutide has advantages over more traditional therapies for type 2 diabetes: it acts in a glucose-dependent manner, meaning it will stimulate insulin secretion only when blood glucose levels are higher than normal, preventing "overshoot". Consequently, it shows negligible risk of hypoglycemia; it has the potential for inhibiting apoptosis and stimulating regeneration of beta cells (seen in animal studies); it decreases appetite and inhibits body weight gain, as shown in a head-to-head study versus glimepiride; and it lowers blood triglyceride levels.

Liraglutide is an acylated glucagon-like peptide-1 (GLP-1) agonist, derived from human GLP-1-(7-37), a less common form of endogenous GLP-1.

Liraglutide leads to insulin release in pancreatic beta cells in the presence of elevated blood glucose. This insulin secretion subsides as glucose concentrations decrease and approach euglycemia (normal blood glucose level). It also decreases glucagon secretion in a glucose-dependent manner and delays gastric emptying. Unlike endogenous GLP-1, liraglutide is stable against metabolic degradation by peptidases, with a plasma half-life of 13 hours.

Endogenous GLP-1 has a plasma half-life of 1.5-2 minutes due to degradation by the ubiquitous enzymes, dipeptidyl peptidase-4 (DPP4) and neutral endopeptidases (NEP). The half-life after intramuscular injection is approximately half an hour, so even administered this way, it has limited use as a therapeutic agent. The metabolically active forms of GLP-1 are the endogenous GLP-1-(7-36)$NH_2$ and the more rare GLP-1-(7-37). The prolonged action of liraglutide is achieved by attaching a fatty acid molecule at one position of the GLP-1-(7-37) molecule, enabling it to both self-associate and bind to albumin within the subcutaneous tissue and bloodstream. The active GLP-1 is then released from albumin at a slow, consistent rate. Albumin binding also results in slower degradation and reduced renal elimination compared to that of GLP-1-(7-37).

Albiglutide (tradenames Eperzan and Tanzeum) is a glucagon-like peptide-1 agonist (GLP-1 agonist) drug marketed by GlaxoSmithKline (GSK) for treatment of type 2 diabetes. It is a dipeptidyl peptidase-4-resistant glucagon-like peptide-1 dimer fused to human albumin. The drug was invented by Human Genome Sciences and was developed in collaboration with GSK. Albiglutide has a half-life of four to seven days, which is considerably longer than the other two GLP-1 analogs approved for market use, exenatide (Byetta) and liraglutide (Victoza).

Dulaglutide is a glucagon-like peptide 1 receptor agonist (GLP-1 agonist) for the treatment of type 2 diabetes that can be used once weekly. GLP-1 is a hormone that is involved in the normalization of level of glucose in blood (glycemia). The FDA approved dulaglutide for use in the United States in September 2014. The drug is manufactured by Eli Lilly under the brand name Trulicity.

Dulaglutide binds to glucagon-like peptide 1 receptors, slowing gastric emptying and increases insulin secretion by pancreatic Beta cells. Simultaneously the compound reduces the elevated glucagon secretion by inhibiting alpha cells of the pancreas, which is known to be inappropriate in the diabetic patient. GLP-1 is normally secreted by L cells of the gastrointestinal mucosa in response to a meal.

The compound is indicated for adults with type 2 diabetes mellitus as an adjunct to diet and exercise to improve glycemic control. Dulaglutide is not indicated in the treatment of subjects with type 1 diabetes mellitus or patients with diabetic ketoacidosis. Dulaglutide can be used either stand-alone or in combination with other medicines for type 2 diabetes, in particular metformin, sulfonylureas, thiazolidinediones, and insulin taken concomitantly with meals.

Additional, exemplary methods for performing the synthesis of compounds of the present disclosure are provided below.

It is understood that the examples and embodiments described herein are for illustrative purposes only and that various substitutions, modifications or changes in light thereof will be suggested to persons skilled in the art and are included within the spirit and purview of this application and are considered within the scope of the appended claims. The following examples are given by way of example of the preferred embodiments, and are in no way considered to be limiting to the invention. For example, the relative quantities of the ingredients may be varied to achieve different desired effects, additional ingredients may be added, and/or similar ingredients may be substituted for one or more of the ingredients described. All publications, patents, and patent applications cited herein are hereby incorporated by reference in their entirety for all purposes.

EXAMPLES

As the inventors have shown previously, oligomeric backbones consisting of N,N'-linked urea bridging units (see FIG. 1A) possess a remarkable propensity to fold into helical secondary structures in organic solvents and showed promise for interaction with biologically relevant targets. Compared to alpha-peptides, helix stabilization in oligoureas is promoted by the presence of additional backbone conformational restriction and H-bond donor sites. In particular, three-centered H-bonding between $C=O_{(i)}$ and urea $HN_{(i3)}$ and $HN'_{(i2)}$ has been characterized in solution by NMR spectroscopy and circular dichroism in organic solvents as well as in aqueous environment as well as in the solid-state by X-ray crystallography. For a review, see: L. Fischer, G. Guichard, Org. Biomol. Chem. 2010, 8, 3101-3117. See also original articles: V. Semetey, D. Rognan, C. Hemmerlin, R. Graff, J.-P. Briand, M. Marraud, G. Guichard, *Angew. Chem. Int. Ed.* 2002, 41, 1893-1895; A. Violette, M. C. Averlant-Petit, V. Semetey, C. Hemmerlin, R. Casimir, R. Graff, M. Marraud, J.-P. Briand, D. Rognan, G. Guichard, J. Am. Chem. Soc. 2005, 127, 2156-2164.

Figure 1B:
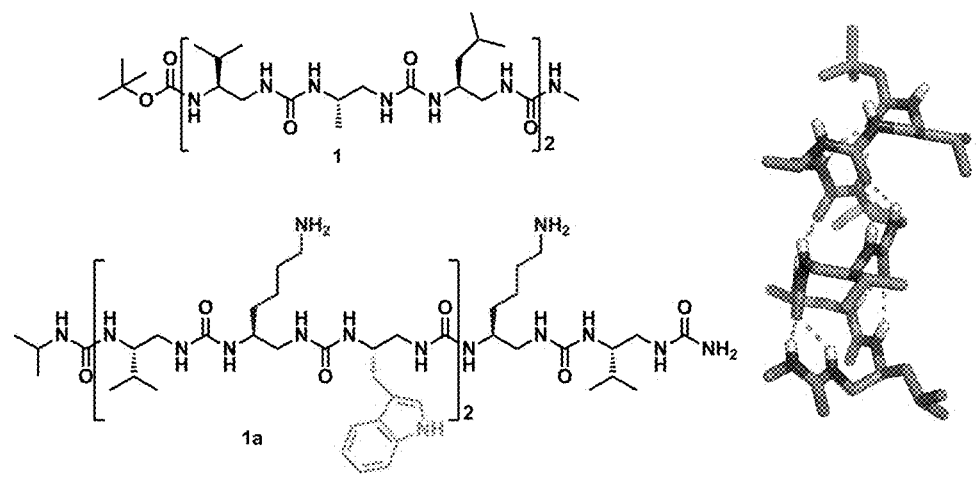

A representative oligourea with antimicrobial properties (compound 1a, FIG. 1B) is also shown to illustrate the diversity of side chains that is accessible in oligoureas. In addition compound 1a has been found to maintain a helical conformation in aqueous environment illustrating the potential of oligoureas as bioactive compounds. See: P. Claudon, A. Violette, K. Lamour, M. Decossas, S. Fournel, B. Heurtault, J. Godet, Y. Mély, B. Jamart-Grégoire, M.-C. Averlant-Petit, J.-P. Briand, G. Duportail, H. Monteil, G. Guichard, *Angew. Chem.* Int. Ed. Engl. 2010, 49, 333-336)2.

As mentioned above, the inventors have previously demonstrated (see, e.g. U.S. Patent Application Publication No. 2015/0141323 A1) that chimeric foldamers (compounds having a polypeptide portion contiguous with or linked to oligomers of amino acids having an N, N'-linked urea bridging unit) demonstrate enhanced or improved properties relative to the parental or cognate "natural" peptide. The chimeric compounds previously described have regular and persistent helical conformations and improved helix stability. Because the previously described chimeric foldamers can adopt desired secondary structures similar to native peptides, including, e.g., linear, cyclic or helicoidal structures, the inventors decided to examine if non-consecutive substitutions could be used to prepare peptide-oligourea compounds that could serve as, for example, receptor ligands, effector molecules, agonists, antagonists, modulators of protein-protein interactions, organocatalysts or enzymes.

It was surprising and unexpected that non-consecutive oligourea substitutions could effectively improve biological properties of a peptide or peptidomimetic, such as therapeutic effect, stability toward enzymatic degradation, stability, solubility, affinity for a receptor, ligand or other polypeptide or peptide that interacts with the peptide (e.g., the natural or native peptide), and/or clearance.

Figure 2:
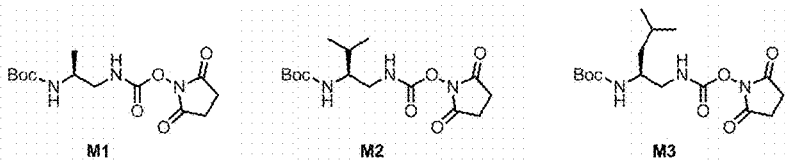
FIG. 2. Chemical formulae of N-Boc protected activated monomers M1-M3.

Synthesis of Peptide-Oligourea Compounds. General synthetic approaches to N-Boc protected activated succinimidyl carbamate monomers for use in the synthesis of peptide-oligourea compounds of the present disclosure (M1-M3, see FIG. 2) has been described in C. Aisenbrey, N. Pendem, G. Guichard, B. Bechinger, Org. Biomol. Chem. 2012, 10, 1440-1447. and in G. Guichard, V. Semetey, C. Didierjean, A. Aubry, J.-P. Briand, M. Rodriguez, J. Org. Chem. 1999, 64, 8702-8705. Oligoureas can be derived from building blocks with any desired amino acid side chain.

Briefly, The N-protected α-amino acid was dissolved in anhydrous THF under $N_2$ and cooled to −10° C. After addition of NMM (1.1 eq) and IBCF (1.0 eq), the mixture was stirred at −10° C. for 45 min. The precipitated N-methylmorpholine hydrochloride was removed by filtration and washed with THF. The filtrate and washings were combined in a flask. At 0° C., a solution of $NaBH_4$ (2.00 eq) in water was added and the resulting solution was stirred at room temperature overnight. The THF was removed under vacuum and the residue was quenched with an aqueous solution of $KHSO_4$ 1M. The organic layer was diluted in AcOEt and washed with saturated $NaHCO_3$ solution, water and brine. The organic layer was dried over $Na_2SO_4$ and concentrated under reduced pressure to give the compound, which crystallized slowly.

To an ice-cooled solution of Boc-protected alcohol in anhydrous THF (15 mL) under $N_2$ were added Phtalimide (1.20 eq) and $PPh_3$ (1.20 eq). The reaction mixture was stirred for 10 min and DIAD (1.20 eq) was added dropwise. The reaction mixture was stirred at room temperature overnight. The THF was removed under vacuum and the mixture was dissolved in methanol and heated to 70° C. under $N_2$. Hydrazine (3.00 eq) was added slowly and the mixture was allowed to stir at 70° C. overnight.

The insoluble product was filtered off and washed with methanol. The filtrate and washings were combined and the solvent was removed under vacuum. The mixture was dissolved in $NaHCO_3$ and $CH_2Cl_2$. The organic layer was washed with saturated $NaHCO_3$, dried over $Na_2SO_4$, and concentrated under reduced pressure. The resulting oil was dissolved in concentrated HCl (pH 2-3) and the aqueous layer was washed with $Et_2O$ and EtOAc, the aqueous layer was then basified with $K_2CO_3$ until pH 8. The compound was extracted from the aqueous layer with $CH_2Cl_2$ (three times) and the organic phases were combined, dried over $Na_2SO_4$ and concentrated under reduced pressure.

To an ice-cooled solution of the Boc-protected amine dissolved in anhydrous $CH_2Cl_2$, was added DSC (1.20 eq) previously dissolved in $CH_2Cl_2$ and the mixture was stirred for 2 hours at room temperature. The mixture was diluted in $CH_2Cl_2$, the insoluble compounds were filtered off and washed with $CH_2Cl_2$. Then the organic layer was washed with saturated $Na_2SO_4$ and concentrated under reduced pressure. The desired activated building block was crystallised in a mixture of $Et_2O$ and pentane and recovered by filtration An exemplary procedure for Boc removal and peptide coupling in the synthesis of peptide-oligourea compounds of the present disclosure is as follows: the N-Boc protected oligomer was dissolved in TFA at 0° C. under $N_2$. After stirring for 1 hour, TFA was removed in vacuo and coevaporated with cyclohexane. The α-amino acid (0.95 eq.) was dissolved in a small quantity of dimethylformamide with BOP (0.95 eq.) and cooled to 0° C. under $N_2$, the TFA salt and DIPEA (3.0 eq.) were added and the reaction was allowed to stir over night. The mixture was diluted with $NaHCO_3$ and EtOAc. The organic layer was washed with $NaHCO_3$, $KHSO_4$ and brine, dried over $Na_2SO_4$, and concentrated under reduced pressure. The resulting solid was column purified ($CH_2Cl_2$/MeOH, 2%).

Materials and Methods

Functional Assay to Examine Bioactivity of GLP-1 Receptor Antagonists. Evaluation of the agonist activity of compounds at the mouse GLP-1 receptor endogenously expressed in βTC6 cells was examined by measuring their effects on cAMP production using the Homogeneous Time Resolved Fluorescence (HTRF) detection method, discussed in greater detail below. The βTC6 cells were suspended in Hank's Balanced Salt Solution (HBSS) buffer (Invitrogen) complemented with 20 mM HEPES (4-(2-hydroxyethyl)-1-piperazineethanesulfonic acid) (pH 7.4) and 500 µM IBMX (3-Isobutyl-1-methylxanthine), then distributed in microplates at a density of $1.5 \times 10^4$ cells/well and incubated for 10 minutes at room temperature in the presence of HBSS (basal control), the test compound or the reference agonist. For stimulated control measurement, separate assay wells contain 10 nM GLP-1(7-37) were utilized.

Following incubation, the cells were lysed and the fluorescence acceptor (D2-labeled cAMP) and fluorescence donor (anti-cAMP antibody labeled with europium cryptate) were added. After 60 minutes at room temperature, the fluorescence transfer was measured at $\lambda_{ex}=337$ nm and $\lambda_{em}=620$ nm and 665 nm with a microplate reader (Rubystar, BMG). The cAMP concentration was determined by dividing the signal measured at 665 nm by that measured at 620 nm (ratio). The results are expressed as a percent of the control response to 10 nM GLP-1(7-37). The standard reference agonist is GLP-1(7-37), which was tested in each experiment at several concentrations to generate a concentration-response curve from which its EC50 value was calculated.

Functional Assay to Examine Bioactivity of Glucagon Receptor Agonists. Evaluation of the agonist activity of compounds at the human glucagon receptor expressed in transfected CHO cells was examined by measuring their effects on cAMP production using the HTRF detection method. The CHO cells were suspended in HBSS buffer (Invitrogen) complemented with 20 mM HEPES (pH 7.4) and 500 µM IBMX, then distributed in microplates at a density of $10^4$ cells/well and incubated for 10 minutes at 37° C. in the presence of HBSS (basal control), the test compound or the reference agonist. For stimulated control measurement, separate assay wells contain 100 nM glucagon were utilized.

Following incubation, the cells were lysed and the fluorescence acceptor (D2-labeled cAMP) and fluorescence donor (anti-cAMP antibody labeled with europium cryptate)

were added. After 60 min at room temperature, the fluorescence transfer is measured at λex=337 nm and λem=620 and 665 nm using a microplate reader (Envision, Perkin Elmer). The cAMP concentration was determined by dividing the signal measured at 665 nm by that measured at 620 nm (ratio). The results are expressed as a percent of the control response to 100 nM glucagon. The standard reference agonist is glucagon, which was tested in each experiment at several concentrations to generate a concentration-response curve from which its EC50 value was calculated.

Functional Assay to Examine Bioactivity of MDM2 and MDMX Antagonists. The compounds were received dissolved in 100% DMSO at a final concentration of 10 mM and frozen. After complete defrosting and sonication, all compounds were diluted in 100% DMSO at both 0.4 mM, 0.04 and 0.004 mM, and distributed into two 96-well compounds daughter plates (Table 2).

Each compound was evaluated in duplicate on both (MDM2 or MDMX)/p53 interaction and on a positive TR-FRET control protein in a 384-well reaction plate. The final compound concentrations in these assays were 10 μM, 1 and 0.1 μM in 2.5% DMSO. The reference compound Nutlin-3 is integrated in the compound daughter plate and was used under the same conditions.

HTRF (Homogeneous Time-Resolved Fluorescence) principle. The HTRF technology is based on time resolved fluorescence energy transfer (TR-FRET), which occurs between long-lived fluorophore Europium or Terbium Cryptates, and EuK or Tb respectively, as a donor and the allophycocyanin XL665, d2 or Red as acceptor. Many compounds and proteins present in biological fluids or serum are naturally fluorescent, and the use of conventional, prompt fluorescence leads to serious limitations in assay sensitivity. The use of long-lived fluorophore combined with time-resolved detection (a delay between excitation and emission detection) minimizes prompt fluorescence interference.

The GST-Flag-Mdm2 (AA1-188; GI:4505136) or GST-Flag-MdmX (AA1-174; GI:88702790)/THX-HIS-p53 (AA1-83; GI:8400737) interaction was detected by an optimized HTRF assay. Specific anti-GST antibody bearing a fluorescence donor (EuK) and an anti-His antibody bearing a fluorescence acceptor (XL665) recognize tags on each fusion protein. The interaction between both purified proteins was detected by fluorescence transfer (excitation at 337 nm, emission at 665 nm). The emission at 620 nm occurs regardless of the interaction, and allows for normalizing the assay. Disruption of the protein-protein interaction suppresses the signal.

A measure of the HTRF signal obtained for the protein-protein interaction is brought by:

$$DeltaF\ (\%) = 100 \times \frac{(ratio_{sample} - ratio_{background})}{ratio_{background}}$$

Where, "ratio" is the 665/620 fluorescence ratio, "sample" is the signal in presence of HTRF antibodies and "background" denotes the HTRF antibodies in buffer only.

For each evaluated compound, raw data files indicate the fluorescence signal at 620 and 665 nm and the 665/620 fluorescence ratio of the two replicates. The analysis files provide Inhibition % of the interaction for each replicate, and compute the mean value and standard deviation for each compound.

In order to evaluate the influence of the compounds on the tag-antibody recognition, all compounds were simultaneously evaluated with a HTRF assay using a His-MBP-GST-Flag (HMGF) fusion protein as a TR-FRET positive control. Loss of fluorescence transfer indicates that the compounds interfere with GST or His recognition by their respective antibodies.

Enzymatic Degradation—Chymotrypsin and Trypsin. Stock solutions of the compounds were prepared at a concentration of 400 μM in a solution of 50 mM HEPES buffer, 50 mM NaCl, 0.05% Tween-80, pH 8.0. Stock solution of the chymotrypsin or trypsin was prepared at a concentration of 250 μg/mL in water. Stability of compounds to chymotrypsin was assessed by conducting a protease reaction in a 96-well plates at room temperature. Each well received 10 μL of HEPES buffer, 38 μL of the solution of compound to be assayed (final concentration 304 μmol/L), and 2 μL of the enzyme solution (final concentration 10 μg/mL) for a total volume of 50 μL. Each compound was also incubated in the absence of the enzyme (12 μL of HEPES buffer and 38 μL of the compound).

At the indicated time (5, 10, 15, 30 and 60 minute(s)) a 10 μL aliquot was removed from each experimental reaction and pipet into 100 μL of 1% TFA solution to quench the reaction (t=0 minutes was determined using the reaction without enzyme). A portion of the quenched reaction solution was analyzed by HPLC. The time course of peptide degradation was determined by integrating the area of each peak in a series of HPLC traces. Another portion of the quenched reaction was analyzed by LC-MS for identification of each peptide fragment.

Enzymatic Degradation—Leucyl Aminopeptidase. Leucyl aminopeptidase (EC 3.4.11.1) from porcine kidney (Sigma); chromatographically purified suspension in 2.9 M (NH4)2SO4, 0.1 M Tris, 5 mM MgCl2 solution, pH 8.0; stock solution in PBS buffer (pH 7.2, 0.01 M). For each degradation experiment, stock solutions of the peptidic substrate and the enzyme were made using phosphate-buffered saline (PBS) buffer solution. The enzyme concentrations of the stock solutions were selected such that the standard substrates were totally degraded after a maximum of 15 min (ratio 2[enzyme]:100[substrate]). PBS buffer solution (10 mM sodium phosphate, 0.14 M NaCl) was prepared as follows: Solution A (4.75 mL of 0.2 M $NaH_2PO_4 \cdot H_2O$), solution B (20.25 mL of 0.2 M $Na_2HPO_4 \cdot H_2O$), NaCl (4.5 g), and $H_2O$ (25 mL) were stirred for 15 min at room temperature and diluted tenfold with $H_2O$. The pH was adjusted either with NaOH (1 M) or with HCl (1 M) prior to use. A solution of the substrate in PBS buffer (pH 7.2, 0.01 M) and a solution of the required amount of enzyme, were mixed and incubated at 25° C. for 4 hours. Degradation was stopped with concentrated AcOH, and buffer solution was added so that the total volume reached 150 μL.

The resulting mixture was analyzed by reversed-phase HPLC. A mixture of $CH_3CN/H_2O$ (0.1% TFA) was used as eluent. Gradients were 10% $CH_3CN$ to 100% $CH_3CN$ in 10 minutes. The flow rate, for all separations, was 1 $mL \cdot min^{-1}$.

Enzymatic Degradation—Carboxypeptidase A. Carboxypeptidase A (EC 3.4.17.1) from bovine pancreas (Fluka), milky suspension, stock solution in PBS buffer (pH 7.5, 0.01 M). For each degradation experiment, stock solutions of the peptidic substrate and the enzyme were made using phosphate-buffered saline (PBS) buffer solution. The enzyme concentrations of the stock solutions were selected such that the standard substrates were totally degraded after a maximum of 15 min (ratio 2[enzyme]:100[substrate]). PBS buffer solution (10 mM sodium phosphate, 0.14 M NaCl) was prepared as follows: Solution A (4.75 mL of 0.2 M $NaH_2PO_4.H_2O$), solution B (20.25 mL of 0.2 M $Na_2HPO_4.H_2O$), NaCl (4.5 g) and H2O (25 mL) were stirred for 15 min at room temperature and diluted tenfold with $H_2O$. The pH was adjusted either with NaOH (1 M) or with HCl (1 M) prior to use. A solution of the substrate in PBS buffer (pH 7.5, 0.01 M) and a solution of the required amount of enzyme, were mixed and incubated at 25° C. for 4 hours. Degradation was stopped with concentrated AcOH, and buffer solution was added so that the total volume reached 150 µL.

The resulting mixture was analyzed by reversed-phase HPLC. A mixture of $CH_3CN/H_2O$ (0.1% TFA) was used as eluent. Gradients were 10% $CH_3CN$ to 100% $CH_3CN$ in 10 minutes. The flow rate, for all separations, was 1 $mL \cdot min^{-1}$.

Solubility. A solution of 3 mg/ml of glucagon (or analog) was prepared in a 0.01M HCl solution. Then 0.1 ml of the stock solution was diluted to 1 ml with HCl (0.01M) and the UV absorbance measured (to 280 nm) with nanodrop UV spectrometer. The pH of the remaining stock solution was adjusted to 7 using $Na_2HPO_4$, and the solution was incubated overnight at 4° C. The solution was then centrifuged three times (5 minutes, 4000 rotations per minute), 0.1 ml of the supernatant was removed and diluted to 1 ml with HCl solution (0.01M).

The final UV absorbance was measured. The solubility was accessible by the following calculation: (Final absorbance/Initial absorbance)×3 mg/ml=solubility (mg/ml).

In Vivo Examination of. All procedures were performed in accordance with the Guide for the Care and Use of Laboratory Animals (revised 1996 and 2011, 2010/63/EU) and French laws. Sixty eight-week old C57B1/6J, male mice weighing 20-25 g were obtained by CHARLES RIVER LABORATORIES (France, BP 0109, 69 592 L'ARBRESLE Cedex France). Mice were identified with ear tags. The 60 mice were housed in ventilated and enriched housing cages (310×125×127 $mm^3$) throughout the experimental phase. The mice were housed in groups of 5 animals during the whole study, on a normal 12 hours light cycle (at 08:00 pm lights off), 22±2° C. and 50±10% relative humidity. The mice were acclimated for 5-days. A standard chow diet (RM1 (E) 801492, SDS) and tap water were provided ad libitum.

Treatments: Mice were acutely treated by i.v. injection. After the acclimation period, mice were randomized into 10 groups (n=6/group) according to their body weight. They were dosed (1 µg/mouse i.v.) at 8 AM and fasted. Then mice were subjected to an Intraperitoneal Glucose Tolerance Testing (IPGTT). The mice were then sacrificed by cervical dislocation.

Results

Functional Analysis of GLP-1 Receptor Antagonists. Table 1 shows the EC50 of GLP-1 antagonists compounds 1-8, 12-15, 25-28, 43-50, 66-69, 72, and 73, which have the amino acid sequence of SEQ ID NOS: 1-8, 12-15, 25-28, 43-50, 66-69, 72, and 73, respectively. It was surprisingly discovered, as shown in Table 1, that the monosubstitution of one or more amino acids by an amino urea in a GLP-1 antagonist generally maintained functional activity.

TABLE 1

| GLP-1 Functional Assay Results | | | |
|---|---|---|---|
| Compound | EC50 (nM) | Compound | EC50 (nM) |
| 1 | 0.072 | 14 | 0.15 |
| 2 | 1.5 | 15 | 0.13 |
| 3 | 0.46 | 29 | 0.26 |

TABLE 1-continued

| GLP-1 Functional Assay Results | | | |
|---|---|---|---|
| Compound | EC50 (nM) | Compound | EC50 (nM) |
| 4 | 0.26 | 30 | 0.18 |
| 5 | 0.42 | 14 | 0.15 |
| 6 | 0.21 | 47 | 0.066 |
| 7 | 0.22 | 48 | 0.086 |
| 8 | 0.2 | 49 | 0.068 |
| 12 | 280 | 50 | 0.071 |
| 13 | 0.079 | 28 | 0.074 |
| 25 | 0.074 | 66 | 0.06 |
| 26 | 0.073 | 67 | 0.082 |
| 27 | 0.081 | 15 | 0.13 |
| 42 | 1.4 | 68 | 1 |
| 43 | 0.77 | 69 | 0.21 |
| 44 | 0.048 | 72 | 0.056 |
| 45 | 0.036 | 73 | 0.34 |
| 46 | 0.046 | | |

Functional Analysis of MDM2 or MDMX Antagonists. Table 2 shows the EC50 of MDM2 and MDMX antagonists compounds 19-22 and 37-41, which have the amino acid sequence of SEQ ID NOS: 19-22 and 37-41, respectively. It was surprisingly discovered, as shown in Table 2, that the monosubstitution of one or more amino acids by an amino urea in an MDM2 or MDMX antagonist generally maintained functional activity.

TABLE 2

| MDM2 and MDMX Functional Assay Results | | |
|---|---|---|
| Compound | MDM2 EC50 (nM) | MDMX EC50 (nM) |
| 19 | 0.6 | 3.1 |
| 20 | 2.3 | 7.7 |
| 21 | 6.9 | 22.6 |
| 37 | 6 | 25 |
| 38 | 1.3 | 252 |
| 39 | 2 | 4.9 |
| 40 | 0.9 | 17 |
| 41 | 0.7 | 3.3 |
| 22 | 1.3 | 11.3 |
| 23 | 0.75 | 6.3 |
| 24 | 5.4 | 48.6 |

Functional Examination of Glucagon Receptor Agonists. Table 3 shows the EC50 of glucagon receptor agonists compounds 16, 34-36, 51-53, and 55-65, which have the amino acid sequence of SEQ ID NOS: 16, 34-36, 51-53, and 55-65, respectively. It was surprisingly discovered, as shown in Table 3, that the monosubstitution of one or more amino acids by an amino urea in a glucagon receptor agonist generally maintained functional activity.

TABLE 3

| Glucagon Functional Assay Results | | | |
|---|---|---|---|
| Compound | EC50 (nM) | Compound | EC50 (nM) |
| 16 | 0.064 | 57 | 22 |
| 34 | 2.5 | 58 | 35 |
| 35 | 0.44 | 34 | 2.5 |
| 36 | 0.026 | 59 | 32 |
| 16 | 0.064 | 54 | 32 |
| 36 | 0.026 | 60 | 36 |
| 16 | 0.064 | 61 | 0.1 |
| 51 | 68 | 62 | 53 |

TABLE 3-continued

Glucagon Functional Assay Results

| Compound | EC50 (nM) | Compound | EC50 (nM) |
|---|---|---|---|
| 52 | 34 | 63 | 30 |
| 53 | 0.67 | 64 | 0.16 |
| 55 | 34 | 65 | 1.5 |
| 56 | 0.072 | 16 | 0.064 |

GLP-1 Enzymatic Stability. It was surprising that the monosubstitution of one or more amino acids by an amino urea improved the stability of peptides toward enzymatic degradation, while maintaining a good affinity with its receptor. Compounds 2, 3, 4, 5, 6, 7, and 8, which have the amino acid sequence of SEQ ID NOS: 2, 3, 4, 5, 6, 7, and 8 respectively, showed longer half-life compare to the native peptide (GLP-1; SEQ ID NO: 1) in the chymotrypsin degradation test. In the trypsin degradation test, compounds 9, 10, and 11, which has the amino acid sequence of SEQ ID NOS: 9, 10, and 11 respectively, showed longer half-life compare to the native peptide (GLP-1; seq. 1). Half-lives were also measure using leucyl aminopeptidase. Compounds 2, 13, 15, 17, 18, and 19-24, which have the amino acid sequence of SEQ ID NOS: 12, 13, 15, 17, 18, and 19-24, respectively, were all more stable than the native peptides. The same results were obtained with carboxipeptidase A when comparing compounds 2, 3, 4, 5, 6, 7, and 24, which have the amino acid sequence of SEQ ID NOS: 25-41, 22, 23, and 24 respectively, with their native peptides.

Affinity for a Receptor of the Peptide. Compounds 1, 16, 14, 28, 36, and 42-50, which correspond to the amino acid sequence of SEQ ID NOS: 1, 16, 14, 28, 36, and 42-50 respectively, were examined for their receptor affinity. Table 4 shows multiple examples of peptides with better affinity for a receptor than the corresponding native peptide. It is noteworthy that a gamma-amino acid and an amino carbamate residue were less efficient than the corresponding amino urea.

TABLE 4

Affinity for a corresponding receptor of different peptides

| Compound | Reference Compound | Receptor | % bioactivity of reference | comment |
|---|---|---|---|---|
| 16 | — | GCG-R | — | |
| 36 | 16 | GCG-R | 246 | |
| 1 | — | GLP-1R | — | |
| 42 | 1 | GLP-1R | 5 | gamma-amino acid |
| 43 | 1 | GLP-1R | 9 | carbamate |
| 13 | 1 | GLP-1R | 91 | urea |
| 44 | 1 | GLP-1R | 150 | |
| 45 | 1 | GLP-1R | 200 | |
| 46 | 1 | GLP-1R | 157 | |
| 14 | — | GLP-1R | — | |
| 47 | 14 | GLP-1R | 227 | |
| 48 | 14 | GLP-1R | 174 | |
| 49 | 14 | GLP-1R | 221 | |
| 50 | 14 | GLP-1R | 211 | |
| 28 | 14 | GLP-1R | 203 | |

Glucagon Solubility. Compounds 16, and 51-65, which have the amino acid sequence of SEQ ID NO: 16 and 51-65, were examined for solubility. It was surprisingly discovered that the monosubstitution of one or more amino acids by an amino urea in glucagon had the general effect of improving its solubility. Table 5 illustrates the improvement of glucagon analog solubility which moderated bio activities.

TABLE 5

Solubility of Glucagon Analogs

| Compound | Solubility (mg/ml) | ratio |
|---|---|---|
| 16 (reference) | 0.25 | 1.0 |
| 51 | 0.56 | 2.2 |
| 52 | 0.49 | 1.9 |
| 53 | 0.58 | 2.3 |
| 54 | 0.63 | 2.5 |
| 55 | 1.39 | 5.5 |
| 56 | 0.70 | 2.8 |
| 57 | 0.97 | 3.9 |
| 58 | 1.51 | 6.0 |
| 34 | 0.86 | 3.4 |
| 59 | 0.72 | 2.9 |
| 54 | 0.63 | 2.5 |
| 60 | 0.83 | 3.3 |
| 61 | 0.74 | 2.9 |
| 62 | 0.68 | 2.7 |
| 63 | 1.28 | 5.1 |
| 64 | 0.94 | 3.7 |
| 65 | 0.85 | 3.4 |

Figure 3A:
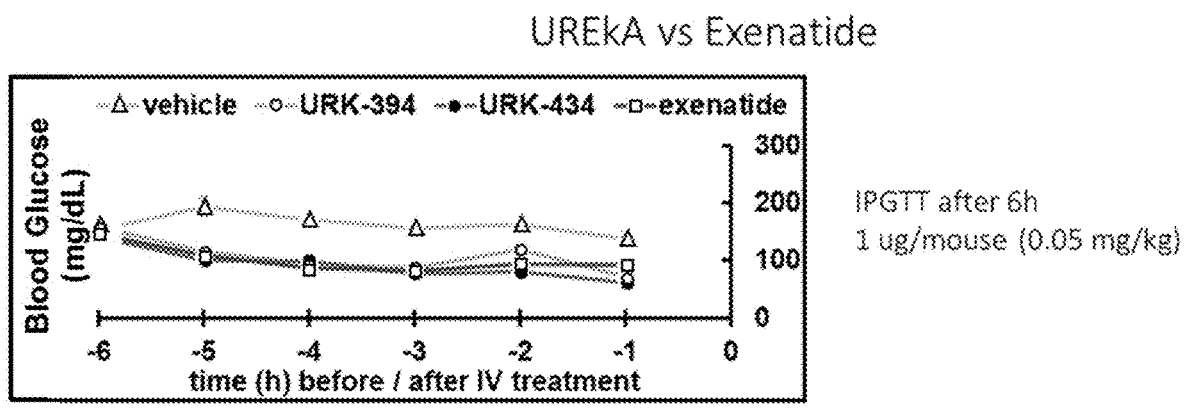
FIGS. 3A, 3B, and 3C. Comparison of exemplary peptide foldamers as described herein with exenatide.
Figure 3B:
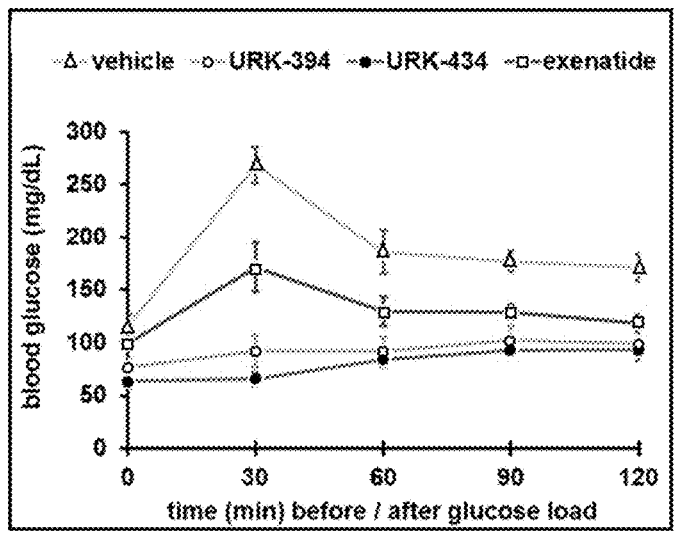
Figure 3C:
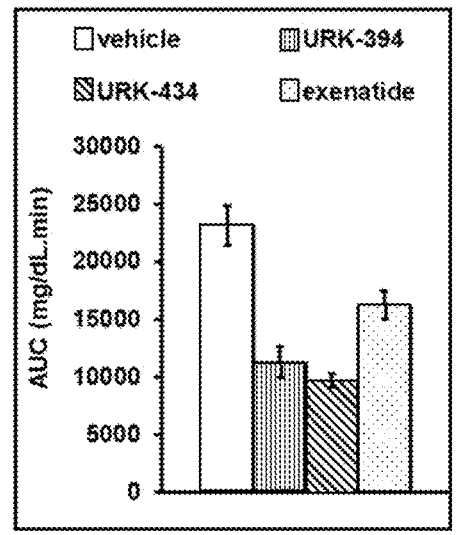
Figure 4A:
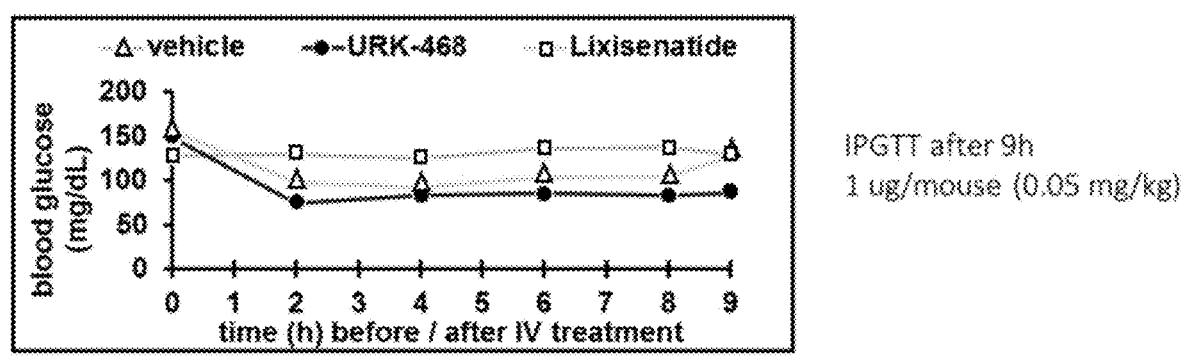
FIGS. 4A, 4B, and 4C. Comparison of exemplary peptide foldamers as described herein with lixisenatide.
Figure 4B:
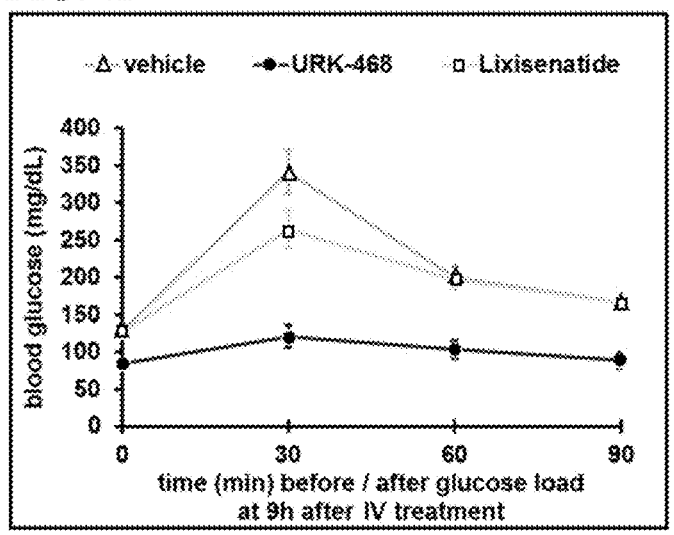
Figure 4C:
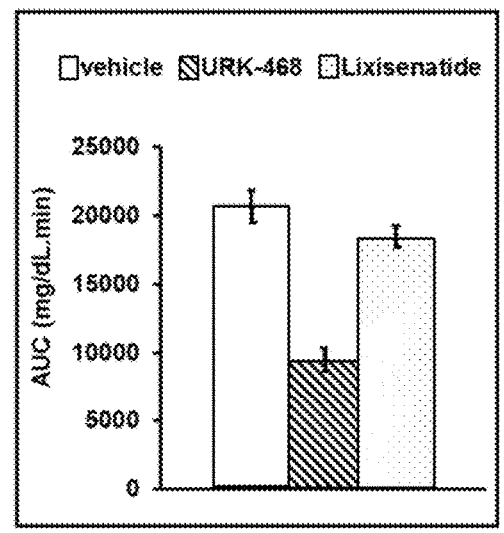
Figure 5:
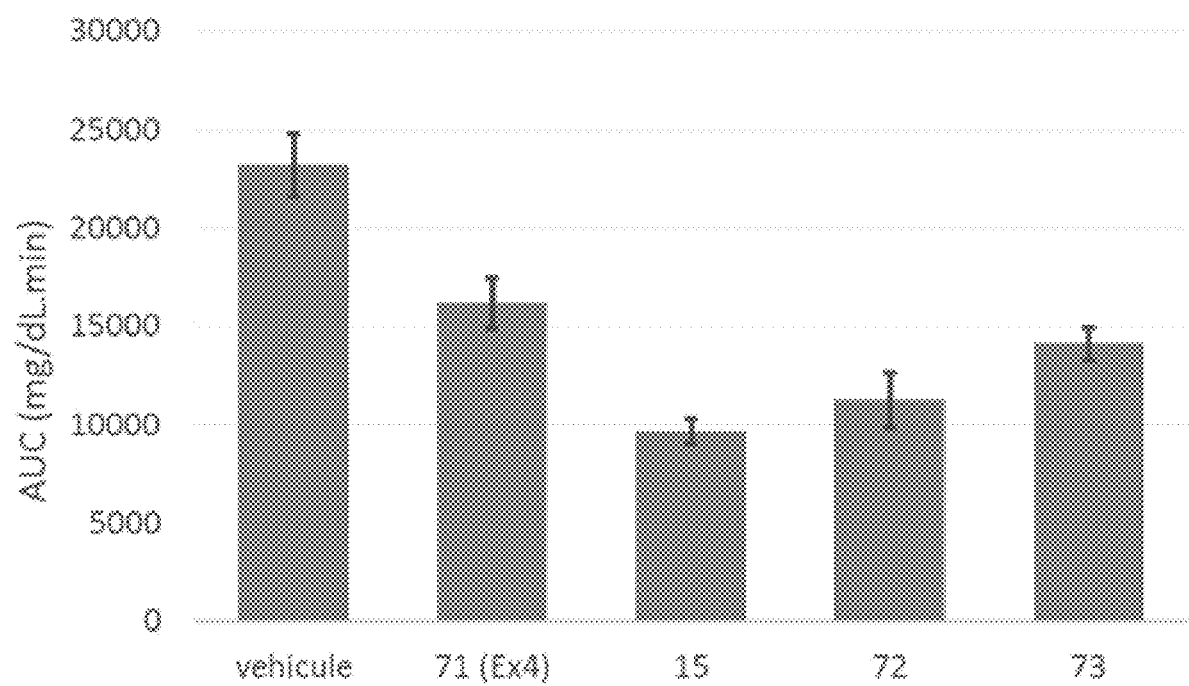
FIGS. 5 and 6. Comparison of exemplary compounds as described herein with compound 71 (Exendin-4.

Examination of Blood Glucose after IV Treatment with Exenatide, Lixisenatide, or Exemplary Peptide-urea Compounds. FIGS. 3A, 3B, 3C, 4A, 4B, 4C, and 5 demonstrate the comparison of exemplary peptide compounds as described herein with exenatide, or lixisenatide. FIGS. 3A and 4A show the effect compounds URK-394 (SEQ ID NO: 72) and URK-434 (SEQ ID NO: 15) has on blood glucose before and after IV treatment, relative to vehicle and exenatide. FIGS. 3B and 4B show the effect compounds URK-394, URK-434, and URK-468 (SEQ ID NO: 67) has on blood glucose before and after glucose load, relative to vehicle and exenatide. FIGS. 3C and 4C show that the area under the curve (AUC) for the same. FIG. 5 compares several exemplary compounds as described herein with exenatide.

Figure 6:
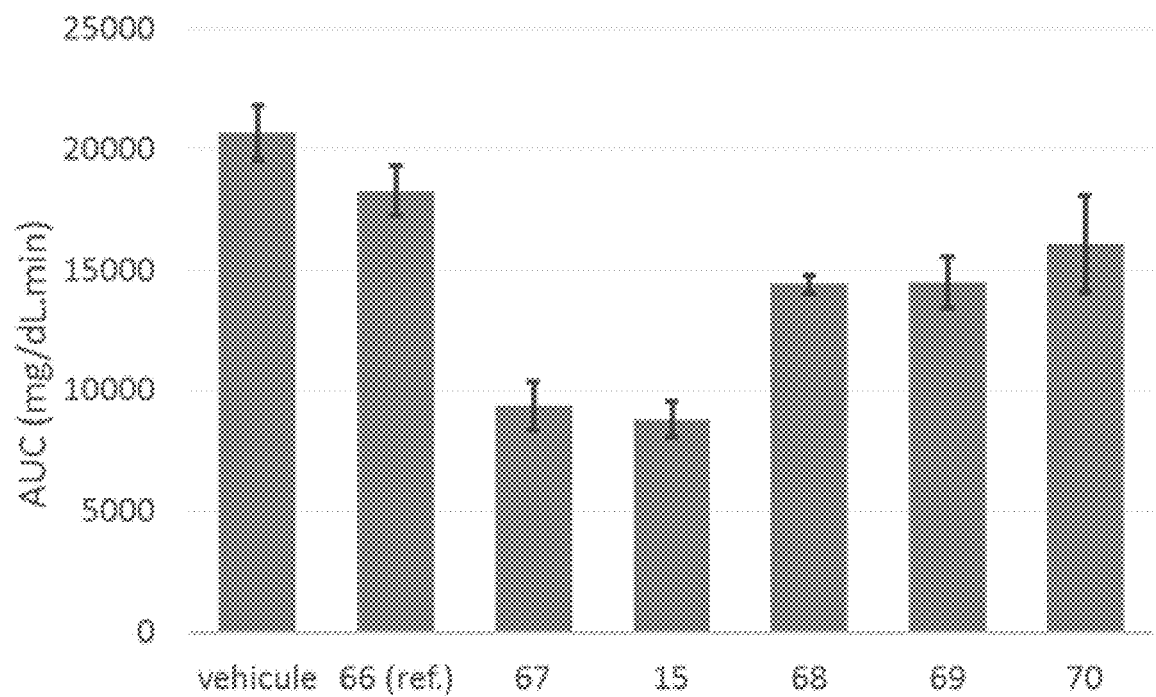
Figure 8A:
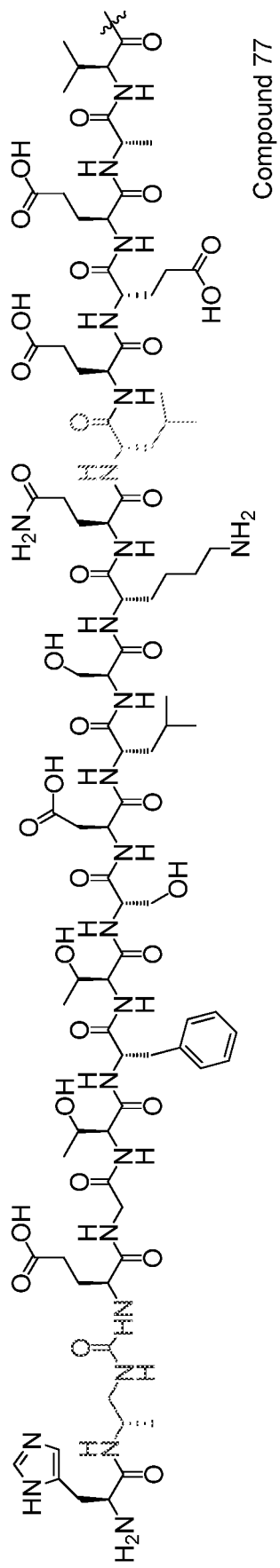
FIGS. 8A, 8B, 8C, 8D, 8E, 8F, and 8G.
Figure 8A:
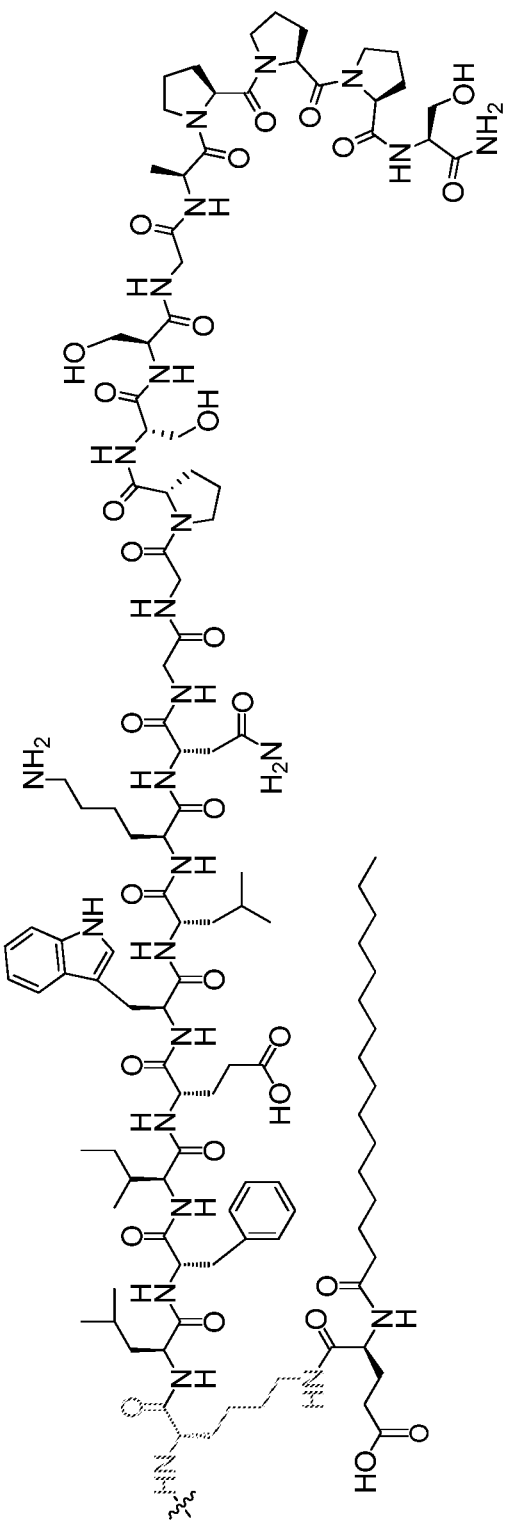
Figure 8B:
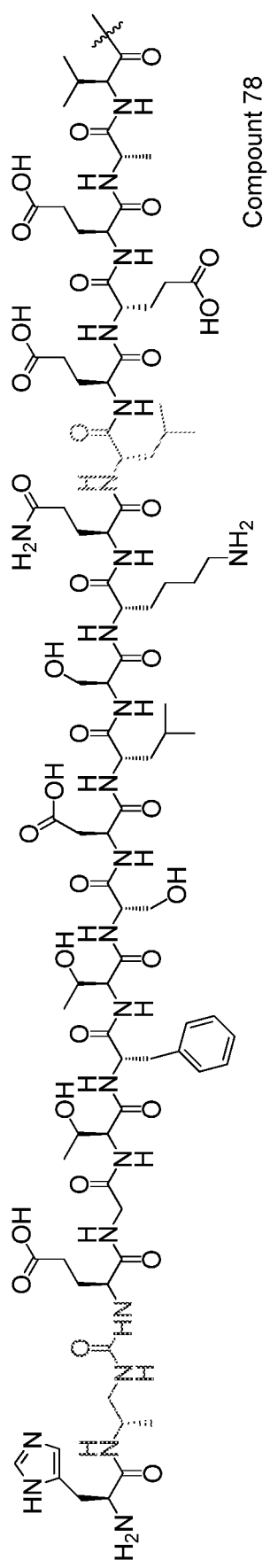
Figure 8B:
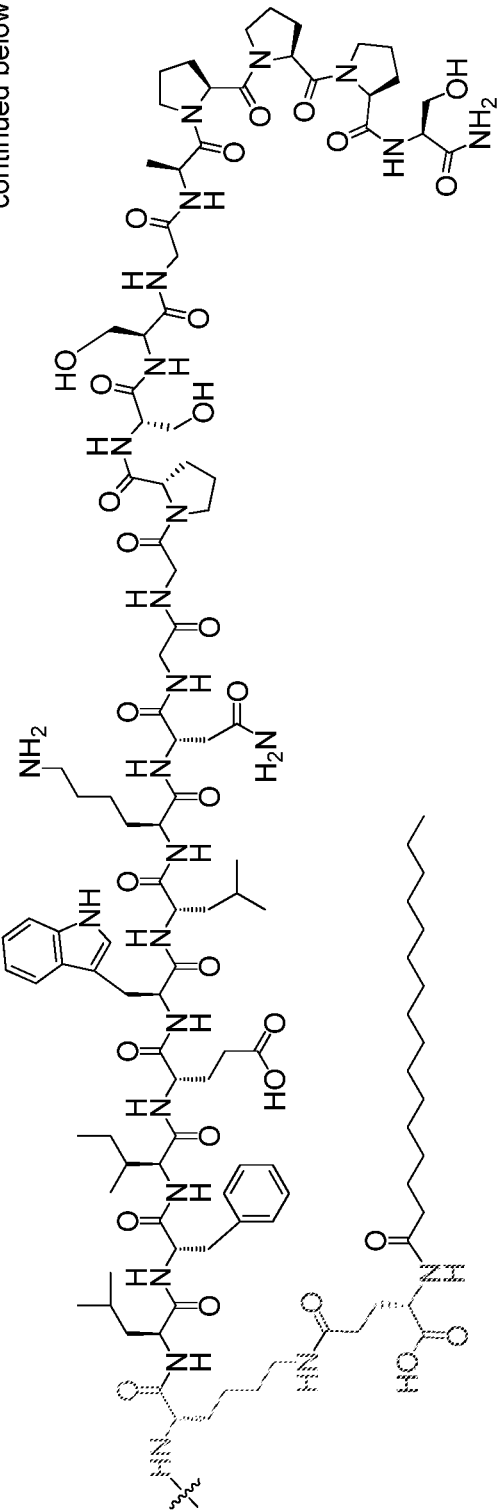
Figure 8C:
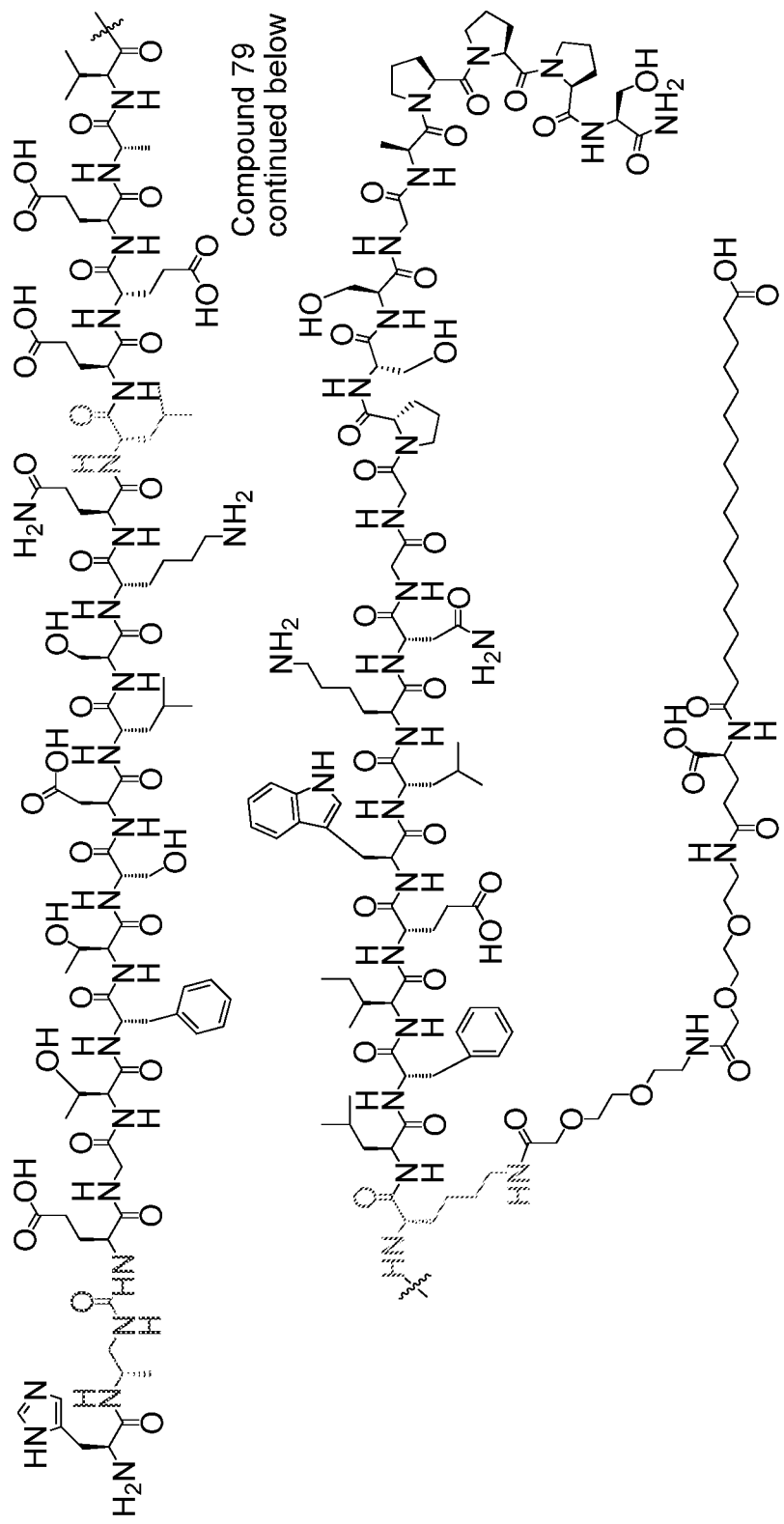
Figure 8D:
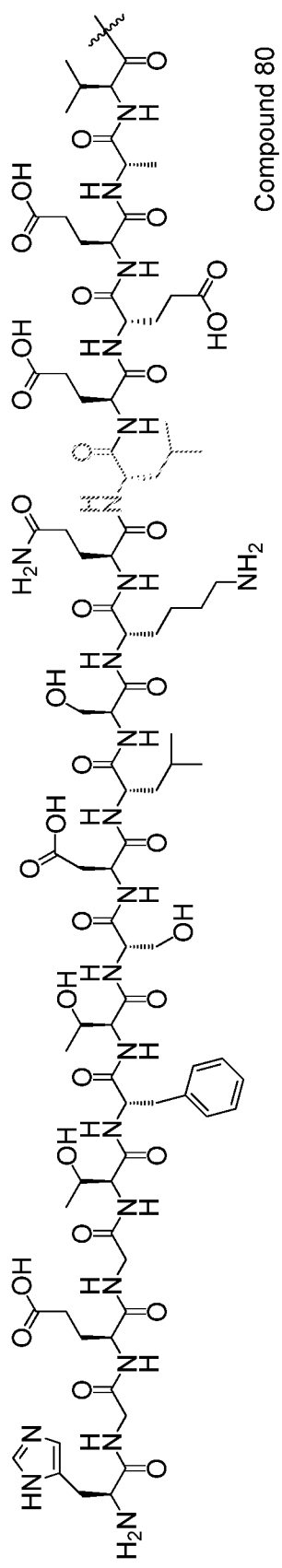
Figure 8D:
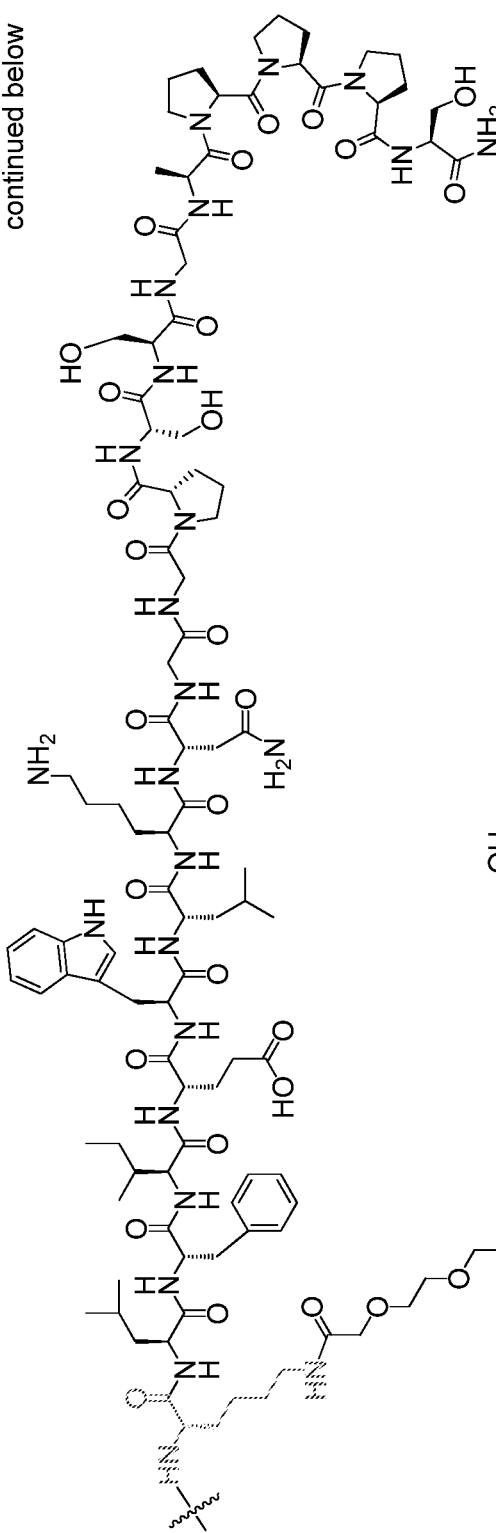
Figure 8D:
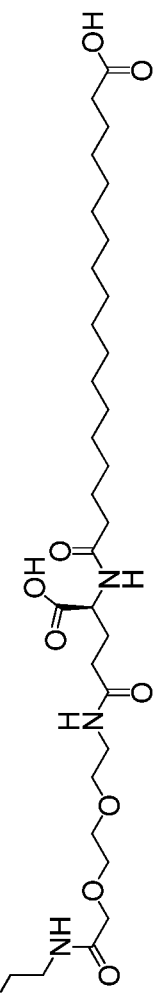
Figure 8E:
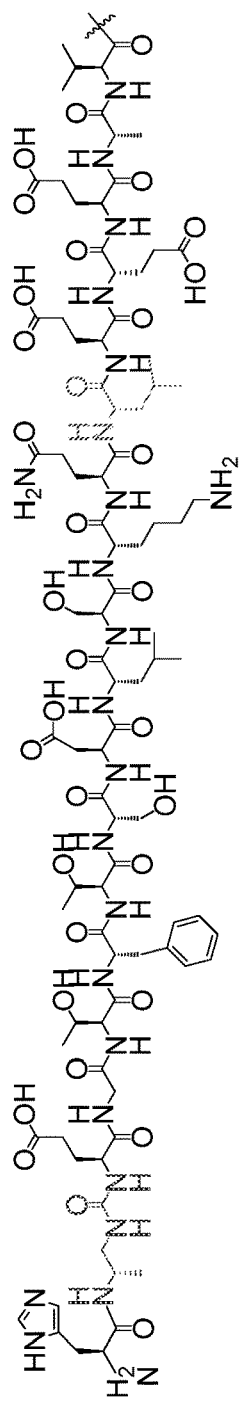
Figure 8E:
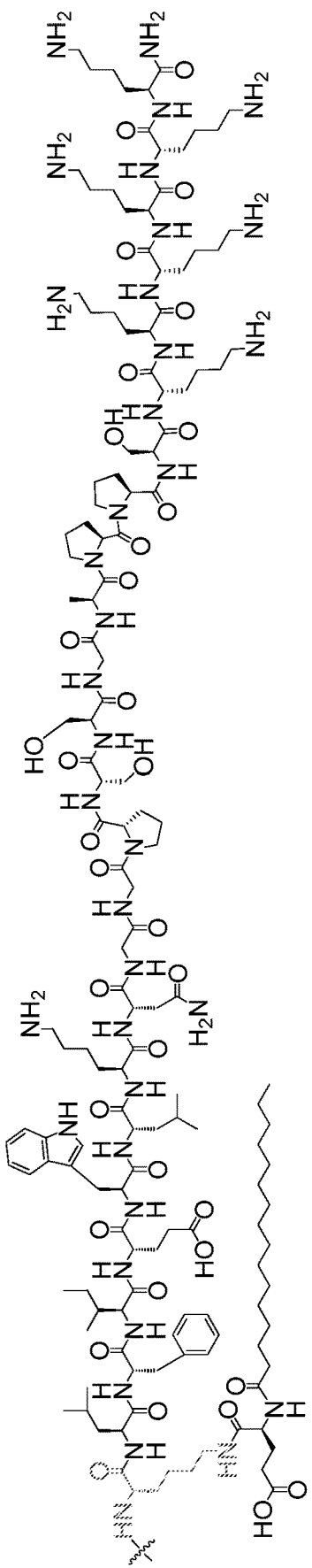
Figure 8F:
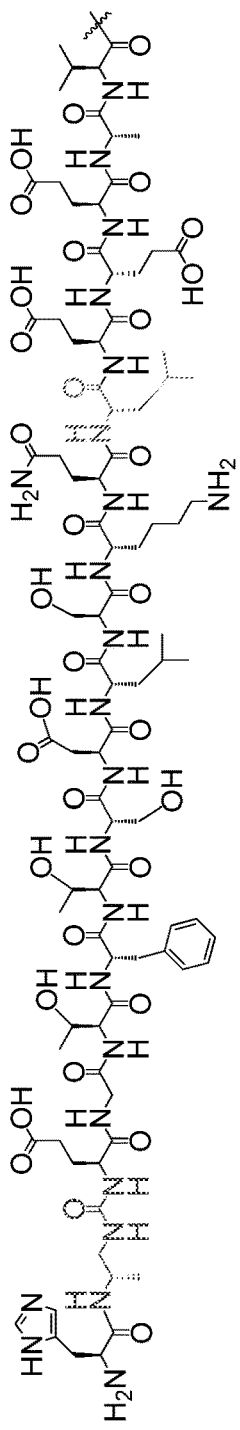
Figure 8F:
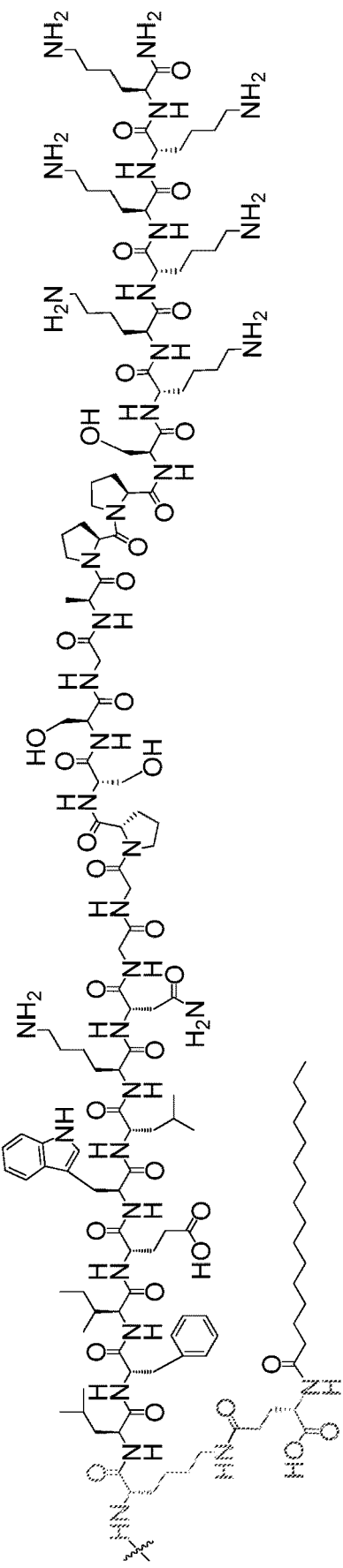
Figure 8G:
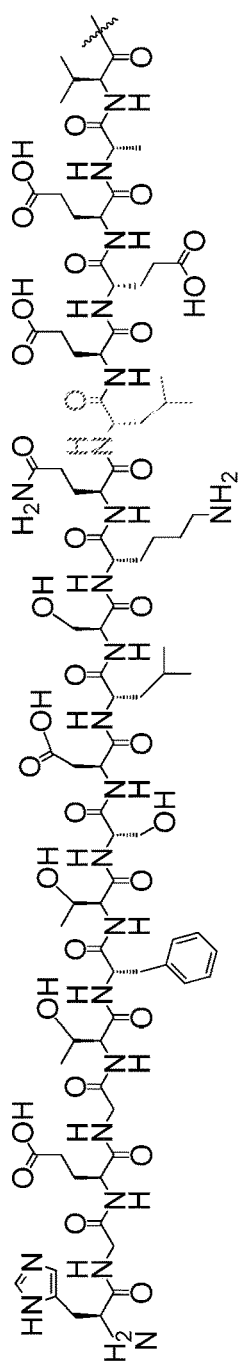
Figure 8G:
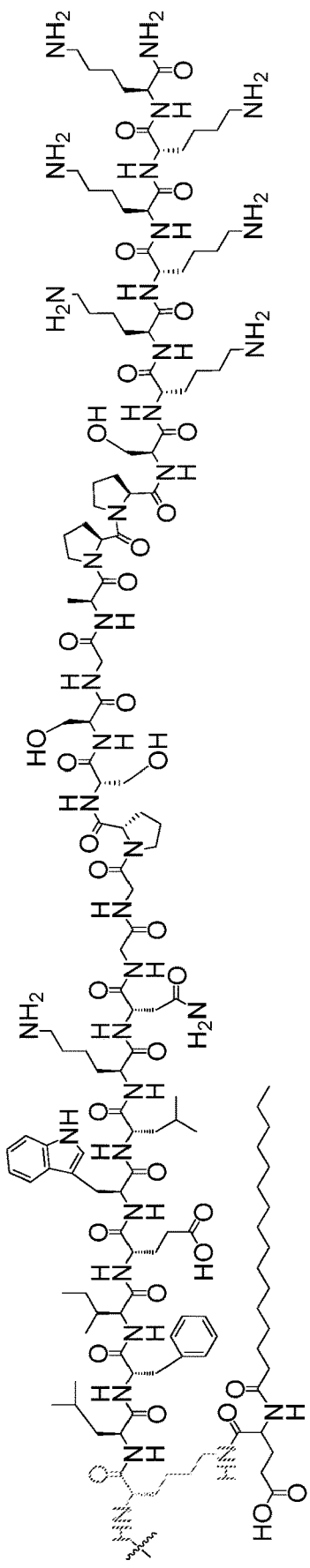
Figure 9:
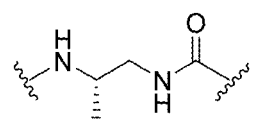
FIG. 9. Illustrate the chemical structure of a urea, a γ-amino acid, and a N,N'-linked carbomyl. As such, one skilled in the art would appreciated that an amino acid abbreviation followed with a superscript "u" represents a urea substitution with the specified amino acid side chain (e.g., as shown in FIG. 9, $A^u$ represents a urea substitution with an alanine side chain); an amino acid abbreviation followed with a superscript "c" represented a N,N'-linked carbomyl with the specified amino acid side chain (e.g., as shown in FIG. 9, $A^c$ represents an N,N' linked carbomyl with an alanine side chain); and "γ" followed by an amino acid abbreviation represents a γ-amino acid of the specified amino acid (e.g., γA represents a γ alanine).
Figure 9:
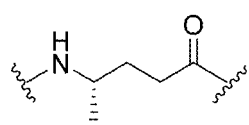
Figure 9:
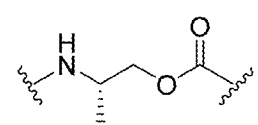

It was also surprisingly discovered, as shown in FIGS. 5 and 6, that the monosubstitution of one or more amino acids by an amino urea in exenatide and lixisenatide improved their therapeutic effect. The longer effect suggest that the urea diminish the clearance rate of those analogs.

The data demonstrate that exemplary compounds with at least one monosubstitution of one or more amino acids by a amino urea had significant improvement in therapeutic effect, as exemplified by the reduction of the glucose peak and the correlated reduction of the AUC, as compared to exenatide.

FIG. 7 illustrates an alignment of URK-479 ( ) URK-468 (SEQ ID NO: 67), URK-470 (SEQ ID NO: 73), URK-434 (SEQ ID NO: 15), URK-526 (SEQ ID NO: 68), URK-280 (SEQ ID NO: 69), and URK-527 (SEQ ID NO: 74) with Exendin-4 (SEQ ID NO: 71).

Specific Embodiments

In an aspect, the present disclosure provides a method of improving at least one biological property of a peptide or peptidomimetic, wherein the biological activity is selected from the group consisting of therapeutic effect, stability toward enzymatic degradation, stability, solubility, affinity for a receptor, ligand or other polypeptide or peptide that interacts with the native, natural or unmodified peptide, clearance, and combinations thereof, the method comprising: substituting a plurality of amino acids of the peptide or peptidomimetic with a residue selected from an aminourea, a thiourea, and a guanidine, wherein at least one non-consecutive amino acid has been monosubstituted by an aminourea, a thiourea, or a guanidine.

In any aspect or embodiments described herein, the monosubstituted amino acid is located in the first 4 amino acids (N-terminal) of the peptide.

In any aspect or embodiments described herein, wherein the monosubstituted amino acid is located in the last 4 amino acids (C-terminal) of the peptide.

In any aspect or embodiments described herein, wherein the monosubstituted amino acid is located at or within 3 amino acids of a peptidase degradation site of the peptide.

In any aspect or embodiments described herein, wherein the monosubstituted amino acid is located at or within 3 amino acids of an amino acid that is key for the interaction between the protein and a receptor, ligand or other polypeptide that interacts with the native, natural, or unmodified protein.

In any aspect or embodiments described herein, wherein the monosubstituted amino acid is located at or within 3 amino acids of an amino acid that is key for at least one pharmacokinetic property of the peptide.

In any aspect or embodiments described herein, wherein the monosubstituted amino acid is located at or within 3 amino acids of an amino acid that is key for at least one physical property of the peptide.

In any aspect or embodiments described herein, wherein 3 or more amino acids have been substituted with a residue.

In any aspect or embodiments described herein, wherein 4 or more amino acids have been substituted with a residue.

In any aspect or embodiments described herein, wherein the peptide is 4 or more amino acids.

In any aspect or embodiments described herein, wherein the peptide is 5 or more amino acids.

In any aspect or embodiments described herein, wherein the peptide is 6 or more amino acids.

In any aspect or embodiments described herein, wherein the substitution is an N,N' linked substitution.

In any aspect or embodiments described herein, wherein the aminourea, the thiourea, the guanidine are independently selected from the group consisting of:

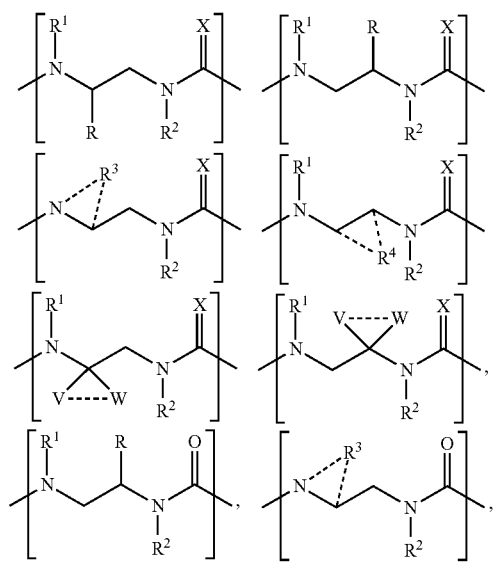

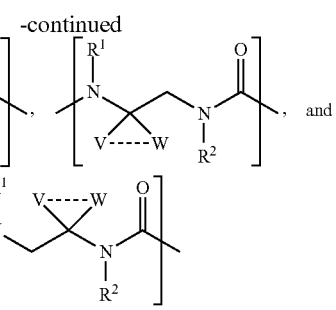

wherein X is independently selected from the group consisting of O, S, NH;

wherein R is independently selected from the group consisting of hydrogen, any side chain of a natural amino acid, linear, branched or cyclic C1-C6-alkyl, alkenyl or alkynyl; mono- or -bicyclic aryl, mono or bicyclic heteroaryl having up to five heteroatoms selected from N, O and S; mono or bicyclic aryl-C1-C6-alkyl, alkenyl or alkynyl; C1-C6-alkyloxy, aryloxy, heteroaryloxy, thio, C1-C6-alkylthio, amino, mono ordi-C1-C6-alkylamino, carboxylic acid, carboxamide mono- or di-C1-C6-alkylcarboxamine, sulfonamide, urea, mono-di or tri-substituted urea, thiourea, guanidine;

wherein $R^1$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S;

wherein $R^2$ is independently selected from the group consisting of hydrogen, linear, branched or cyclic C1-C6-alkyl, alkenyl or alkynyl; mono- or -bicyclic aryl, mono or bicyclic heteroaryl having up to five heteroatoms selected from N, O and S;

wherein $R^3$ together with the carbon and nitrogen atoms to which it is attached independently defines a substituted or unsubstituted, monocyclic or bicyclic C3-C10 heterocyclic ring having one or more N, O, or S atom(s) as the heteroatom(s); and substitutents on the cycloalkyl, cycloalkenyl or heterocycle moieties are independently selected from the group consisting of linear, branched or cyclic C1-C6 alkyl, aralkyl, —O—C(O)—NR$^1$R$^2$ or —N(R$^1$)—C(O)—O—R$^1$, C1-C6 alkylene-NR$^1$R$^2$, —(CH$_2$)$_n$—NH—C(=NR$^1$)NHR$^2$, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, —(CH$_2$)$_n$O—(C1-C6 alkyl), —(CH$_2$)$_n$C(O)—(C1-C6 alkyl), —(CH$_2$)$_n$OC(O)—(C1-C6 alkyl), —(CH$_2$)$_n$C(O)O—(C1-C6 alkyl), —(CH$_2$)$_n$NHC(O)—R$^1$, —(CH$_2$)$_n$C(O)—NR$^1$R$^2$, —(OCH$_2$)$_n$OH, —(OCH$_2$)$_n$O—(C1-C6 alkyl), —(CH$_2$O)$_n$C(O)—(C1-C6 alkyl), —(OCH$_2$)$_n$NHC(O)—R$^1$, —(CH$_2$O)$_n$C(O)—NR$^1$R$^2$, —NO2, —CN, or -halogen.R1 and R2 are each, within context, H or a C1-C6 alkyl group;

wherein $R^4$ together with the carbon atoms to which it is attached independently defines a substituted or unsubstituted, monocyclic or bicyclic C3-C10 cycloalkyl, cycloalkenyl or heterocyclic ring having one or more N, O, or S atom(s) as the heteroatom(s); and substitutents on the cycloalkyl, cycloalkenyl or heterocycle moieties are independently selected from the group consisting of linear, branched or cyclic C1-C6 alkyl, aralkyl, —O—C(O)—NR$^1$R$^2$ or —N(R$^1$)—C(O)—O—R$^1$, C1-C6 alkylene-NR$^1$R$^2$, —(CH$_2$)$_n$—NH—C(=NR$^1$)NHR$^2$, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, —(CH$_2$)$_n$O—(C1-C6 alkyl), —(CH$_2$)$_n$C(O)—(C1-C6 alkyl), —(CH$_2$)$_n$OC(O)—(C1-C6 alkyl), —(CH$_2$)$_n$C(O)O—(C1-C6 alkyl), —(CH$_2$)$_n$NHC(O)—R$^1$, —(CH$_2$)$_n$C(O)—NR$^1$R$^2$, —(OCH$_2$)$_n$OH, —(OCH$_2$)$_n$O—(C1-C6 alkyl), —(CH$_2$O)$_n$C(O)—(C1-C6 alkyl), —(OCH$_2$)$_n$NHC(O)—R$^1$, —(CH$_2$O)$_n$C(O)—NR$^1$R$^2$, —NO2, —CN, or -halogen.R1 and R2 are each, within context, H or a C1-C6 alkyl group; and wherein V and W are combined, together with the carbon atoms to which they are bonded, and independently define a substituted or unsubstituted, monocyclic or bicyclic C3-C10 cycloalkyl, cycloalkenyl or heterocyclic ring having one or more N, O, or S atom(s) as the heteroatom(s).

In any aspect or embodiments described herein, wherein the peptide has an amino acid sequence selected from SEQ ID NOS: 1, 14, 16, 19 (potent duodecimal peptide inhibitor (PMI)), 66, 71, 75, or 76.

In another aspect, the present disclosure provides a peptide-oligourea compound or foldamer produced according to the method of the present disclosure.

In any aspect or embodiments described herein, wherein the peptide is a class B GPCR ligand or derivative thereof.

In any aspect or embodiments described herein, wherein the class B GPCR ligand or derivative thereof is selected from the group consisting of lixisenatide, exenatide, liraglutide, albiglutide, dulaglutide, derivatives thereof, and combinations thereof.

In a further aspect, the present disclosure provides a pharmaceutical composition comprising the peptide-oligourea compound or foldamer according to the present disclosure and a pharmaceutically acceptable carrier or excipient.

In another aspect, the present disclosure provides a method of treating, preventing, or ameliorating at least one symptom of, a disease or disorder in a subject, the method comprising administering an effective amount of the peptide-oligourea compound or foldamer of the present disclosure or the pharmaceutical composition of claim 19 to a subject in need thereof, wherein the peptide or pharmaceutical composition is effective for treating, preventing, or ameliorating at least one symptom of the disease or disorder.

In any aspect or embodiments described herein, wherein the disease or disorder is selected from the group consisting of diabetes (such as diabetes mellitus type 1 or diabetes mellitus type 2), a neurodegenerative disease or disorder (such as peripheral neuropathy, Alzheimer's disease, Parkinson's disease, Huntington's disease, amyotrophic sclerosis, multiple sclerosis, traumatic brain injury, or spinal cord injury), or combinations thereof.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

Sequence Listing:

One skilled in the art will appreciate that:
- an amino acid abbreviation followed with a superscript "u" represents a urea substitution with the specified amino acid side chain;
- an amino acid abbreviation followed with a superscript "c" represented a N,N'-linked carbomyl with the specified amino acid side chain; and
- "γ" followed by an amino acid abbreviation represents a γ-amino acid of the specified amino acid.

```
                                           SEQ ID NO: 1
HAEGTFTSDVSSYLEGQAAKEFIAWLVKGRG

SEQ ID NO: 2
HAEGTFTSDVSSYLEGQAAKEFIA"WLVKGRG

SEQ ID NO: 3
HAEGTFTSDVSSYLEGQAAKEFIAA"LVKGRG

SEQ ID NO: 4
HAEGTFTSDVSSYLEGQAAKEFIAW"LVKGRG

SEQ ID NO: 5
HAEGTFTSDVSSYLEGQAAKEFIAWA"VKGRG

SEQ ID NO: 6
HAEGTFTSDVSSYLEGQAAKEFIAWL"VKGRG

SEQ ID NO: 7
HAEGTFTSDVSSYLEGQAAKEFIAWLA"KGRG

SEQ ID NO: 8
HAEGTFTSDVSSYLEGQAAKEFIAWLV"KGRG

SEQ ID NO: 9
HAEGTFTSDVSSYLEGQAAKEFIAWLVK"GR"G

SEQ ID NO: 10
HAEGTFTSDVSSYLEGQAAK"EFIAWLVK"GR"G

SEQ ID NO: 11
HAEGTFTSDVSSYLEGQAAKE"FIAWLVK"GR"G

SEQ ID NO: 12
H"AEGTFTSDVSSYLEGQAAKEFIAWLVKGRG
```

SEQ ID NO: 13
HA"EGTFTSDVSSYLEGQAAKEFIAWLVKGRG

SEQ ID NO: 14
HGEGTFTSDLSKQLEEEAVRLFIEWLKNGGPSSGAPPPS

SEQ ID NO: 15
HA"EGTFTSDLSKQLEEEAVRLFIEWLKNGGPSSGAPPPS

SEQ ID NO: 16
HSQGTFTSDYSKYLDSRRAQDFVQWL Nle NT

SEQ ID NO: 17
H"SQGTFTSDYSKYLDSRRAQDFVQWL Nle NT

SEQ ID NO: 18
HS"QGTFTSDYSKYLDSRRAQDFVQWL Nle NT

SEQ ID NO: 19
TSFAEYWALLSP

SEQ ID NO: 20
T"SFAEYWALLSP

SEQ ID NO: 21
TS"FAEYWALLSP

SEQ ID NO: 22
T"SFAEYWALLS"

SEQ ID NO: 23
T"SFAEYWALLS"P

SEQ ID NO: 24
TS"FAEYWALLS"P

SEQ ID NO: 25
HAEGTFTSDVSSYLEGQAAKEFIAWLVKG"RG

SEQ ID NO: 26
HAEGTFTSDVSSYLEGQAAKEFIAWLVKGR"G

SEQ ID NO: 27
HAEGTFTSDVSSYLEGQAAKEFIAWLVKGRG"

SEQ ID NO: 28
HGEGTFTSDLSKQLEEEAVRLFIEWLKNGGPSSGAPA"PS

SEQ ID NO: 29
HGEGTFTSDLSKQLEEEAVRLFIEWLKNGGPSSGAPPA"S

SEQ ID NO: 30
HGEGTFTSDLSKQLEEEAVRLFIEWLKNGGPSSGAPPPA"

SEQ ID NO: 31
HSQGTFTSDYSKYLDSRRAQDFVQWL Nle" NT

SEQ ID NO: 32
HSQGTFTSDYSKYLDSRRAQDFVQWL Nle N"T

SEQ ID NO: 33
HSQGTFTSDYSKYLDSRRAQDFVQWL Nle NT"

SEQ ID NO: 34
HSQGTFTSDYSKYLDSRRAQDFVQWLA"NT

SEQ ID NO: 35
HSQGTFTSDYSKYLDSRRAQDFVQWL A"T

SEQ ID NO: 36
HSQGTFTSDYSKYLDSRRAQDFVQWL Nle NA"

SEQ ID NO: 37
TSFAEYWA"LLSP

SEQ ID NO: 38
TSFAEYWAL"LSP

SEQ ID NO: 39
TSFAEYWALL"SP

SEQ ID NO: 40
TSFAEYWALLS"P

SEQ ID NO: 41
TSFAEYWALLSP"

SEQ ID NO: 42
H γA EGTFTSDVSSYLEGQAAKEFIAWLVKGRG

SEQ ID NO: 43
H AᶜEGTFTSDVSSYLEGQAAKEFIAWLVKGRG

SEQ ID NO: 44
HAEGTFTSDVSSYY"EGQAAKEFIAWLVKGRG

SEQ ID NO: 45
HAEGTFTSDVSSYLEGQA"AKEFIAWLVKGRG

SEQ ID NO: 46
HAEGTFTSDVSSYLEGQAAKEFIAWLVK"GRG

SEQ ID NO: 47
HGEGTFTSDLSKQLEEEAVRLFIEWLKNGGA"SSGAPPPS

SEQ ID NO: 48
HGEGTFTSDLSKQLEEEAVRLFIEWLKNGGPA"SGAPPPS

SEQ ID NO: 49
HGEGTFTSDLSKQLEEEAVRLFIEWLKNGGPSA"GAPPPS

SEQ ID NO: 50
HGEGTFTSDLSKQLEEEAVRLFIEWLKNGGPSSGAA"PPS

SEQ ID NO: 51
HSQGTFTSDYSKYA"DSRRAQDFVQWL Nle NT

SEQ ID NO: 52
HSQGTFTSDYSKYLDA"RRAQDFVQWL Nle NT

SEQ ID NO: 53
HSQGTFTSDYSKYLDSA"RAQDFVQWL Nle NT

SEQ ID NO: 54
HSQGTFTSDYSKYLDSRRA"QDFVQWL Nle NT

SEQ ID NO: 55
HSQGTFTSDYSKYLDSRRAQDFA"QWL Nle NT

SEQ ID NO: 56
HSQGTFTSDYSKYLDSRRAQDFVA"WL Nle NT

SEQ ID NO: 57
HSQGTFTSDYSKYLDSRRAQDFVQA"L Nle NT

SEQ ID NO: 58
HSQGTFTSDYSKYLDSRRAQDFVQWA" Nle NT

SEQ ID NO: 59
HSQGTFTSDYSK"YLDSRRAQDFVQWL Nle NT

SEQ ID NO: 60
HSQGTFTSDYSKYLDSRRAQ"DFVQWL Nle NT

SEQ ID NO: 61
HSQGTFTSDYSKYLDSRRAQD"FVQWL Nle NT

SEQ ID NO: 62
HSQGTFTSDYSKYLDSRRAQDF"VQWL Nle NT

SEQ ID NO: 63
HSQGTFTSDYSKYLDSRRAQDFV"QWL Nle NT

SEQ ID NO: 64
HSQGTFTSDYSKYLDSRRAQDFVQ"WL Nle NT

SEQ ID NO: 65
HSQGTFTSDYSKYLDSRRAQDFVQW"L Nle NT

SEQ ID NO: 66
HGEGTFTSDLSKQLEEEAVRLFIEWLKNGGPSSGAPPSKKKKKK

-continued

SEQ ID NO: 67
HA"EGTFTSDLSKQLEEEAVRLFIEWLKNGGPSSGAPPSKKKKKK

SEQ ID NO: 68
HS"EGTFTSDLSKQLEEEAVRLFIEWLKNGGPSSGAPPPS

SEQ ID NO: 69
HGEGTFTSDLA"KQLEEEAVRLFIEWLKNGGPSSGAPPPS

SEQ ID NO: 70
HGEGTFTSDLSKQY"EEEAVRLFIEWLKNGGPSSGAPPPS

SEQ ID NO: 71
HGEGTFTSDLSKQMEEEAVRLFIEWLKNGGPSSGAPPPS

SEQ ID NO: 72
HA"EGTFTSDLA"KQLEEEAVRLFIEWLKNGGPSSGAPPPS

SEQ ID NO: 73
HA"EGTFTSDLA"KQLEEEAVRLFIEWLKNGGPSSGAPPSKKKKKK

SEQ ID NO: 74
HGEGTFTSDLS"KQLEEEAVR LFIEWLKNGG PSSGAPPPS

SEQ ID NO: 75
HGEGTFTSDLSKQMEEEAVRLFIEWLKNGGPSSGAPPSKK KKKK

SEQ ID NO: 76
HGEGTFTSDLSKQMEEEAVRLFIEWLKNGGPSSGAPPS

References:
RUNGE, S., WULFF, B. S., MADSEN, K., BRAUNER-OSBORNE, H. and KNUDSEN, L. B. (2003), Different domains of the glucagon and glucagon-like peptide-1 receptors provide the critical determinants of ligand selectivity, Brit. J. Pharmacol., 138: 787-794.

CHICCHI, G. G., GRAZIANO, M. P., KOCH, G., HEY, P. SULLIVAN, K., VICARIO, P. P. and CASIERI, M. A. (1997), Alterations in receptor activation and divalent cation activation of agonist binding by deletion of intracellular domains of the glucagon receptor, J. Biol. Chem., 272: 7765.

What is claimed is:

1. A compound that has an amino acid sequence selected from SEQ ID NOS: 9-11, 72, and 73.

2. The compound of claim 1, wherein the compound has the amino acid sequence of SEQ ID NO: 9.

3. The compound of claim 1, wherein the compound has the amino acid sequence of SEQ ID NO: 10.

4. The compound of claim 1, wherein the compound has the amino acid sequence of SEQ ID NO: 11.

5. A pharmaceutical composition comprising the compound according to claim 1 and a pharmaceutically acceptable carrier or excipient.

6. A method of treating or ameliorating at least one symptom of, a disease or disorder in a subject, the method comprising administering an effective amount of the compound of claim 1 or the pharmaceutical composition of claim 5 to a subject in need thereof, wherein the disease or disorder is selected from the group consisting of diabetes, a neurodegenerative disease or disorder, or combinations thereof, and the peptide compound or pharmaceutical composition is effective for treating, preventing, or ameliorating at least one symptom of the disease or disorder.

7. The method of claim 6, wherein the disease or disorder is diabetes selected from the group consisting of diabetes.

8. The method of claim 6, wherein the disease or disorder is a neurodegenerative disease or disorder.

9. The compound of claim 1, wherein the compound has the amino acid sequence of SEQ ID NO: 72.

10. The compound of claim 1, wherein the compound has the amino acid sequence of SEQ ID NO: 73.

* * * * *

SEQUENCE LISTING

<160> NUMBER OF SEQ ID NOS: 76

<210> SEQ ID NO 1
<211> LENGTH: 31
<212> TYPE: PRT
<213> ORGANISM: Artificial Sequence
<220> FEATURE:
<223> OTHER INFORMATION: Synthetic

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: urea residue with a proteinogenic amino acid
      side chain, such as an alanine side chain

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Xaa Trp Leu Val Lys Gly Arg Gly
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: urea residue with a proteinogenic amino acid
      side chain, such as an alanine side chain

<400> SEQUENCE: 3

```
His Ala Glu Gly Thr Phe Thr Ser Asp Val Ser Ser Tyr Leu Glu Gly
1               5                   10                  15

Gln Ala Ala Lys Glu Phe Ile Ala Xaa Leu Val Lys Gly Arg Gly
            20                  25                  30
```

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: urea residue with a proteinogenic amino acid
      side chain, such as a tryptophan side chain

<400> SEQUENCE: 4

```
His Ala Glu Gly Thr Phe Thr Ser Asp Val Ser Ser Tyr Leu Glu Gly
1               5                   10                  15

Gln Ala Ala Lys Glu Phe Ile Ala Xaa Leu Val Lys Gly Arg Gly
            20                  25                  30
```

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: urea residue with a proteinogenic amino acid
      side chain, such as an alanine side chain

<400> SEQUENCE: 5

```
His Ala Glu Gly Thr Phe Thr Ser Asp Val Ser Ser Tyr Leu Glu Gly
1               5                   10                  15

Gln Ala Ala Lys Glu Phe Ile Ala Trp Xaa Val Lys Gly Arg Gly
            20                  25                  30
```

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: urea residue with a proteinogenic amino acid
      side chain, such as a leucine side chain

<400> SEQUENCE: 6

```
His Ala Glu Gly Thr Phe Thr Ser Asp Val Ser Ser Tyr Leu Glu Gly
1               5                   10                  15

Gln Ala Ala Lys Glu Phe Ile Ala Trp Xaa Val Lys Gly Arg Gly
            20                  25                  30
```

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)

<223> OTHER INFORMATION: urea residue with a proteinogenic amino acid
    side chain, such as an alanine side chain

<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Xaa Lys Gly Arg Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: urea residue with a proteinogenic amino acid
    side chain, such as a valine side chain

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Xaa Lys Gly Arg Gly
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (28)..(28)
<223> OTHER INFORMATION: urea residue with a proteinogenic amino acid
    side chain, such as a lysine side chain
<220> FEATURE:
<221> NAME/KEY: MISC_FEATURE
<222> LOCATION: (30)..(30)
<223> OTHER INFORMATION: urea residue with a proteinogenic amino acid
    side chain, such as an arginine side chain

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Xaa Gly
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: urea residue with a proteinogenic amino acid
    side chain, such as a lysine side chain
<220> FEATURE:
<221> NAME/KEY: MISC_FEATURE
<222> LOCATION: (28)..(28)
<223> OTHER INFORMATION: urea residue with a proteinogenic amino acid
    side chain, such as a lysine side chain
<220> FEATURE:
<221> NAME/KEY: MISC_FEATURE
<222> LOCATION: (30)..(30)
<223> OTHER INFORMATION: urea residue with a proteinogenic amino acid side chain, such as an arginine side chain

<400> SEQUENCE: 10

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Xaa Gly Xaa Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: urea residue with a proteinogenic amino acid
      side chain, such as a glutamate side chain
<220> FEATURE:
<221> NAME/KEY: MISC_FEATURE
<222> LOCATION: (28)..(28)
<223> OTHER INFORMATION: urea residue with a proteinogenic amino acid
      side chain, such as a lysine side chain
<220> FEATURE:
<221> NAME/KEY: MISC_FEATURE
<222> LOCATION: (30)..(30)
<223> OTHER INFORMATION: urea residue with a proteinogenic amino acid
      side chain, such as an arginine side chain

<400> SEQUENCE: 11

His Ala Glu Gly Thr Phe Thr Ser Asp Val Ser Ser Tyr Leu Glu Gly
1               5                   10                  15

Gln Ala Ala Lys Xaa Phe Ile Ala Trp Leu Val Xaa Gly Xaa Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: urea residue with a proteinogenic amino acid
      side chain, such as a histidine side chain

<400> SEQUENCE: 12

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as an alanine side chain

<400> SEQUENCE: 13

His Xaa Glu Gly Thr Phe Thr Ser Asp Val Ser Ser Tyr Leu Glu Gly
1               5                   10                  15

```
Gln Ala Ala Lys Glu Phe Ile Ala Trp Leu Val Lys Gly Arg Gly
        20                  25                  30

<210> SEQ ID NO 14
<211> LENGTH: 39
<212> TYPE: PRT
<213> ORGANISM: Artificial Sequence
<220> FEATURE:
<223> OTHER INFORMATION: Synthetic

<400> SEQUENCE: 14

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as an alanine side chain

<400> SEQUENCE: 15

His Xaa Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Norleucine

<400> SEQUENCE: 16

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: urea residue with a proteinogenic amino acid
      side chain, such as a histidine side chain
```

```
<220> FEATURE:
<221> NAME/KEY: MISC_FEATURE
<222> LOCATION: (27)..(27)
<223> OTHER INFORMATION: Norleucine

<400> SEQUENCE: 17

Xaa Ser Gln Gly Thr Phe Thr Ser Asp Tyr Ser Lys Tyr Leu Asp Ser
1               5                   10                  15
Arg Arg Ala Gln Asp Phe Val Gln Trp Leu Xaa Asn Thr
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as a serine side chain
<220> FEATURE:
<221> NAME/KEY: MISC_FEATURE
<222> LOCATION: (27)..(27)
<223> OTHER INFORMATION: Norleucine

<400> SEQUENCE: 18

His Xaa Gln Gly Thr Phe Thr Ser Asp Tyr Ser Lys Tyr Leu Asp Ser
1               5                   10                  15
Arg Arg Ala Gln Asp Phe Val Gln Trp Leu Xaa Asn Thr
            20                  25

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Thr Ser Phe Ala Glu Tyr Trp Ala Leu Leu Ser Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: urea residue with a proteinogenic amino acid
      side chain, such as a tyrosine side chain

<400> SEQUENCE: 20

Xaa Ser Phe Ala Glu Tyr Trp Ala Leu Leu Ser Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
```

```
<223> OTHER INFORMATION: urea residue with a proteinogenic amino acid
      side chain, such as a serine side chain

<400> SEQUENCE: 21

Thr Xaa Phe Ala Glu Tyr Trp Ala Leu Leu Ser Pro
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: urea residue with a proteinogenic amino acid
      side chain, such as a tyrosine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as a serine side chain

<400> SEQUENCE: 22

Xaa Ser Phe Ala Glu Tyr Trp Ala Leu Leu Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: urea residue with a proteinogenic amino acid
      side chain, such as a tyrosine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as a serine side chain

<400> SEQUENCE: 23

Xaa Ser Phe Ala Glu Tyr Trp Ala Leu Leu Xaa Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as a serine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as a serine side chain

<400> SEQUENCE: 24

Thr Xaa Phe Ala Glu Tyr Trp Ala Leu Leu Xaa Pro
1               5                   10

<210> SEQ ID NO 25
```

```
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (29)..(29)
<223> OTHER INFORMATION: urea residue with a proteinogenic amino acid
      side chain, such as a glycine side chain

<400> SEQUENCE: 25

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Gly
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (30)..(30)
<223> OTHER INFORMATION: urea residue with a proteinogenic amino acid
      side chain, such as an arginine side chain

<400> SEQUENCE: 26

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: urea residue with a proteinogenic amino acid
      side chain, such as a glycine side chain

<400> SEQUENCE: 27

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

<210> SEQ ID NO 28
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (37)..(37)
<223> OTHER INFORMATION: urea residue with a proteinogenic amino acid
      side chain, such as an alanine side chain

<400> SEQUENCE: 28

His Gly Glu Gly Thr Phe Thr Ser Asp Leu Ser Lys Gln Leu Glu Glu
1               5                   10                  15
```

Glu Ala Val Arg Leu Phe Ile Glu Trp Leu Lys Asn Gly Gly Pro Ser
            20                  25                  30

Ser Gly Ala Pro Xaa Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (38)..(38)
<223> OTHER INFORMATION: urea residue with a proteinogenic amino acid
      side chain, such as an alanine side chain

<400> SEQUENCE: 29

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Xaa Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (39)..(39)
<223> OTHER INFORMATION: urea residue with a proteinogenic amino acid
      side chain, such as an alanine side chain

<400> SEQUENCE: 30

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Xaa
        35

<210> SEQ ID NO 31
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: urea residue with a proteinogenic amino acid
      side chain, such as an norleucine side chain

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr
            20                  25

<210> SEQ ID NO 32
<211> LENGTH: 29
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Norleucine
<220> FEATURE:
<221> NAME/KEY: MISC_FEATURE
<222> LOCATION: (28)..(28)
<223> OTHER INFORMATION: urea residue with a proteinogenic amino acid
      side chain, such as an asparagine side chain

<400> SEQUENCE: 32

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Thr
            20                  25

<210> SEQ ID NO 33
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Norleucine
<220> FEATURE:
<221> NAME/KEY: MISC_FEATURE
<222> LOCATION: (29)..(29)
<223> OTHER INFORMATION: urea residue with a proteinogenic amino acid
      side chain, such as a threonine side chain

<400> SEQUENCE: 33

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: urea residue with a proteinogenic amino acid
      side chain, such as an alanine side chain

<400> SEQUENCE: 34

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Thr
            20                  25

<210> SEQ ID NO 35
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Norleucine
<220> FEATURE:
```

```
<221> NAME/KEY: MISC_FEATURE
<222> LOCATION: (28)..(28)
<223> OTHER INFORMATION: urea residue with a proteinogenic amino acid
      side chain, such as an alanine side chain

<400> SEQUENCE: 35

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Xaa Thr
            20                  25

<210> SEQ ID NO 36
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (27)..(27)
<223> OTHER INFORMATION: Norleucine
<220> FEATURE:
<221> NAME/KEY: MISC_FEATURE
<222> LOCATION: (29)..(29)
<223> OTHER INFORMATION: urea residue with a proteinogenic amino acid
      side chain, such as an alanine side chain

<400> SEQUENCE: 36

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Xaa Asn Xaa
            20                  25

<210> SEQ ID NO 37
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: urea residue with a proteinogenic amino acid
      side chain, such as an alanine side chain

<400> SEQUENCE: 37

Thr Ser Phe Ala Glu Tyr Trp Xaa Leu Leu Ser Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: urea residue with a proteinogenic amino acid
      side chain, such as a leucine side chain

<400> SEQUENCE: 38

Thr Ser Phe Ala Glu Tyr Trp Ala Xaa Leu Ser Pro
1               5                   10

<210> SEQ ID NO 39
<211> LENGTH: 12
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: urea residue with a proteinogenic amino acid
      side chain, such as a leucine side chain

<400> SEQUENCE: 39

Thr Ser Phe Ala Glu Tyr Trp Ala Leu Xaa Ser Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: urea residue with a proteinogenic amino acid
      side chain, such as a serine side chain

<400> SEQUENCE: 40

Thr Ser Phe Ala Glu Tyr Trp Ala Leu Leu Xaa Pro
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: urea residue with a proteinogenic amino acid
      side chain, such as a proline side chain

<400> SEQUENCE: 41

Thr Ser Phe Ala Glu Tyr Trp Ala Leu Leu Ser Xaa
1               5                   10

<210> SEQ ID NO 42
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: a gamma amino acid, such as gamma alanine

<400> SEQUENCE: 42

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
```

<223> OTHER INFORMATION: an N,N'-linked carbomyl with a proteinogenic
       amino acid side chain, such as an alanine side chain

<400> SEQUENCE: 43

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
       side chain, such as a tyrosine side chain

<400> SEQUENCE: 44

His Ala Glu Gly Thr Phe Thr Ser Asp Val Ser Ser Tyr Xaa Glu Gly
1               5                   10                  15

Gln Ala Ala Lys Glu Phe Ile Ala Trp Leu Val Lys Gly Arg Gly
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: urea residue with a proteinogenic amino acid
       side chain, such as an alanine side chain

<400> SEQUENCE: 45

His Ala Glu Gly Thr Phe Thr Ser Asp Val Ser Ser Tyr Leu Glu Gly
1               5                   10                  15

Gln Xaa Ala Lys Glu Phe Ile Ala Trp Leu Val Lys Gly Arg Gly
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (28)..(28)
<223> OTHER INFORMATION: urea residue with a proteinogenic amino acid
       side chain, such as a lysine side chain

<400> SEQUENCE: 46

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Gly Arg Gly
            20                  25                  30

<210> SEQ ID NO 47
<211> LENGTH: 39
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: urea residue with a proteinogenic amino acid
      side chain, such as an alanine side chain

<400> SEQUENCE: 47

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Xaa Ser
            20                  25                  30

Ser Gly Ala Pro Pro Pro Ser
        35

<210> SEQ ID NO 48
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (32)..(32)
<223> OTHER INFORMATION: urea residue with a proteinogenic amino acid
      side chain, such as an alanine side chain

<400> SEQUENCE: 48

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Xaa
            20                  25                  30

Ser Gly Ala Pro Pro Pro Ser
        35

<210> SEQ ID NO 49
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (33)..(33)
<223> OTHER INFORMATION: urea residue with a proteinogenic amino acid
      side chain, such as an alanine side chain

<400> SEQUENCE: 49

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Xaa Gly Ala Pro Pro Pro Ser
        35

<210> SEQ ID NO 50
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (36)..(36)
<223> OTHER INFORMATION: urea residue with a proteinogenic amino acid
      side chain, such as an alanine side chain
```

<400> SEQUENCE: 50

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Xaa Pro Pro Ser
            35

<210> SEQ ID NO 51
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 51

His Ser Gln Gly Thr Phe Thr Ser Asp Tyr Ser Lys Tyr Xaa Asp Ser
1               5                   10                  15

Arg Arg Ala Gln Asp Phe Val Gln Trp Leu Xaa Asn Thr
            20                  25

<210> SEQ ID NO 52
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 52

His Ser Gln Gly Thr Phe Thr Ser Asp Tyr Ser Lys Tyr Leu Asp Xaa
1               5                   10                  15

Arg Arg Ala Gln Asp Phe Val Gln Trp Leu Xaa Asn Thr
            20                  25

<210> SEQ ID NO 53
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (17)..(17)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 53

His Ser Gln Gly Thr Phe Thr Ser Asp Tyr Ser Lys Tyr Leu Asp Ser
1               5                   10                  15

Xaa Arg Ala Gln Asp Phe Val Gln Trp Leu Xaa Asn Thr
            20                  25

<210> SEQ ID NO 54
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (19)..(19)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 54

His Ser Gln Gly Thr Phe Thr Ser Asp Tyr Ser Lys Tyr Leu Asp Ser
1               5                   10                  15

Arg Arg Xaa Gln Asp Phe Val Gln Trp Leu Xaa Asn Thr
            20                  25

<210> SEQ ID NO 55
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 55

His Ser Gln Gly Thr Phe Thr Ser Asp Tyr Ser Lys Tyr Leu Asp Ser
1               5                   10                  15

Arg Arg Ala Gln Asp Phe Xaa Gln Trp Leu Xaa Asn Thr
            20                  25

<210> SEQ ID NO 56
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 56

His Ser Gln Gly Thr Phe Thr Ser Asp Tyr Ser Lys Tyr Leu Asp Ser
1               5                   10                  15

```
Arg Arg Ala Gln Asp Phe Val Xaa Trp Leu Xaa Asn Thr
            20                  25
```

<210> SEQ ID NO 57
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 57

```
His Ser Gln Gly Thr Phe Thr Ser Asp Tyr Ser Lys Tyr Leu Asp Ser
1               5                   10                  15

Arg Arg Ala Gln Asp Phe Val Gln Xaa Leu Xaa Asn Thr
            20                  25
```

<210> SEQ ID NO 58
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (26)..(26)
<223> OTHER INFORMATION: urea residue with a proteinogenic amino acid
      side chain, such as an alanine side chain
<220> FEATURE:
<221> NAME/KEY: MISC_FEATURE
<222> LOCATION: (27)..(27)
<223> OTHER INFORMATION: Norleucine

<400> SEQUENCE: 58

```
His Ser Gln Gly Thr Phe Thr Ser Asp Tyr Ser Lys Tyr Leu Asp Ser
1               5                   10                  15

Arg Arg Ala Gln Asp Phe Val Gln Trp Xaa Xaa Asn Thr
            20                  25
```

<210> SEQ ID NO 59
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: urea residue with a proteinogenic amino acid
      side chain, such as a lysine side chain
<220> FEATURE:
<221> NAME/KEY: MISC_FEATURE
<222> LOCATION: (27)..(27)
<223> OTHER INFORMATION: Norleucine

<400> SEQUENCE: 59

```
His Ser Gln Gly Thr Phe Thr Ser Asp Tyr Ser Xaa Tyr Leu Asp Ser
1               5                   10                  15

Arg Arg Ala Gln Asp Phe Val Gln Trp Leu Xaa Asn Thr
            20                  25
```

<210> SEQ ID NO 60
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (20)..(20)
<223> OTHER INFORMATION: urea residue with a proteinogenic amino acid
      side chain, such as a glutamine side chain
<220> FEATURE:
<221> NAME/KEY: MISC_FEATURE
<222> LOCATION: (27)..(27)
<223> OTHER INFORMATION: Norleucine

<400> SEQUENCE: 60

His Ser Gln Gly Thr Phe Thr Ser Asp Tyr Ser Lys Tyr Leu Asp Ser
1               5                   10                  15

Arg Arg Ala Xaa Asp Phe Val Gln Trp Leu Xaa Asn Thr
            20                  25

<210> SEQ ID NO 61
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (21)..(21)
<223> OTHER INFORMATION: urea residue with a proteinogenic amino acid
      side chain, such as an aspartate side chain
<220> FEATURE:
<221> NAME/KEY: MISC_FEATURE
<222> LOCATION: (27)..(27)
<223> OTHER INFORMATION: Norleucine

<400> SEQUENCE: 61

His Ser Gln Gly Thr Phe Thr Ser Asp Tyr Ser Lys Tyr Leu Asp Ser
1               5                   10                  15

Arg Arg Ala Gln Xaa Phe Val Gln Trp Leu Xaa Asn Thr
            20                  25

<210> SEQ ID NO 62
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: urea residue with a proteinogenic amino acid
      side chain, such as a phenylalanine side chain
<220> FEATURE:
<221> NAME/KEY: MISC_FEATURE
<222> LOCATION: (27)..(27)
<223> OTHER INFORMATION: Norleucine

<400> SEQUENCE: 62

His Ser Gln Gly Thr Phe Thr Ser Asp Tyr Ser Lys Tyr Leu Asp Ser
1               5                   10                  15

Arg Arg Ala Gln Asp Xaa Val Gln Trp Leu Xaa Asn Thr
            20                  25

<210> SEQ ID NO 63
<211> LENGTH: 29
<212> TYPE: PRT

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: urea residue with a proteinogenic amino acid
      side chain, such as a valine side chain
<220> FEATURE:
<221> NAME/KEY: MISC_FEATURE
<222> LOCATION: (27)..(27)
<223> OTHER INFORMATION: Norleucine

<400> SEQUENCE: 63

His Ser Gln Gly Thr Phe Thr Ser Asp Tyr Ser Lys Tyr Leu Asp Ser
1               5                   10                  15

Arg Arg Ala Gln Asp Phe Xaa Gln Trp Leu Xaa Asn Thr
            20                  25

<210> SEQ ID NO 64
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (24)..(24)
<223> OTHER INFORMATION: urea residue with a proteinogenic amino acid
      side chain, such as a glutamine side chain
<220> FEATURE:
<221> NAME/KEY: MISC_FEATURE
<222> LOCATION: (27)..(27)
<223> OTHER INFORMATION: Norleucine

<400> SEQUENCE: 64

His Ser Gln Gly Thr Phe Thr Ser Asp Tyr Ser Lys Tyr Leu Asp Ser
1               5                   10                  15

Arg Arg Ala Gln Asp Phe Val Xaa Trp Leu Xaa Asn Thr
            20                  25

<210> SEQ ID NO 65
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (25)..(25)
<223> OTHER INFORMATION: urea residue with a proteinogenic amino acid
      side chain, such as a tryptophan side chain
<220> FEATURE:
<221> NAME/KEY: MISC_FEATURE
<222> LOCATION: (27)..(27)
<223> OTHER INFORMATION: Norleucine

<400> SEQUENCE: 65

His Ser Gln Gly Thr Phe Thr Ser Asp Tyr Ser Lys Tyr Leu Asp Ser
1               5                   10                  15

Arg Arg Ala Gln Asp Phe Val Gln Xaa Leu Xaa Asn Thr
            20                  25

<210> SEQ ID NO 66
<211> LENGTH: 44
<212> TYPE: PRT
<213> ORGANISM: Artificial Sequence
<220> FEATURE:
<223> OTHER INFORMATION: Synthetic

```
<400> SEQUENCE: 66

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 67
<211> LENGTH: 44
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as an alanine side chain

<400> SEQUENCE: 67

His Xaa Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 68
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as a serine side chain

<400> SEQUENCE: 68

His Xaa Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain

<400> SEQUENCE: 69

His Gly Glu Gly Thr Phe Thr Ser Asp Leu Xaa Lys Gln Leu Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (14)..(14)
<223> OTHER INFORMATION: urea residue with a proteinogenic amino acid
      side chain, such as a tryosine side chain

<400> SEQUENCE: 70

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: Synthetic

<400> SEQUENCE: 71

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as an alanine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain

<400> SEQUENCE: 72

His Xaa Glu Gly Thr Phe Thr Ser Asp Leu Xaa Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 73
<211> LENGTH: 44

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: urea residue with a proteinogenic amino acid
      side chain, such as an alanine side chain
<220> FEATURE:
<221> NAME/KEY: MISC_FEATURE
<222> LOCATION: (11)..(11)
<223> OTHER INFORMATION: urea residue with a proteinogenic amino acid
      side chain, such as an alanine side chain

<400> SEQUENCE: 73

His Xaa Glu Gly Thr Phe Thr Ser Asp Leu Xaa Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 74
<211> LENGTH: 39
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: urea residue with a proteinogenic amino acid
      side chain, such as a serine side chain

<400> SEQUENCE: 74

His Gly Glu Gly Thr Phe Thr Ser Asp Leu Xaa Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 75
<211> LENGTH: 44
<212> TYPE: PRT
<213> ORGANISM: Artificial Sequence
<220> FEATURE:
<223> OTHER INFORMATION: Synthetic

<400> SEQUENCE: 75

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 76
<211> LENGTH: 38
<212> TYPE: PRT
<213> ORGANISM: Artificial Sequence
<220> FEATURE:
<223> OTHER INFORMATION: Synthetic

<400> SEQUENCE: 76
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20              25              30

Ser Gly Ala Pro Pro Ser
        35
```